US012092639B2

(12) United States Patent
Daniels

(10) Patent No.: US 12,092,639 B2
(45) Date of Patent: *Sep. 17, 2024

(54) USING EXHALED BREATH CONDENSATE, AEROSOLS AND GASES FOR DETECTING BIOMARKERS

(71) Applicant: John J. Daniels, Madison, CT (US)

(72) Inventor: John J. Daniels, Madison, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 16/882,447

(22) Filed: May 23, 2020

(65) Prior Publication Data

US 2021/0325382 A1    Oct. 21, 2021

Related U.S. Application Data

(60) Provisional application No. 63/012,247, filed on Apr. 19, 2020, provisional application No. 63/019,378, (Continued)

(51) Int. Cl.
*G01N 33/543* (2006.01)

(52) U.S. Cl.
CPC .  *G01N 33/54386* (2013.01); *G01N 33/54388* (2021.08); *G01N 2333/165* (2013.01)

(58) Field of Classification Search
CPC ....... G01N 33/54386; G01N 33/54388; G01N 33/56983; G01N 33/54387;
(Continued)

(56) References Cited

U.S. PATENT DOCUMENTS

| 4,158,196 A | 6/1979 | Crawford, Jr. |
| 5,637,176 A | 6/1997 | Gilleo et al. |

(Continued)

FOREIGN PATENT DOCUMENTS

| CN | 104225791 | 6/2013 |
| CN | 104220128 | 7/2016 |

(Continued)

OTHER PUBLICATIONS

Bhardwaj et al., "Recent advancements in the measurement of pathogenic airborne viruses", 2021, Journal of Hazardous Materials, vol. 420 (Year: 2021).*

(Continued)

*Primary Examiner* — Christopher L Chin
*Assistant Examiner* — Christina Lusi
(74) *Attorney, Agent, or Firm* — John J. Daniels; David J. Powsner; Davis Malm D'Agostine PC

(57) ABSTRACT

An apparatus for detecting a biomarker includes a particulate capturing structure for receiving and capturing exhaled breath aerosol (EBA) particulate from airway linings of a user, the particulate capturing structure having an aerosol particulate testing system for receiving the captured particulate and detecting a first biomarker, wherein the aerosol particulate testing system includes a dissolvable EBA sample collector film for capturing EBA particulate. The apparatus may include a droplet harvesting structure for converting breath vapor to a fluid droplet for forming a fluid sample and a testing system having a biomarker testing zone for receiving the fluid sample and detecting a biomarker.

19 Claims, 39 Drawing Sheets dissolvable EBA particulate collector

Related U.S. Application Data filed on May 3, 2020, provisional application No. 63/026,052, filed on May 17, 2020.

(58) Field of Classification Search
CPC .. G01N 2333/165; A61B 5/097; A61B 5/082; A61B 5/6803
USPC ...................... 128/200.24; 435/7.1
See application file for complete search history.

(56) References Cited

U.S. PATENT DOCUMENTS

| | | |
|---|---|---|
| 6,316,274 B1 | 11/2001 | Herron et al. |
| 6,411,276 B1 | 6/2002 | Braun et al. |
| 6,464,171 B2 | 10/2002 | Ruffin |
| 6,609,018 B2 | 8/2003 | Cory et al. |
| 6,892,098 B2 | 5/2005 | Ayal et al. |
| 6,908,572 B1 | 6/2005 | Derbyshire et al. |
| 6,930,590 B2 | 8/2005 | Ling et al. |
| 6,965,842 B2 | 11/2005 | Rekimoto |
| 7,013,179 B2 | 3/2006 | Carter et al. |
| 7,052,854 B2 | 5/2006 | Melker |
| 7,228,178 B2 | 6/2007 | Carroll et al. |
| 7,261,812 B1 | 8/2007 | Karp et al. |
| 7,539,724 B1 | 5/2009 | Callaghan |
| 7,779,840 B2 | 8/2010 | Acker |
| 8,002,712 B2* | 8/2011 | Meka .................. G01N 33/497 600/529 |
| 8,098,046 B2 | 1/2012 | Poisner |
| 8,280,503 B2 | 10/2012 | Linderman |
| 8,378,964 B2 | 2/2013 | Ullrich et al. |
| 8,394,030 B2 | 3/2013 | Varga et al. |
| 8,552,847 B1 | 10/2013 | Hill |
| 8,560,082 B2 | 10/2013 | Wei |
| 8,617,228 B2 | 12/2013 | Wittenberger et al. |
| 8,620,434 B2 | 12/2013 | Bodlaender |
| 9,022,029 B2 | 5/2015 | Varga et al. |
| 9,169,521 B1 | 10/2015 | Rajagopal |
| 9,357,946 B2* | 6/2016 | Johnson ................ A61B 5/097 |
| 9,390,630 B2 | 7/2016 | Daniels |
| 9,435,788 B2 | 9/2016 | Killard et al. |
| 9,874,563 B2 | 1/2018 | Zurakowski |
| 9,968,281 B2 | 5/2018 | Bulbrook |
| 10,048,213 B2 | 8/2018 | Wilds |
| 10,238,079 B1 | 3/2019 | Eby |
| 10,274,487 B2 | 4/2019 | Ludwig |
| 10,381,826 B2 | 8/2019 | Gao |
| 10,393,753 B2 | 8/2019 | Milton et al. |
| 10,437,335 B2 | 10/2019 | Daniels |
| 10,463,275 B2 | 11/2019 | King-Smith |
| 10,481,688 B1 | 11/2019 | Wang |
| 10,589,277 B2 | 3/2020 | Ahmad et al. |
| 10,617,363 B2 | 4/2020 | Diebold et al. |
| 10,670,580 B2 | 6/2020 | Javanmard et al. |
| 10,753,949 B2 | 8/2020 | Grafman et al. |
| 10,859,473 B2 | 12/2020 | Wu et al. |
| 2001/0023076 A1 | 9/2001 | Guan |
| 2002/0125135 A1 | 9/2002 | Derand |
| 2002/0130311 A1 | 9/2002 | Lieber et al. |
| 2003/0068053 A1 | 4/2003 | Chu |
| 2003/0149457 A1 | 8/2003 | Tcheng et al. |
| 2003/0170602 A1 | 9/2003 | Hagita et al. |
| 2004/0019301 A1 | 1/2004 | Wong |
| 2004/0023514 A1 | 2/2004 | Moriya et al. |
| 2004/0057176 A1 | 3/2004 | Dhawan |
| 2004/0112964 A1 | 6/2004 | Empedocles et al. |
| 2004/0174431 A1 | 9/2004 | Stienstra |
| 2004/0244564 A1 | 12/2004 | McGregor |
| 2006/0137511 A1 | 6/2006 | McGregor |
| 2007/0000374 A1 | 1/2007 | Clark et al. |
| 2007/0031283 A1 | 2/2007 | Davis et al. |
| 2007/0068810 A1 | 3/2007 | Tsukashima et al. |
| 2007/0110613 A1 | 5/2007 | Pachl et al. |
| 2007/0250119 A1 | 10/2007 | Tyler et al. |
| 2007/0282228 A1 | 12/2007 | Einav et al. |
| 2008/0045825 A1 | 2/2008 | Melker et al. |
| 2008/0103639 A1 | 5/2008 | Troy et al. |
| 2008/0185295 A1 | 8/2008 | Briman et al. |
| 2008/0188306 A1 | 8/2008 | Tetterington et al. |
| 2008/0214947 A1 | 9/2008 | Hunt et al. |
| 2009/0053683 A1 | 2/2009 | Brown et al. |
| 2009/0231276 A1 | 9/2009 | Ullrich et al. |
| 2009/0255535 A1* | 10/2009 | Kanzer ................ A62B 18/025 128/206.14 |
| 2009/0326406 A1 | 12/2009 | Tan et al. |
| 2010/0087749 A1* | 4/2010 | Tovey .................. A62B 18/025 600/543 |
| 2010/0106044 A1 | 4/2010 | Linderman |
| 2011/0048213 A1 | 3/2011 | Choi et al. |
| 2011/0094306 A1 | 4/2011 | Bratkovski et al. |
| 2011/0183304 A1 | 7/2011 | Wallace |
| 2011/0238079 A1 | 9/2011 | Hannaford et al. |
| 2012/0035513 A1 | 2/2012 | Afshar |
| 2012/0094263 A1 | 4/2012 | Seitz |
| 2012/0167747 A1 | 7/2012 | Luchinskiy |
| 2012/0216666 A1 | 8/2012 | Fresolone |
| 2012/0260789 A1 | 10/2012 | Ur et al. |
| 2013/0029791 A1 | 1/2013 | Rose et al. |
| 2013/0118339 A1 | 5/2013 | Lee et al. |
| 2013/0207890 A1 | 8/2013 | Young |
| 2013/0209980 A1 | 8/2013 | Kuchenbecker |
| 2013/0310122 A1 | 11/2013 | Piccionielli |
| 2014/0038139 A1 | 2/2014 | AlDossary |
| 2014/0180361 A1 | 6/2014 | Burdick et al. |
| 2014/0186810 A1 | 7/2014 | Falash et al. |
| 2014/0208204 A1 | 7/2014 | Lacroix et al. |
| 2014/0240103 A1 | 8/2014 | Lake et al. |
| 2014/0248594 A1 | 9/2014 | Navas |
| 2014/0282105 A1 | 9/2014 | Nordstrom |
| 2014/0364758 A1 | 12/2014 | Schindhelm et al. |
| 2015/0024381 A1 | 1/2015 | Zurakowski |
| 2015/0050623 A1 | 2/2015 | Falash et al. |
| 2015/0140528 A1 | 5/2015 | Sikstrom et al. |
| 2015/0140529 A1 | 5/2015 | Tinjust |
| 2015/0221230 A1 | 8/2015 | Karadjian et al. |
| 2015/0269863 A1 | 9/2015 | Shrewsbury |
| 2015/0279238 A1 | 10/2015 | Forte et al. |
| 2015/0294585 A1 | 10/2015 | Kullok et al. |
| 2015/0294597 A1 | 10/2015 | Rizzo |
| 2015/0302763 A1 | 10/2015 | Gleim et al. |
| 2015/0314195 A1 | 11/2015 | Bekri |
| 2015/0317910 A1 | 11/2015 | Daniels |
| 2015/0323993 A1 | 11/2015 | Levesque et al. |
| 2016/0030751 A1 | 2/2016 | Ghosh et al. |
| 2016/0150992 A1 | 6/2016 | Lee |
| 2017/0056644 A1 | 3/2017 | Chahine |
| 2017/0072369 A1 | 3/2017 | Mitra et al. |
| 2017/0273864 A1 | 9/2017 | Kaufman |
| 2017/0356899 A1 | 12/2017 | Güder et al. |
| 2017/0358235 A1 | 12/2017 | Daniels |
| 2017/0370030 A1 | 12/2017 | Podhajny |
| 2018/0242884 A1 | 8/2018 | Kulkarni et al. |
| 2018/0303383 A1 | 10/2018 | Connor |
| 2019/0056788 A1 | 2/2019 | Piper |
| 2019/0076647 A1 | 3/2019 | Tamaki et al. |
| 2019/0136423 A1 | 5/2019 | Podhajny |
| 2019/0201619 A1 | 7/2019 | Gibson et al. |
| 2019/0317115 A1 | 10/2019 | MacLean |
| 2020/0041485 A1* | 2/2020 | Funch-Nielsen ...... A61B 5/082 |
| 2020/0155069 A1 | 5/2020 | Bogdanovich |
| 2020/0281504 A1 | 9/2020 | Ahmad et al. |
| 2020/0384470 A1 | 12/2020 | Huff et al. |
| 2021/0198872 A1 | 7/2021 | Colman et al. |
| 2021/0321903 A1 | 10/2021 | Daniels |
| 2021/0325279 A1 | 10/2021 | Daniels |
| 2021/0325381 A1 | 10/2021 | Daniels |
| 2021/0325382 A1 | 10/2021 | Daniels |
| 2021/0382045 A1 | 12/2021 | Aran et al. |
| 2022/0034854 A1* | 2/2022 | Chen .................... A61B 5/082 |
| 2022/0322963 A1* | 10/2022 | Chen .................. G01N 30/7206 |

(56) References Cited

U.S. PATENT DOCUMENTS

| | | |
|---|---|---|
| 2023/0200678 A1 | 6/2023 | Daniels |
| 2023/0333038 A1 | 10/2023 | Daniels |

FOREIGN PATENT DOCUMENTS

| | | | |
|---|---|---|---|
| CN | 106644606 | 5/2017 | |
| CN | 108883335 | 11/2018 | |
| CN | 110381826 | 10/2019 | |
| CN | 111387950 A | 7/2020 | |
| EP | 2801389 | 11/2014 | |
| EP | 3544495 | 10/2019 | |
| JP | 2020516327 A | 6/2020 | |
| WO | WO1997004310 | 6/1997 | |
| WO | WO 2010082993 | 7/2010 | |
| WO | WO 2013071307 | 5/2013 | |
| WO | WO 2014038049 | 3/2014 | |
| WO | WO 2014113813 | 7/2014 | |
| WO | WO 2015124580 | 8/2015 | |
| WO | 2015166444 A1 | 11/2015 | |
| WO | WO 2016168117 | 10/2016 | |
| WO | WO-2017048881 A1 * | 3/2017 | ........... A61B 5/0836 |
| WO | WO 2018098046 | 5/2018 | |
| WO | 2019046712 A1 | 3/2019 | |
| WO | 2019178247 A1 | 9/2019 | |
| WO | WO-2020176607 A1 * | 9/2020 | ............. B01L 3/502 |
| WO | WO 2020234338 | 11/2020 | |
| WO | WO 2020257356 | 12/2020 | |
| WO | WO-2021041571 A1 * | 3/2021 | ............. A61B 10/00 |
| WO | WO 2021216386 | 10/2021 | |
| WO | WO 2023023481 | 2/2023 | |
| WO | WO 2023023678 | 2/2023 | |
| WO | WO 2023205574 | 10/2023 | |

OTHER PUBLICATIONS

Li et al., "Comparing the performance of 3 bioaerosol samplers for influenza virus", 2018, Journal of Aerosol Science, vol. 115 (Year: 2018).*

Zhao et al., "Airborne virus sampling—Efficiencies of samplers and their detection limits for infectious bursal disease virus (IBDV)", 2014, Annals of Agricultural and Environmental Medicine, vol. 21 (Year: 2014).*

Maier et al., "Toward Continuous Monitoring of Breath Biochemistry: A Paper-Based Wearable Sensor for Real-Time Hydrogen Peroxide Measurement in Simulated Breath", 2019, ACS Sensors, vol. 4, p. 2945-2951 (Year: 2019).*

Meyyappan, M. (2016), Carbon Nanotube-Based Chemical Sensors. Small, 12: 2118-2129. (Year: 2016).*

Kari Rodriquez, International Search Report and Written Opinion mailed Oct. 6, 2021 for related PCT application Serial No. PCT/US21/27854, 39 pages, ISA/US, Alexandria, VA.

Nguyen et al., "Wearable materials with embedded synthetic biology sensors for biomolecule detection", 2021, Nature Biotechnology, vol. 39 (Year: 2021).

Nguyen, Wearable materials with embedded synthetic biology sensors for biomolecule detection, Nature Biotechnology, vol. 39, Nov. 2021, 1366-1374.

U.S. Appl. No. 16/876,054, Using Exhaled Breath Condensate forTesting for a Biomarker of Covid-19.

U.S. Appl. No. 17/065,488, Mask-Based Testing System for Detecting Biomarkers in Exhaled Breath Condensate, Aerosols and Gases.

U.S. Appl. No. 17/189,711, Mask-Based Diagnostic System Using Exhaled Breath Condensate.

U.S. Appl. No. 17/864,343, Mask-Based Diagnostic Device and Wafer-Level Functionalization of a Packaged Semiconductor Biosensor.

U.S. Appl. No. 18/046,911, Mask-Based Diagnostic System Using Exhaled Breath Condensate.

U.S. Appl. No. 18/113,777, Mask-Based Diagnostic Device With Accessibility Features.

U.S. Appl. No. 18/301,967, Mask-Based Diagnostic Utilizing Ai Algorithms for Improved Patient Outcomes.

U.S. Appl. No. 18/357,870, Mask-Based Diagnostic Utilizing Ai Algorithms for Improved Patient Outcomes.

U.S. Appl. No. 63/012,247, Low Cost, Scalable, Accurate, and Easy-to-Use Testing System for Covid-19.

U.S. Appl. No. 63/019,378, Using Exhaled Breath Condensate for Testing for a Biomarker of Covid-19.

U.S. Appl. No. 63/026,052, Using Exhaled Breath Condensate for Testing for a Biomarker of Covid-19.

U.S. Appl. No. 63/233,473, Diagnostic Platform for Testing Exhaled Breath Condensate.

U.S. Appl. No. 63/245,295, Diagnostic Platform for Testing Exhaled Breath Condensate and Universal Biosensor.

U.S. Appl. No. 63/331,841, Mask-Based Diagnostic Device and Packaged Semiconductor Biosensor.

PCT/US21/24404, Mask-Based Diagnostic System Using Exhaled Breath Condensate.

PCT/US21/27740, Mask-Based Diagnostic System Using Exhaled Breath Condensate.

PCT/US21/27854, Mask-Based Diagnostic System Using Exhaled Breath Condensate.

PCT/US22/74961, Diagnostic Platform for Testing Exhaled Breath Condensate.

PCT/US22/76511, Diagnostic Platform for Testing Exhaled Breath Condensate and Universal Biosensor.

PCT/US23/65562, Mask-Based Diagnostic Device and Wafer-Level Functionalization of a Packaged Semiconductor Biosensor.

U.S. Appl. No. 14/269,133, Accelerated Learning, Entertainment and Cognitive Therapy Using Augmented Reality Comprising Combined Haptic, Auditory, and Visual Stimulation, filed May 3, 2014.

U.S. Appl. No. 15/177,373, Accelerated Learning, Entertainment and Cognitive Therapy Using Augmented Reality Comprising Combined Haptic, Auditory, and Visual Stimulation, filed Jun. 9, 2016.

U.S. Appl. No. 15/562,752, Wearable Electronic, Multi-Sensory, Human/Machine, Human/Human Interfaces, filed Sep. 28, 2017.

U.S. Appl. No. 16/464,171, Haptic Human Machine Interface and Wearable Electronics Methods and Apparatus, filed May 24, 2019.

U.S. Appl. No. 16/737,055, Fabric, Connections and Functional Structures for Wearable Electronic Garments and Applications for the Same, filed Jan. 8, 2020.

U.S. Appl. No. 16/910,626, Wearable Electronic Haptic Feedback System for VR/AR and Gaming, filed Jun. 24, 2020.

U.S. Appl. No. 17/201,091, Methods and Apparatus for a Wearable Electronic Digital Therapeutic Device, filed Mar. 15, 2021.

U.S. Appl. No. 17/481,240, Accelerated Learning, Entertainment and Cognitive Therapy Using Augmented Reality Comprising Combined Haptic, Auditory, and Visual Stimulation, filed Sep. 21, 2021.

U.S. Appl. No. 63/327,921, Wearable Electronic for Monitoring a Change in a Physical Condition of a Patient, filed Apr. 6, 2022.

PCT/US19/45429, Methods and Apparatus for a Wearable Electronic Digital Therapeutic Device.

PCT/US23/65316, Wearable Electronic for Digital Healthcare.

Daniels et al., A mask-based diagnostic platform for point-of-care screening of Covid-19, Biosensors and Bioelectronics. Jul. 8, 2021, vol. 192, pp. 1-8.

Bhardwaj et al., Recent progress in nanomaterial-based sensing of airborne viral and bacterial pathogens. Environment International. Oct. 25, 2020, vol. 146, No. 106183, pp. 1-18.

Hajian et al., Detection of unamplified target genes via CRISPR-Cas9 immobilized on a graphene field-effect transistor. Nature Biomedical Engineering. Jun. 2019, vol. 3, No. 6, pp. 427-437.

Kim et al., Bio-inspired catechol conjugation converts water-insoluble chitosan into a highly water-soluble, adhesive chitosan derivative for hydrogels and LbL assembly. Biomaterials Science. May 2, 2013, vol. 1, pp. 783-790.

Kim et al., Nanowire-integrated microfluidic devices for facile and reagent-free mechanical cell lysis. Lab on a Chip. May 15, 2012, vol. 12, pp. 2914-2921.

Li et al., Rapid and unamplified identification of COVID-19 with morpholino-modified graphene field-effect transistor nanosensor. Biosensors and Bioelectronics. Mar. 30, 2021, vol. 183, pp. 1-9.

(56) References Cited

OTHER PUBLICATIONS

Sadir, S., Interfacial Wicking Flow Through Hierarchical Structure of Natural Cellulose Fibers For Biomedical Microfluidic Devices. Dissertation. Universiti Teknologi Malaysia. Nov. 2015 [online]. [Retrieved on Mar. 7, 2023]. Retrieved from the internet: <URL: http://eprints.utm.my/ld/eprint/78509/1/SahbaSadirMFKM2015>.

Xie et al., "Nanofiltration" Enabled by Super-Absorbent Polymer Beads for Concentrating Microorganisms in Water Samples. Nature. Feb. 15, 2016, vol. 6, No. 20516, pp. 1-8.

Sorribas et al., Photolithographic generation of protein micropatterns for neuron culture applications. Biomaterials. Feb. 2002, vol. 23, No. 3, pp. 893-900.

* cited by examiner

Wearable Electronic Breath Chemistry Sensor

Isolated View

Screen Printed Vapor Droplet Harvestor

1) Backside of Etched Flex Circuit

2) Form Sweat Transfer Aperture

3) Screen Print Hydrophobic Field

4) Screen Print Hydrophilic Channels

EBC sample collector assembly

Lateral Flow Assay assembly multiple test lines
emitter/detector
electronics

Pull Tab

Adsorbent Pad

Sample Pad
Conjugate Pad

Nanoscale Bioreceptor Sensor
with Bluetooth Electronics

EBC Sample Collector

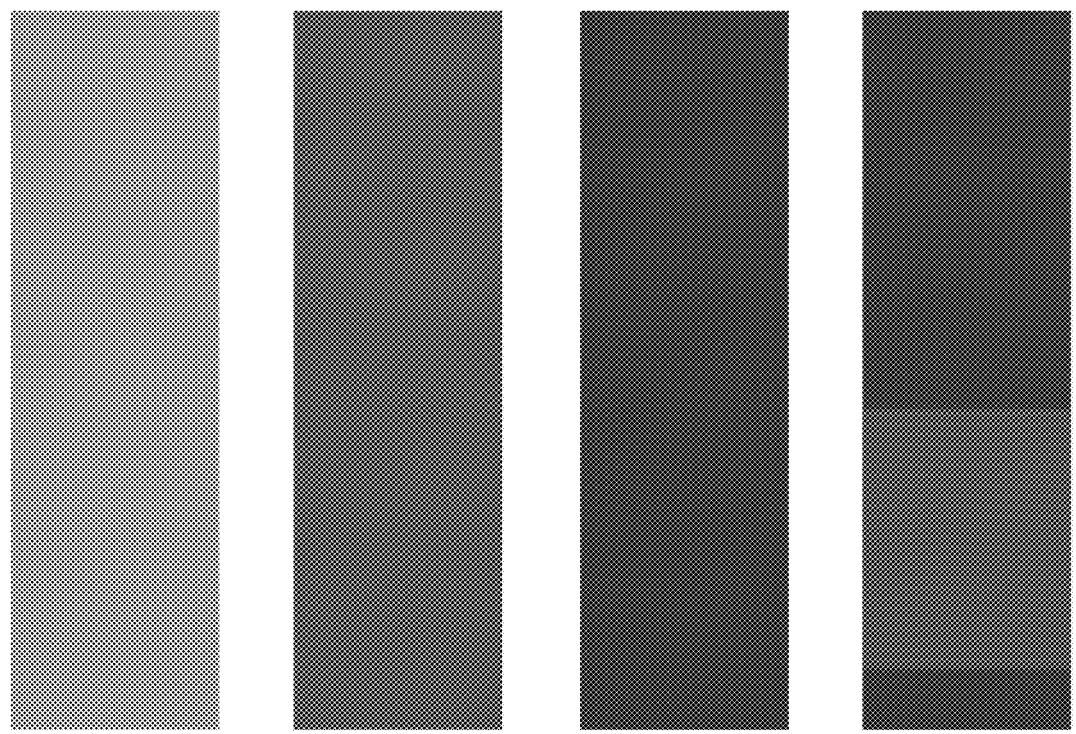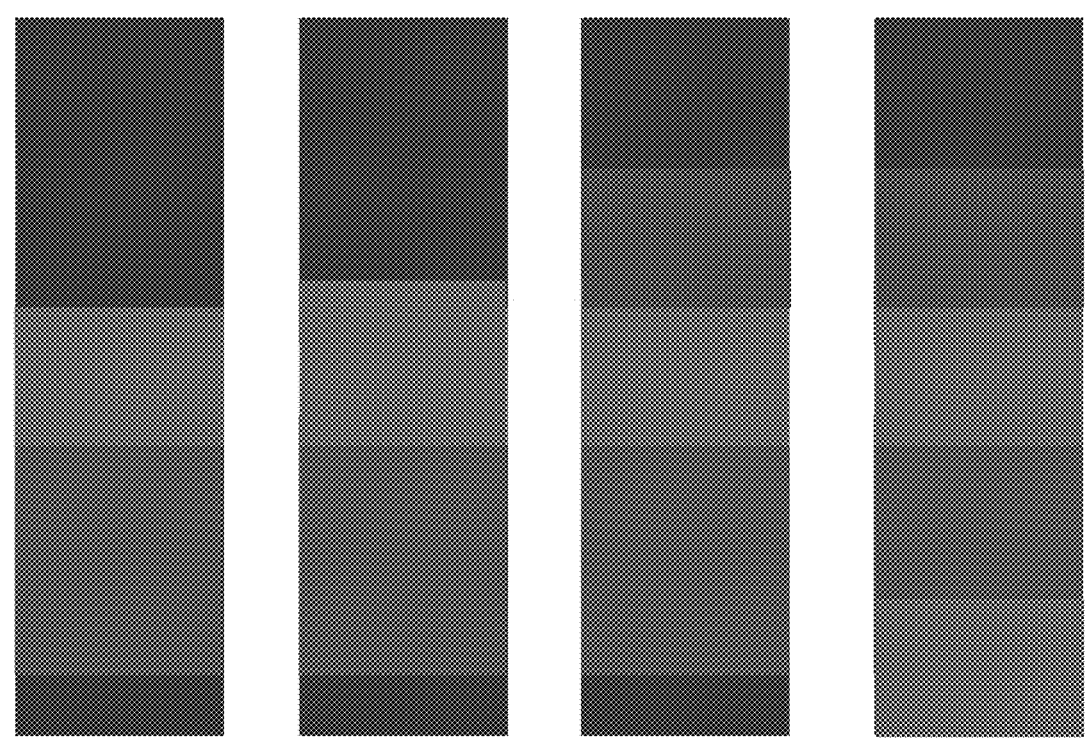
Figure 23

Bond fabric, filter, and other layers through R2R lamination process or Cut each material layer without bonding into blanks
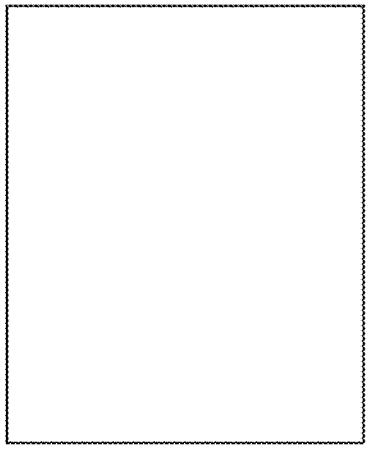
Fabric
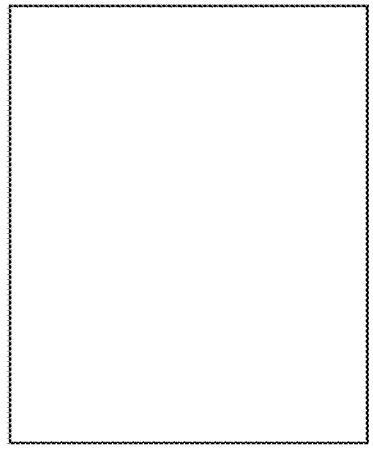
Filter Medium
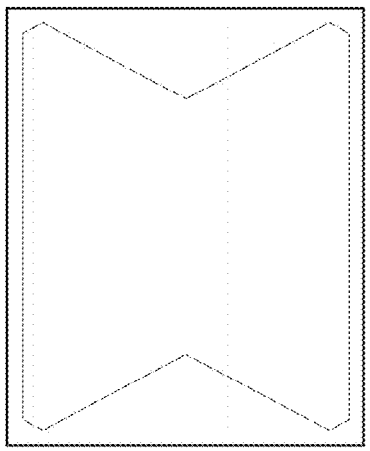
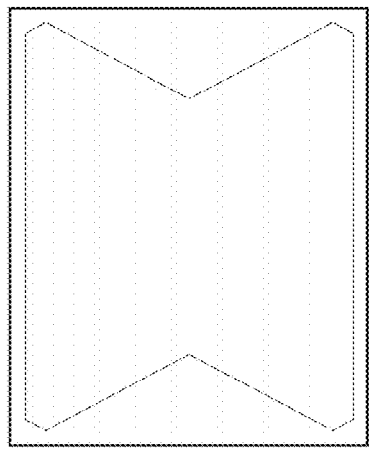
If Bonded, Cut bonded lamination stack to form blanks
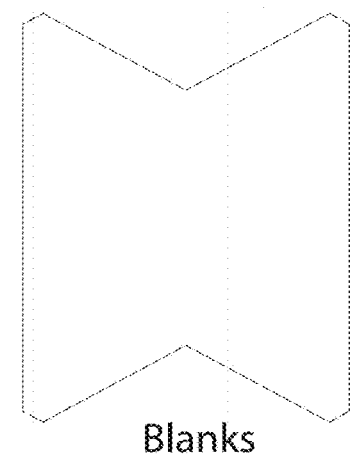
Blanks
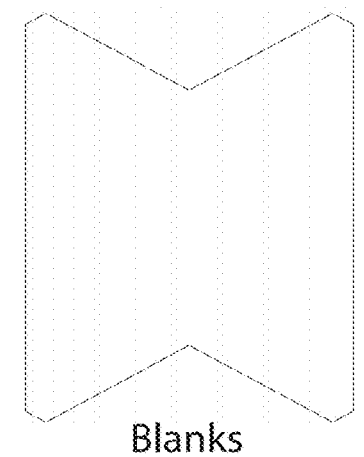
Blanks
Figure 34

Silver Fabric  Hotmelt Adhesive
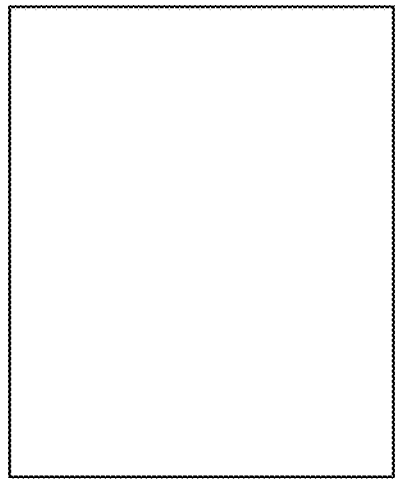 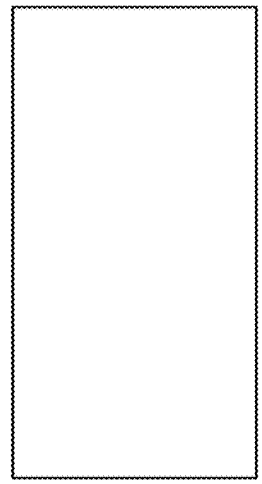
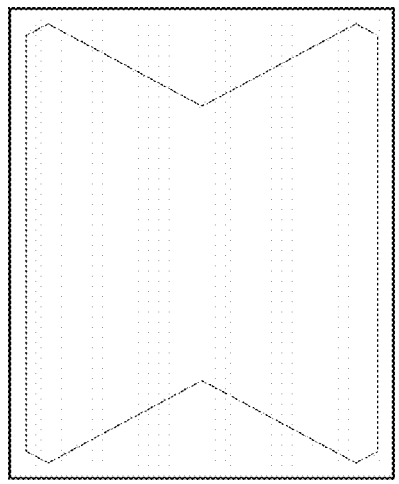 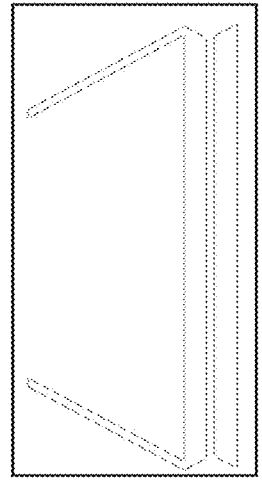
Cut stretchable hotmelt adhesive
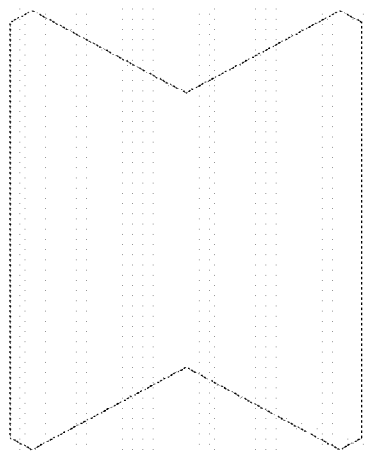 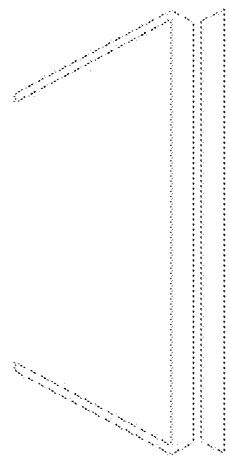
Figure 35

Fold, Press, Fold to form completed mask portion

Attach EBC Tester to Inside of Mask

Turn in-side out

Heat press on elastic straps to complete face mask conventional bendable metal nose seal replaceable adhesive removable mangentic seal-in place

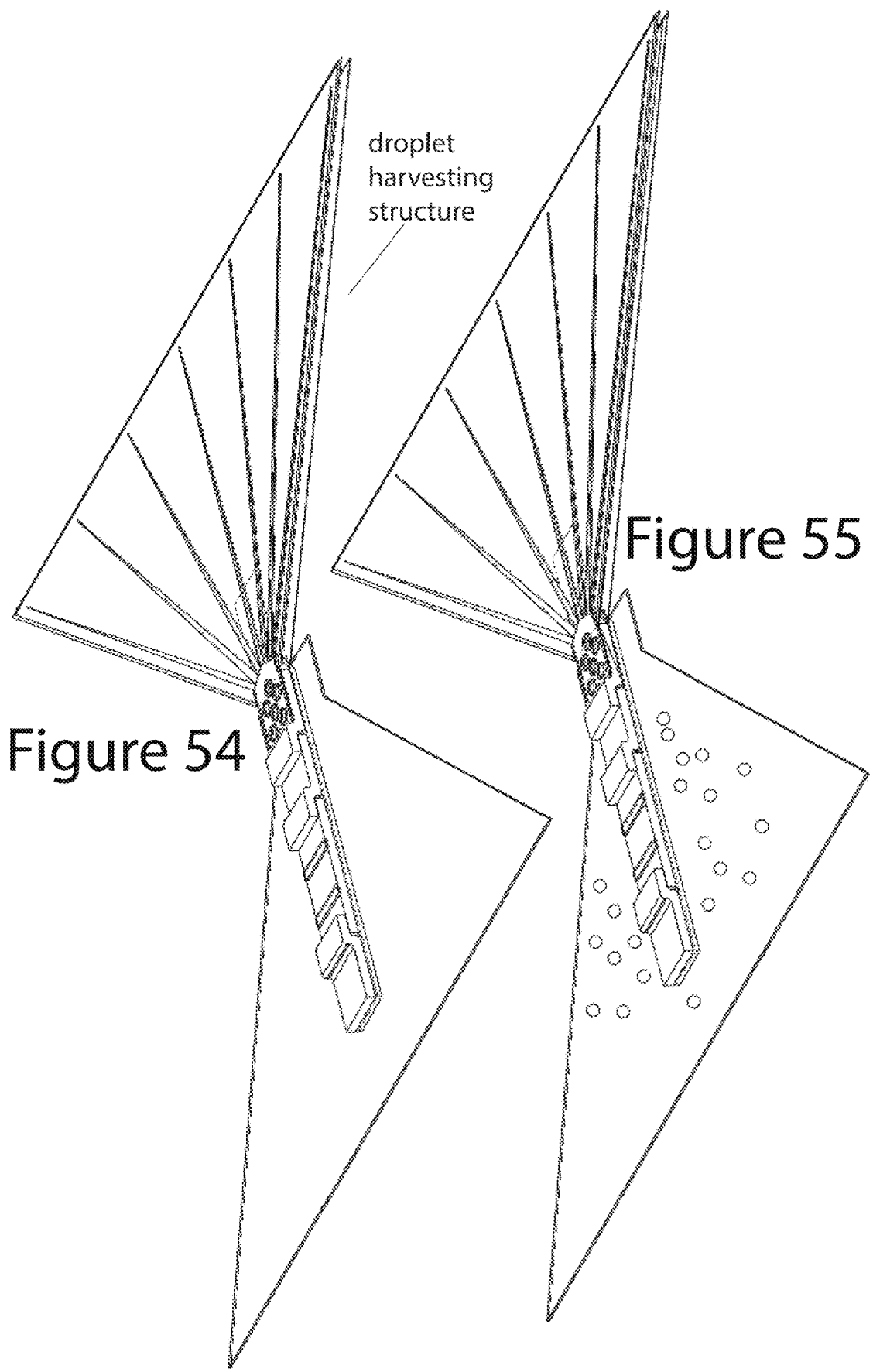

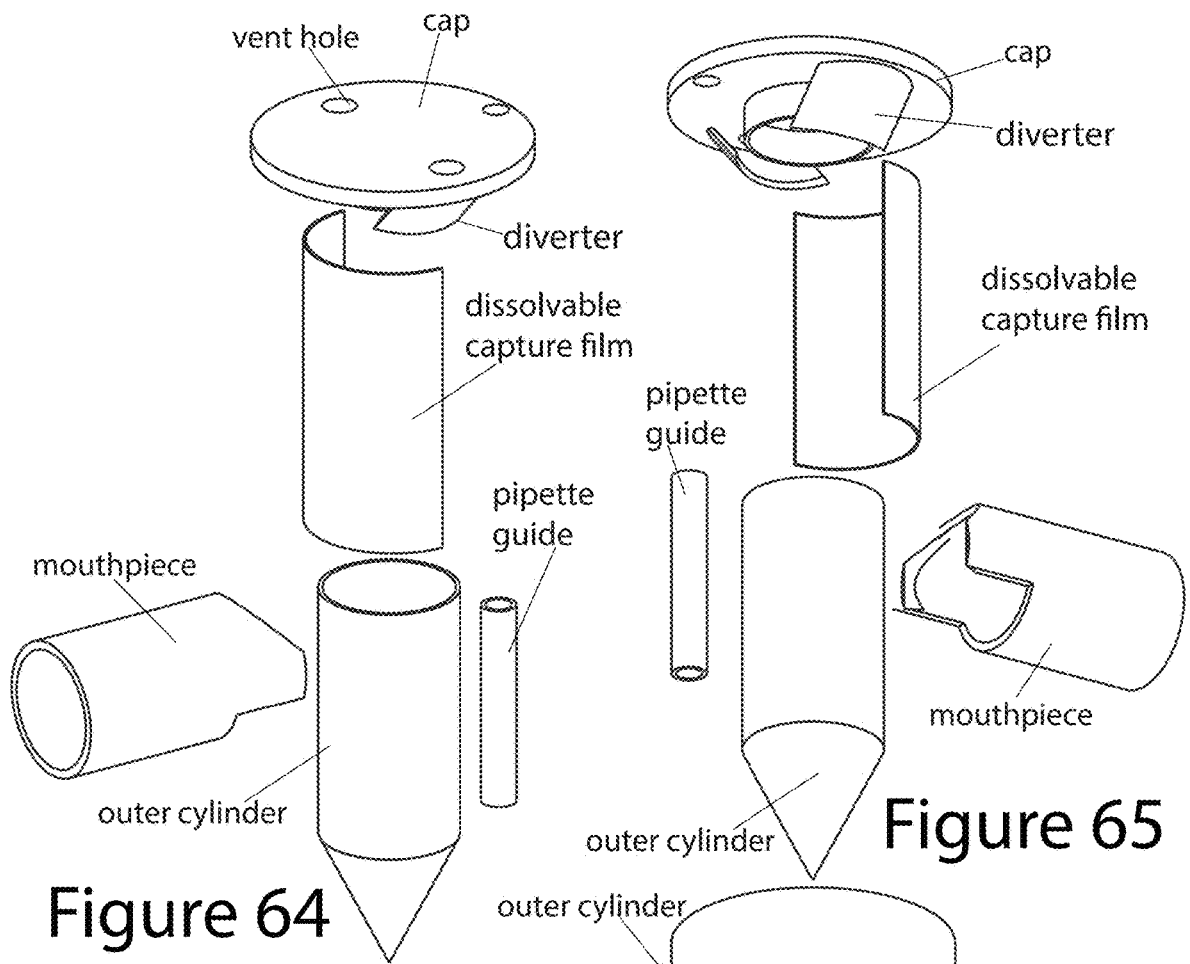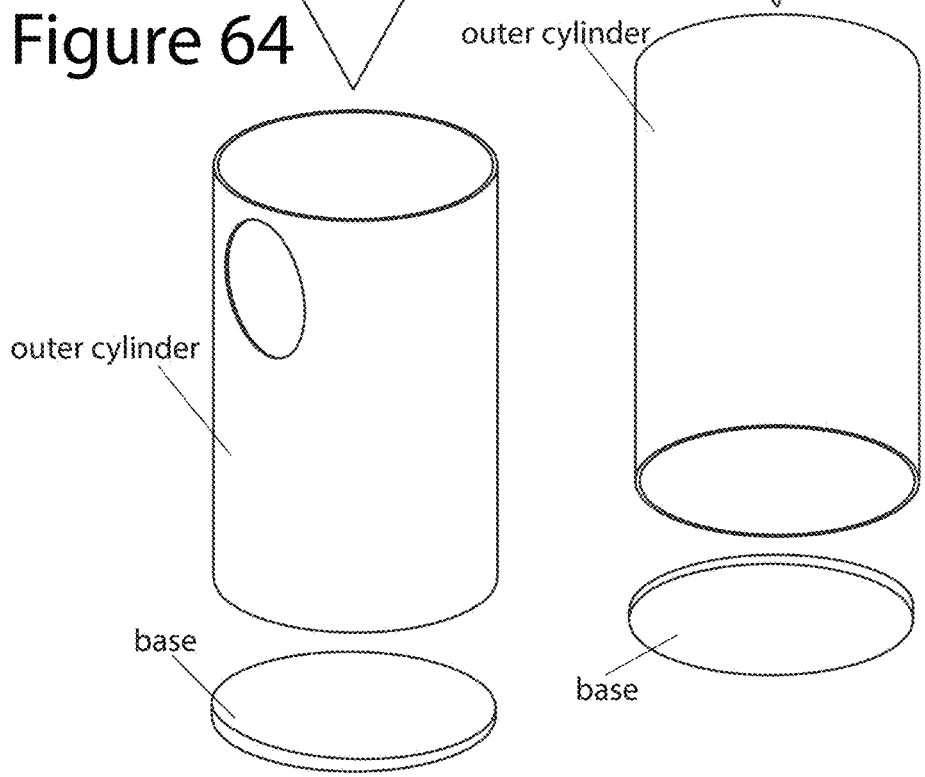

Figure 68

Figure 69
- inner cylinder
- thermal mass portion
- particulate capturing structure
- particulate
- droplet harvesting structure
- EBC droplets Figure 70
- dissolved capture film in solution with analyte aerosol particulate testing system

Figure 71

- target analyte
- aerosol droplet
- dissolvable capture film
- insoluble test area

Figure 72

- dissolvable capture film
- aerosol droplet
- target analyte
- analyte-labeled antibody complex
- flow of dissolved capture film
- labeled antibody
- insoluble test area
- binding
- analyte conjugated primary antibody (1) (2) (3) (4)

USING EXHALED BREATH CONDENSATE, AEROSOLS AND GASES FOR DETECTING BIOMARKERS

RELATED APPLICATIONS

This application relates to US Utility Patent Application Titled: Using Exhaled Breath Condensate for Testing for a Biomarker of COVID-19, Ser. No. 16/876,054, filed 17 May 2020, and claims priority of US Provisional Applications Titled: A Low Cost, Scalable, Accurate, and Easy-to-Use Testing System for COVID-19, Ser. No. 63/012,247 filed 19 Apr. 2020; Using Exhaled Breath Condensate for Testing for a Biomarker of COVID-19, Ser. No. 63/019,378 filed 3 May 2020; and Using Exhaled Breath Condensate for Testing for a Biomarker of COVID-19, Ser. No. 63/026,052 filed 17 May 2020; the disclosures of which are herein incorporated by reference in their entireties.

TECHNICAL FIELD

The exemplary and non-limiting embodiments of this invention relate generally to digital therapeutic systems, methods, devices and computer programs and, more specifically, relate to digital therapeutic wearable electronic garments for detecting a biomarker of a biological agent such as a coronavirus.

The present invention also pertains to a device architecture, specific-use applications, and computer algorithms used with wearable electronics with the capability to detect biometric parameters for the treatment and monitoring of physiological conditions in humans and animals.

BACKGROUND

This section is intended to provide a background or context to the exemplary embodiments of the invention as recited in the claims. The description herein may include concepts that could be pursued but are not necessarily ones that have been previously conceived, implemented or described. Therefore, unless otherwise indicated herein, what is described in this section is not prior art to the description and claims in this application and is not admitted to be prior art by inclusion in this section.

Governments around the world have instituted stay at home policies and the lockdown of citizens to slow the spread of the COVID-19 virus. There are currently billions of people around the world that have halted their usual employment, entertainment and socializing activities. Testing for biomarkers that indicate exposure, infection and recovery from COVID-19 can be used to enable a safer and more efficient restart of economic activities, while minimizing the spread of the virus. For example, RNA testing for active virus shows who is currently contagious. Antibody testing can be used to find the members of a population that have recovered from the virus and now may be immune to reinfection. This knowledge could enable precision social distancing and more effective contact tracing, with the re-employment of a growing workforce of protected individuals and consumers. Those who remain at-risk of infection and transmission can be kept sequestered until a vaccine or other solution such as a high success rate pharmaceutical therapy is developed.

In immunochromagtography, a capture antibody is disposed onto a surface of a porous membrane, and a sample passes along the membrane. Analyte in the sample is bound by the antibody which is coupled to a detector reagent. As the sample passes through the area where the capture antibody is disposed, an analyte detector reagent complex is trapped, and a color develops that is proportional to the analyte present in the sample.

In a lateral flow assay, a liquid sample containing a target analyte(s) flows through a multi-zone transfer medium through capillary action. The zones are typically made of polymeric strips enabling molecules attached to the strips to interact with the target analyte. Usually, overlapping membranes are mounted on a backing card to improve stability and handling. The sample containing the target analyte and other constituents is ultimately received at an adsorbent sample pad which promotes wicking of the fluid sample through the multi-zone transfer medium.

The fluid sample is first received at a sample pad which may have buffer salts and surfactants disposed on or impregnated into it to improve the flow of the fluid sample and the interaction of the target analyte with the various parts of the detection system. This ensures that the target analyte will bind to capture reagents as the fluid sample flows through the membranes. The treated sample migrates from the sample pad through a conjugate release pad. The conjugate release pad contains labeled antibodies that are specific to the target analyte and are conjugated to colored or fluorescent indicator particles. The indicator particles are typically, colloidal gold or latex microspheres.

At the conjugate release pad, the labeled antibodies, indicator particles and target analyte bind to form a target analyte-labeled antibody complex. If an analyte is present, the fluid sample now contains the indicator particles conjugated to the labeled antibody and bound to the target analyte (i.e., the target analyte-labeled antibody complex) along with separate labeled antibodies conjugated to the indicator particles that have not been bound to the target analyte. The fluid sample migrates along the strip into a detection zone.

The detection zone is typically a nitrocellulose porous membrane and has specific biological components (usually antibodies or antigens) disposed on or impregnated in it forming a test line zone(s) and control line zone. The biological components react with the target analyte-labeled antibody complex. For example, the target analyte-labeled antibody complex will bind to a specifically selected primary antibody that is disposed at the test line through competitive binding. This results in colored or fluorescent indicator particles accumulating at the test line zone making a detectable test line that indicates the target analyte is present in the fluid sample.

The primary antibody does not bind to the separate labeled antibodies and they continue to flow along with the fluid sample. At a control line zone, a secondary antibody binds with the separate labeled antibodies conjugated to the indicator particles and thereby indicates the proper liquid flow through the strip.

The fluid sample flows through the multi-zone transfer medium of the testing device through the capillary force of the materials making up the zones. To maintain this movement, an absorbent pad is attached as the end zone of the multi-zone transfer medium. The role of the absorbent pad is to wick the excess reagents and prevent back-flow of the fluid sample.

The constituents are selected and disposed on the membranes so that if there is no target analyte present in the fluid sample, there will be no target analyte-labeled antibody complex present that flows through the test line zone. In this case there will be no accumulation of the colored or fluorescent particles and no detectable test line will form. Even if there is no analyte and thus no test line, there will still be a control line formed because the secondary antibody still binds to the separate labeled antibodies that flow along with the fluid sample.

The test and control lines may appear with different intensities and depending on the device structure and the indicator particles can be assessed by eye or using an optical or other electronic reader. Multiple analytes can be tested simultaneously under the same conditions with additional test line zones of antibodies specific to different analytes disposed in the detection zone in an array format. Also, multiple test line zones loaded with the same antibody can be used for quantitative detection of the target analyte. This is often called a 'ladder bars' assay based on the stepwise capture of colorimetric conjugate-antigen complexes by the immobilized antibody on each successive line. The number of lines appearing on the strip is directly proportional to the concentration of the target analyte.

What is needed now is a low cost, scalable, accurate and easy-to-use testing system that can be deployed to the masses via the mail or courier for at-home use.

SUMMARY

The below summary section is intended to be merely exemplary and non-limiting. The foregoing and other problems are overcome, and other advantages are realized, by the use of the exemplary embodiments of this invention.

In accordance with an aspect of the invention, an apparatus for detecting a biomarker includes a particulate capturing structure for receiving and capturing exhaled breath aerosol (EBA) particulate from airway linings of a user, the particulate capturing structure having an aerosol particulate testing system for receiving the captured particulate and detecting a first biomarker, wherein the aerosol particulate testing system includes a dissolvable EBA sample collector film for capturing EBA particulate. The dissolvable EBA sample collector film includes a first reagent for reacting with at least one constituent of the captured particulate in a detection reaction for detecting the first biomarker. The detection reaction generates at least one of a change in an optical signal and an electrical signal dependent on the first biomarker. The first reagent is bound to a first nanoparticle and held in place at the insoluble testing area. The EBA particulate includes non-soluble particulates and droplet particulates, and the dissolvable EBA collector film includes a tacky surface for adhering to and capturing the non-soluble particulates and water soluble bulk for capturing droplet particulates.

In accordance with another aspect of the invention an apparatus comprises at least one processor, at least one memory including computer program code, the at least one memory and the computer program code configured to, with the at least one processor, cause the apparatus to perform at least the following: detecting one or more biometric parameters using a particulate capturing structure for receiving and capturing exhaled breath aerosol (EBA) particulate from airway linings of a user, the particulate capturing structure having an aerosol particulate testing system for receiving the captured particulate and detecting a first biomarker, wherein the aerosol particulate testing system includes a dissolvable EBA sample collector film for capturing EBA particulate, where the biometric parameters are biomarkers dependent on at least one physiological change to a patient in response to a concerning condition such as a virus infection; receiving the one or more biometric parameters and applying probabilistic analysis to determine if at least one physiological change threshold has been exceeded dependent on the probabilistic analysis of the one ore more biometric parameters; and activating an action depending on the determined exceeded said at least one physiological change. The one or more biometric parameters can be further detected using a droplet harvesting structure for converting breath vapor to a fluid droplet for forming a fluid sample and a testing system having a biomarker testing zone for receiving the fluid sample and detecting the biometric parameter; and wherein the probabilistic analysis is applied to the one or more biometric parameters to determine if the at least one physiological change threshold has been exceeded dependent on the probabilistic analysis of the one ore more biometric parameters detected from both the captured particulates and the fluid sample.

BRIEF DESCRIPTION OF THE DRAWINGS

The foregoing and other aspects of exemplary embodiments of this invention are made more evident in the following Detailed Description, when read in conjunction with the attached Drawing Figures, wherein:

FIG. 23 shows the top view of the steps for building up an LFA testing system;

FIG. 34 shows the fabric, filter and other layers bonded through a roll-to-roll lamination processor individually cut into blanks for forming a pre-form mask stack;

FIG. 35 shows other materials such as biological reactive silver fabric and hot melt adhesive of the pre-form mask stack;

FIG. 49 is an isolated view showing a dissolvable EBC droplet and EBA particulate collector;

FIG. 50 is a cross section side view showing a section of the dissolvable droplet and particulate collector having particulate and droplets impinged on the surface;

FIG. 51 is a cross section side view showing the section of the dissolvable droplet and particulate collector having particulate embedded into the dissolvable capture film and droplets dissolved into and causing a detection reaction with a detection reagent of the dissolvable capture film;

FIG. 54 is a top view showing the inventive testing system including a dissolvable EBC droplet and EBA particulate collector before capturing aerosol droplets and aerosol particulate;

FIG. 55 is a top view showing the inventive testing system including a dissolvable EBC droplet and EBA particulate collector after capturing aerosol droplets and aerosol particulate;

FIG. 56 is a top view showing the inventive testing system including a dissolvable EBC droplet and EBA particulate collector installed onto a face mask substrate along with a plurality of gas sensors for detecting volatile and gas constituents of the exhaled breath and/or ambient atmosphere;

FIG. 57 is a cross section side view showing a section of the dissolvable droplet and particulate collector having particulate and droplets impinged on the surface placed in a beaker of dissolving liquid;

FIG. 58 is a cross section side view showing a section of the dissolvable droplet and particulate collector having the particulate released into and the droplets dissolved into the beaker of dissolving liquid;

FIG. 64 is an exploded view showing the constituent parts of the embodiment of the EBC/EBA collection system;

FIG. 65 is another exploded view showing the constituent parts of the EBC/EBA collection system;

FIG. 68 is an isolated view showing the mouthpiece, cap, base, dissolvable EBA sample collector and inner cylinder of the embodiment of the EBC/EBA collection system;

FIG. 69 is an isolated view showing the dissolvable EBA sample collector and inner cylinder having captured EBA particles and droplets;

FIG. 70 shows the inner cylinder submersed in a solvent for dissolving the dissolvable EBA sample collector to acquire the captured EBA particles and droplets for biomarker testing;

FIG. 71 is an isolated view of a section of an embodiment of the dissolvable EBA sample collector forming an aerosol particulate testing system having captured EBA particulate, insoluble testing areas and dissolvable capture film areas; and FIG. 72 shows a series of side views of the embodiment of the dissolvable EBS sample collector capturing EBA droplets and/or particulate showing the aerosol particulate testing system with target analytes captured and bound to the insoluble testing areas;

DETAILED DESCRIPTION

Figure 1:
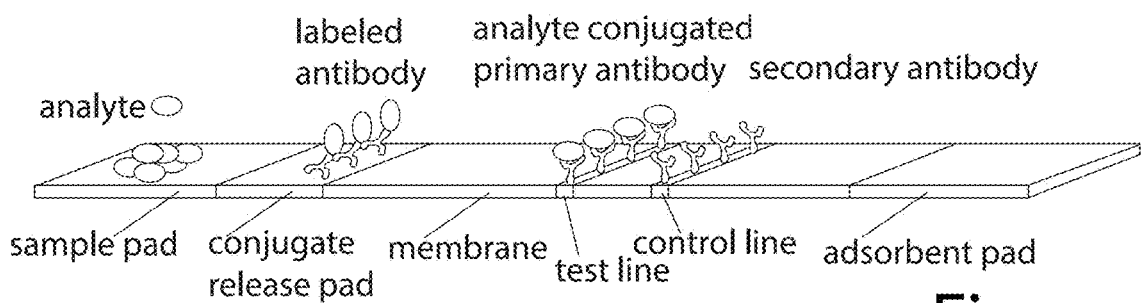
FIG. 1 shows a Lateral Flow Assay (LFA) testing system showing an analyte sample added to a sample pad.

Below are provided further descriptions of various non-limiting, exemplary embodiments. The exemplary embodiments of the invention, such as those described immediately below, may be implemented, practiced or utilized in any combination (e.g., any combination that is suitable, practicable and/or feasible) and are not limited only to those combinations described herein and/or included in the appended claims.

The word "exemplary" is used herein to mean "serving as an example, instance, or illustration." Any embodiment described herein as "exemplary" is not necessarily to be construed as preferred or advantageous over other embodiments. All of the embodiments described in this Detailed Description are exemplary embodiments provided to enable persons skilled in the art to make or use the invention and not to limit the scope of the invention which is defined by the claims.

Many configurations, embodiments, methods of manufacture, algorithms, electronic circuits, microprocessor, memory and computer software product combinations, networking strategies, database structures and uses, and other aspects are disclosed herein for a wearable electronic digital therapeutic device and system that has a number of medical and non-medical uses.

Researchers have been able to detect biomarkers in the breath of patients that have interstitial lung disease (see, Hayton, C.,Terrington, D.,Wilson, A.M.et al. Breath biomarkers in idiopathic pulmonary fibrosis:a systematic review. Respir Res 20, 7 (2019). An embodiment of the inventive testing system detects COVID-19 specific biomarkers present in the breath of infected, infectious or post-recovery individuals.

The inventive COVID-19 testing system has the ability to coalesce breath vapor into droplets and then pass the droplet sample over a fluidic biosensor, such as a Lateral Flow Assay (LFA) or Nanoscale-Bioreceptor (NS-BR) to enable a very low cost, manufacturable at-scale testing system that can be distributed to the masses for at-home triage testing. The inventive testing system can also be used for other biometric and environmental testing applications other than for virus detection.

LFAs can be used for the detection of a wide range of biomarkers present in the breath including cytokines, proteins, haptens (elicit the production of antibodies), nucleic acids and amplicons (pieces of RNA and DNA) (SEE, Corstjens P L, de Dood C J, van der Ploeg-van Schip J J, et al. Lateral flow assay for simultaneous detection of cellular- and humoral immune responses. *Clin Biochem.* 2011; 44(14-15):1241-1246. doi:10.1016/j.clinbiochem.2011.06.983).

The NSF Center for High-Rate Nanomanufacturing (CHN) has a directed assembly technique for high throughput manufacturing of NS-BRs. The technique is proven to selectively assemble nanoparticles coated with specific antibodies onto a single microchip surface for the simultaneous detection of multiple biomarkers. Early results suggested sensitivity to concentrations of much less than 1 ng/mL—a large increase in sensitivity relative to that of the commercially available ELISA detection kit. The CHN biosensor is very small, about 0.25 mm in diameter, and has advantages compared to traditional in vitro techniques because it enables disease markers detection with less false positives with a very low detection limit. This capability will be very useful for detecting very small changes in biomarker concentration in disease monitoring (see, Highly sensitive microscale in vivo sensor enabled by electrophoretic assembly of nanoparticles for multiple biomarker detection, Malima et al., *Lab Chip,* 2012, 12, 4748-4754).

Exhaled breath collection has long been recognized as requiring the least invasive methods, and so is preferred for environmental and public health studies. In contrast to blood and urine, breath sampling does not require trained medical personnel or privacy, does not create potentially infectious wastes, and can be done essentially anywhere in any time frame. Although the Exhaled Breath Condensate (EBC) format discriminates against most non-polar VOCs, it has the advantage of collecting polar compounds and heavier analytes including semi- and non-volatile organics, cytokines, proteins, cellular fragments, DNA, and bacteria. Exhaled breath also contains tiny aerosols (including both liquid and solid particles) that are created by surface film disruption at the alveolar level and by upper airway turbulence. These aerosols give mobility to materials that are otherwise relegated to the liquid layers within the lung and, as such, are that part of the EBC which contributes the non-volatile analytes. Exhaled Breath Aerosols (EBA) impacts surfaces forming a layer; only the residues are subsequently harvested using various wiping or extraction techniques. Sampling is simplified as the subject only wears a mask for some period of time. This could be either a surgical-style mask for public health monitoring, or a standard mask used for occupational respiratory protection (FIG. 1). The elegance of the technique is that only dried residues are transported to the lab; there are no special requirements for shipping (see, Pleil J D, Wallace M A G, Madden M C. Exhaled breath aerosol (EBA): the simplest non-invasive medium for public health and occupational exposure biomonitoring. *J Breath Res*. 2018; 12(2):027110. Published 2018 Feb. 6. doi:10.1088/1752-7163/aa9855).

The usual methods for obtaining clinical specimens from the respiratory tract are nasopharyngeal or oropharyngeal swabs, nasopharyngeal aspirates and nasal washes, tracheal aspirates, bronchoalveolar lavage, or the collection of sputum. Each of these techniques has drawbacks: Nasopharyngeal and oropharyngeal swabs, aspirates, and washes provide mucus from the upper respiratory tract, which does not always contain the same viral load or the same species of viruses as the lower respiratory tract. The collection of aerosol particles produced by patients during coughing and tidal breathing potentially provides a non-invasive method for the collection of diagnostic specimens of respiratory viruses. Respiratory viruses have been detected in the exhaled breath and cough aerosols from infected patients, especially influenza virus. Microbial aerosols may also be more representative of lower respiratory tract disease in viral illnesses in which sputum production is not common. Because exhaled aerosol collection is non-invasive, repeated sample collection should be more acceptable to patients than traditional methods. If the limitations can be overcome, exhaled aerosol analysis could become a useful tool for the diagnosis of respiratory infections and for monitoring the course of illness and response to treatment (see, Fennelly K P, Acuna-Villaorduna C, Jones-Lopez E, Lindsley W G, Milton D K. Microbial Aerosols: New Diagnostic Specimens for Pulmonary Infections. *Chest*. 2020; 157(3):540-546. doi:10.1016/j.chest.2019.10.012).

Usually, a thermoelectric cooling module is required to collect sufficient EBC volume for analyses but researchers have shown the feasibility of cytokine and chemokine detection in EBC collected directly from the ventilator circuit without the use of a cooling module from swivel-derived exhaled breath condensate (SEBC). SEBC was collected from the swivel adapter in a ventilator and cytokines and chemokines in SEBC was detected with a multiplex immunoassay. Twenty-nine SEBC samples were obtained from 13 ICU patients. IL-1β, IL-4, IL-8, and IL-17 were detected in more than 90% of SEBC samples, and significant correlations between multiple cytokines and chemokines were found. Several significant correlations were found between cytokines and chemokines in SEBC and mechanical ventilation parameters and serum lactate concentrations. This pilot study showed that it is feasible to detect cytokines and chemokines in SEBC samples obtained without a cooling module (see, an der Zee P, van Walree I, Fijen J W, et al. Cytokines and Chemokines Are Detectable in Swivel-Derived Exhaled Breath Condensate (SEBC): A Pilot Study in Mechanically Ventilated Patients. *Dis Markers*. 2020; 2020:2696317. Published 2020 Jan. 11. doi: 10.1155/2020/2696317).

There are more than 2000 compounds identified in EBC (see, Montuschi P, Mores N, Trové A, Mondino C, Barnes P J. The electronic nose in respiratory medicine. Respiration. 2013; 85(1):72-84) and many of them are considered to represent sensitive biomarkers of lung diseases (see, Sapey E, editor. Bronchial Asthma: Emerging Therapeutic Strategies. Rijeka: InTech. Biomarkers present in EBC depict the processes occurring in lungs much more than those in the entire body system. Therefore, particular profiles of exhaled biomarkers can reveal information exclusively applicable to lung disease diagnoses. EBC is a biological matrix reflecting the composition of the bronchoalveolar extra-cellular lung fluid. The main advantage of EBC as of a matrix is its specificity for the respiratory tract (the liquid is not influenced by process occurring in other parts of the body) (see, Molecular Diagnostics of Pulmonary Diseases Based on Analysis of Exhaled Breath Condensate, Tereza Kačerová, Petr Novotny, Ján Boroň and Petr Kačer Submitted: Oct. 9 2016 Reviewed: Jan. 25 2018 Published: Sep. 5 2018, DOI: 10.5772/intechopen.7440).

The surfaces in all parts of the lung down to the alveoli are coated with an aqueous mucous layer that can be aerosolized and carry along a variety of non-volatile constituents. EBC and EBA are different types of breath matrices used to assess human health and disease state. EBA represents a fraction of total EBC, and is targeted to larger molecules, such as fatty acids and cytokines, as well as cellular fractions, proteins, viruses, and bacteria instead of the gas-phase. There is a wide variety of compounds, such as volatile organic compounds (VOCs), NO, $CO_2$, $NH_3$, cytokines, and hydrogen peroxide ($H_2O_2$) in exhaled breath condensate (EBC), and exhaled breath aerosol (EBA). VOCs located in fatty tissues are released to the blood and are then exchanged into the breath through the alveoli and airways in the lungs. A portion of VOCs are also retained within the respiratory tract after exposure. Thus, breath concentrations of VOCs are representative of blood concentrations, but samples can be obtained non-invasively with little discomfort to the individual (see, Wallace M A G, Pleil J D. Evolution of clinical and environmental health applications of exhaled breath research: Review of methods and instrumentation for gas-phase, condensate, and aerosols. *Anal Chim Acta*. 2018; 1024:18-38. doi:10.1016/j.aca.2018.01.069).

EBC and EBA are valuable non-invasive biological media used for the quantification of biomarkers. EBC contains exhaled water vapor, soluble gas-phase (polar) organic compounds, ionic species, plus other species including semi- and non-volatile organic compounds, proteins, cell fragments, DNA, dissolved inorganic compounds, ions, and microbiota (bacteria and viruses) dissolved in the co-collected EBA (see, inters BR, Pleil J D, Angrish M M, Stiegel M A, Risby T H, Madden M C. Standardization of the collection of exhaled breath condensate and exhaled breath aerosol using a feedback regulated sampling device. *J Breath Res*. 2017; 11(4):047107. Published 2017 Nov. 1. doi:10.1088/1752-7163/aa8bbc).

An earlier reference reports detecting influenza virus RNA in the exhaled breath of 4 (33%) subjects: three (60%) of the five patients infected with influenza A virus and one (14%) of the seven infected with influenza B virus. Although a sample of EBC may have virus RNA in less concentrations than a nasal swab, these tests did determine detectable influenza virus RNA in exhaled breath. Concentrations in exhaled breath samples ranged from 48 to 300 influenza virus RNA copies per filter on the positive samples, corresponding to exhaled breath generation rates ranging from 3.2 to 20 influenza virus RNA copies per minute. The researchers note possible explanations for not detecting influenza virus RNA in a larger proportion of subjects may be due to short sample collection times, the large heterogeneity in the virus production among infected patients and the detection limit for our qPCR method (see, Fabian P, McDevitt J J, DeHaan W H, et al. Influenza virus in human exhaled breath: an observational study. *PLoS One*. 2008; 3(7):e2691.

Published 2008 Jul. 16. doi:10.1371/journal.pone.0002691). This reference shows that nasal and throat swabs will typically have more RNA concentrations than EBC. However, the virus RNA is clearly present in EBC and a EBC testing system with enough sensitivity should be effective at detecting the virus RNA.

Electron Microscope (SEM), polymerase chain reaction (PCR) and colorimetry (VITEK 2) for bacteria and viruses show that bacteria and viruses in EBC can be rapidly collected with an observed efficiency of 100 mL EBC within 1 min (see, Xu Z, Shen F, Li X, Wu Y Chen Q, et al. (2012) Molecular and Microscopic Analysis of Bacteria and Viruses in Exhaled Breath Collected Using a Simple Impaction and Condensing Method. PLoS ONE 7(7): e41137. doi:10.1371/journal.pone.0041137).

Exhaled breath contains volatile organic compounds (VOCs), a collection of hundreds of small molecules linked to several physiological and pathophysiological processes. Analysis of exhaled breath through gas-chromatography and mass-spectrometry (GC-MS) has resulted in an accurate diagnosis of ARDS in several studies. Most identified markers are linked to lipid peroxidation. Octane is one of the few markers that was validated as a marker of ARDS and is pathophysiologically likely to be increased in ARDS (see, Bos L D J. Diagnosis of acute respiratory distress syndrome by exhaled breath analysis. *Ann Transl Med.* 2018; 6(2):33. doi:10.21037/atm.2018.01.17).

Figure 2:
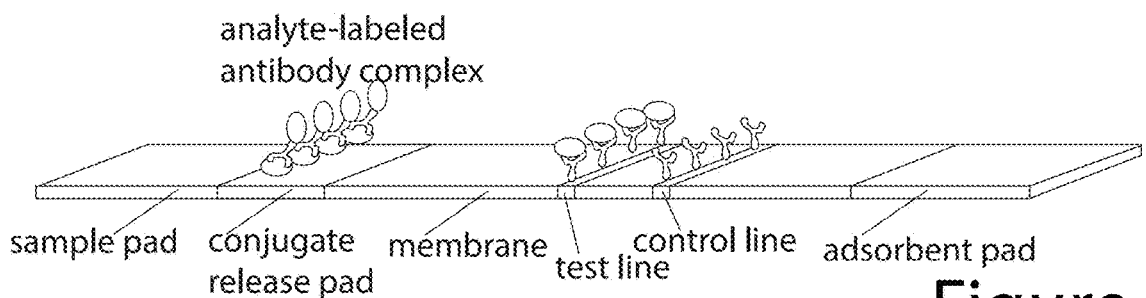
FIG. 2 shows the LFA with an analyte-labeled antibody complex formed at a conjugate release pad.
Figure 3:
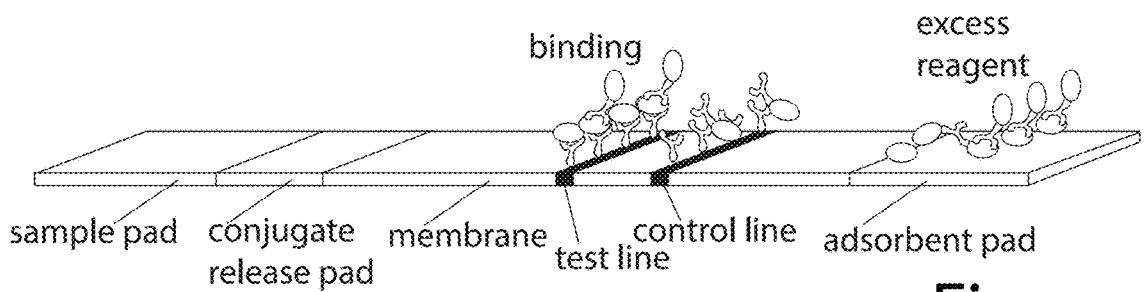
FIG. 3 shows the binding of analyte at a test line indicating the presence of the analyte.

FIG. 1 shows a Lateral Flow Assay (LFA) testing system showing an analyte sample added to a sample pad. FIG. 2 shows the LFA with an analyte-labeled antibody complex formed at a conjugate release pad. FIG. 3 shows the binding of analyte at a test line indicating the presence of the analyte. In a lateral flow assay, a liquid sample containing a target analyte(s) flows through a multi-zone transfer medium through capillary action. The zones are typically made of polymeric strips enabling molecules attached to the strips to interact with the target analyte. Usually, overlapping membranes are mounted on a backing card to improve stability and handling. The sample containing the target analyte and other constituents is ultimately received at an adsorbent sample pad which promotes wicking of the fluid sample through the multi-zone transfer medium.

The fluid sample is first received at a sample pad which may have buffer salts and surfactants disposed on or impregnated into it to improve the flow of the fluid sample and the interaction of the target analyte with the various parts of the detection system. This ensures that the target analyte will bind to capture reagents as the fluid sample flows through the membranes. The treated sample migrates from the sample pad through a conjugate release pad. The conjugate release pad contains labeled antibodies that are specific to the target analyte and are conjugated to colored or fluorescent indicator particles. The indicator particles are typically, colloidal gold or latex microspheres.

At the conjugate release pad, the labeled antibodies, indicator particles and target analyte bind to form a target analyte-labeled antibody complex. If an analyte is present, the fluid sample now contains the indicator particles conjugated to the labeled antibody and bound to the target analyte (i.e., the target analyte-labeled antibody complex) along with separate labeled antibodies conjugated to the indicator particles that have not been bound to the target analyte. The fluid sample migrates along the strip into a detection zone.

The detection zone is typically a nitrocellulose porous membrane and has specific biological components (usually antibodies or antigens) disposed on or impregnated in it forming a test line zone(s) and control line zone. The biological components react with the target analyte-labeled antibody complex. For example, the target analyte-labeled antibody complex will bind to a specifically selected primary antibody that is disposed at the test line through competitive binding. This results in colored or fluorescent indicator particles accumulating at the test line zone making a detectable test line that indicates the target analyte is present in the fluid sample.

The primary antibody does not bind to the separate labeled antibodies and they continue to flow along with the fluid sample. At a control line zone, a secondary antibody binds with the separate labeled antibodies conjugated to the indicator particles and thereby indicates the proper liquid flow through the strip.

The fluid sample flows through the multi-zone transfer medium of the testing device through the capillary force of the materials making up the zones. To maintain this movement, an absorbent pad is attached as the end zone of the multi-zone transfer medium. The role of the absorbent pad is to wick the excess reagents and prevent back-flow of the fluid sample.

The constituents are selected and disposed on the membranes so that if there is no target analyte present in the fluid sample, there will be no target analyte-labeled antibody complex present that flows through the test line zone. In this case there will be no accumulation of the colored or fluorescent particles and no detectable test line will form. Even if there is no analyte and thus no test line, there will still be a control line formed because the secondary antibody still binds to the separate labeled antibodies that flow along with the fluid sample.

The test and control lines may appear with different intensities and depending on the device structure and the indicator particles can be assessed by eye or using an optical or other electronic reader. Multiple analytes can be tested simultaneously under the same conditions with additional test line zones of antibodies specific to different analytes disposed in the detection zone in an array format. Also, multiple test line zones loaded with the same antibody can be used for quantitative detection of the target analyte. This is often called a 'ladder bars' assay based on the stepwise capture of colorimetric conjugate-antigen complexes by the immobilized antibody on each successive line. The number of lines appearing on the strip is directly proportional to the concentration of the target analyte.

Another testing system that can be used with the inventive EBC collection system uses a nano-scale bioreceptor (NS-BR). Similar to LFA, NS-BR has the potential of a much higher sensitivity and can be used to provide a direct-to-electrical signal to enable, for example, easy wireless connectivity. The inventive EBC collection system with NS-BR testing is easily deployable as a compliment to existing Contact Tracing APPs. The nanoscale dimensions mean many detectors are made at once on a single wafer for lower cost, high throughput manufacturing.

Figure 4:
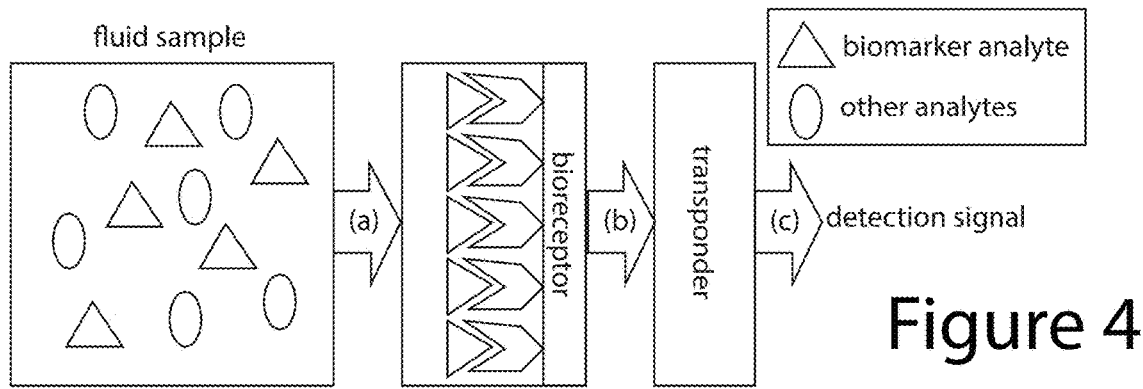
FIG. 4 shows the mechanism of a bioreceptor detection system.

FIG. 4 shows the mechanism of a bioreceptor detection system. Simplistically, the main components of a fluidic biosensor includes a sample source (a); a bioreceptor area that is functionalized with an analyte-specific bioreceptor (b); and a transducer for generating a readable signal (c). The bioreceptor is matched to a specific target biomarker for lock and key selectivity screening. A fluid sample with some concentration of the target biomarker analyte (possibly as small as a single molecule) flows onto the bioreceptor field. Some of the bioreceptor "locks" receive the biomarker "keys." This causes a detectable change in the output of the transducer that transforms the bioreceptor output into a readable signal for amplification and data processing.

For example, the desired biomarker analyte can also be an antibody that indicates the recovery from a Covid-19 infection. A fluid sample can be received as a droplet of sweat or breath or other body fluid and if the target antibody is present in the sample it interacts with the analyte-specific bioreceptor. The bioreceptor outputs a signal with defined sensitivity and the transducer generates, for example, a change in an electrical characteristic such as conductivity, indicating the presence of the antibody biomarker in the fluid sample.

In accordance with an embodiment, an apparatus for detecting a biomarker comprises a droplet harvesting and channeling structure for converting vapor to a fluid droplet and a fluidic biosensor including a sample source having a biomarker analyte, a bioreceptor area functionalized with an analyte-specific bioreceptor, and a transducer for generating a readable signal depending on a change in the bioreceptor in response to receiving the biomarker analyte from the sample source.

Using nano-scale sensor technology enables detection of very low concentrations of the target analyte(s) such as virus RNA and/or antibodies while avoiding the need for drawing blood. In accordance with an embodiment of the inventive testing system, a droplet harvesting and channeling mechanism uses a hydrophobic field for fluid harvesting and hydrophilic channels for droplet movement onto the nanosensor. This mechanism makes the inventive system practical for creating a very inexpensive, scalable manufacturable COVID-19 test that does not require any blood or the administration of the test by a skilled technician, nurse or healthcare provider.

An embodiment uses a nano-scale fluidic biosensor technology with a unique moisture droplet harvesting and channeling structure. This structure unlocks the use of the nano-scale sensor for detection possibly down to single molecules of target biomarkers. This enables the detection of even very low concentrations of antibodies, proteins and other chemical biomarkers present in any body fluid without the drawing of blood.

A non-limiting embodiment builds on the sweat chemistry sensor technology described in PCT/US19/45429, METHODS AND APPARATUS FOR A WEARABLE ELECTRONIC DIGITAL THERAPEUTIC DEVICE invented by Daniels and published Apr. 10, 2020, which is incorporated by reference herein in its entirety. The embodiment is a COVID-19 testing system that can be mass produced on readily available high volume manufacturing equipment in the millions of units needed for mass population testing. An embodiment of the testing system uses a nano-scale fluidic biosensor with a unique moisture droplet harvesting and channeling structure. This structure enables the use of the nano-scale sensor for detecting COVID-19 biomarkers in a body fluid sample, such as breath condensate. This system enables the detection of analyte(s) of antibodies, proteins, RNA and other chemical COVID-19 biomarkers without the drawing of blood, expensive equipment or technically trained personnel. The proposed system can be configured as at least a first pass go/no-go test that can determine who should be more accurately tested by the conventional testing methodologies.

COVID-19 is a new disease with uncertain knowledge about how it spreads and the severity of the illness it causes. The virus is thought to spread mainly from person-to-person, between people who are in close contact with one another. Respiratory droplets produced when an infected person coughs, sneezes or talks can land in the mouths or noses of people who are nearby or possibly be inhaled into the lungs. COVID-19 can be transferred by touching a surface contaminated with the virus then touching one's eyes, nose or mouth. Recent studies suggest that COVID-19 may also be spread by people who are contagious but asymptomatic.

Mathematical models indicate that one-time lockdown interventions may not be sufficient to keep the spread of COVID-19 from overwhelming the US critical care capacity. Although seasonal variation in transmission may help slow the spread during the summer months, this could also lead to a dramatic increase in COVID-19 infections in the autumn. Researchers believe that intermittent distancing measures can maintain control of the epidemic, but without other interventions, these measures may be necessary into 2022 (see, Social distancing strategies for curbing the COVID-19 epidemic, Kissler et al. pre-peer-reviewed online release, medRxiv 2020.03.22.20041079).

Modeling studies and reports from the Wuhan outbreak indicate that even in developed countries with good healthcare infrastructure, the capacity for critical care response caused by COVID-19 infections can be exceeded many times over if distancing measures are not implemented quickly or strongly enough[1]. The modeling studies are showing that to keep critical care capacities from being overwhelmed, prolonged or intermittent social distancing may be necessary (see, Li R, Rivers C, Tan Q, Murray M, Toner E, Lipsitch M. 2020 The demand for inpatient and ICU beds for COVID-19 in the US: lessons from Chinese cities).

So in order to slow the spread of the virus, governments have instituted stay at home policies, requiring billions of people around the world to stop their usual employment, entertainment and socializing activities.

This drastic shutdown of business has been a major element in combating the COVID-19 pandemic. However, the economic fallout is becoming untenable. As of April 16, there are more than 22 million people in the US who have filed for unemployment. The financial markets are being affected around the world with unprecedented volatility, and governments are now trying to find the balance to combat the spread of the virus through country-wide lockdowns while allowing for some easing of the lockdowns to avoid possible economic collapse. A key question for government leaders is: how do we safely restart our economies?

There is a growing consensus that testing for biomarkers that indicate exposure, infection and recovery from COVID-19 should be used to enable a safer and more efficient restart to regional, national and the global economy, while minimizing the threat of an out-of-control spread of the virus. The restarting of the global economy must be done safely to prevent avoidable suffering and an exacerbation of the socioeconomic damage already caused by the pandemic. However, restarting must also be done efficiently and as soon as practical to prevent a prolonged recession and possible global depression that could take even more of a severe toll especially on poor and economically-at-risk people.

Testing for COVID-19 has become a very important tool in the arsenal for combating the virus and enabling a safe restarting of the economy. Antibody testing, in particular, could determine who in the population may now be immune to reinfection or who is still susceptible to the virus infection and a threat of infecting others. Importantly, knowing who has adequate antibody protection against Covid-19 could more safely enable the re-employment of a growing workforce of protected individuals and consumers while those who remain at risk of infection and transmission can be kept sequestered until a vaccine or other mechanism is developed.

Tools for early diagnostics, infection prevention, monitoring and control have become critical need items due to the global outbreak of the COVID-19 virus. In the past few months the world has learned a lot about the virus that is causing the current pandemic, but still there is much to learn about how to prevent exposures, identify who needs immediate treatment, and how to slow the virus spread.

Most reasonable estimates for when a vaccine might be available for widespread deployment range from 18 months to as much as two-three years. The need for mass testing for COVID-19 will last at least until there is a vaccine. Most likely even once this current pandemic is conquered the need to quickly spin up mass testing capabilities will always be part of a country's long term strategic health plan.

Even after the first surge of the virus has passed, in order to properly dimension and locate resources for the next virus wave, governments and healthcare providers need to determine who still needs to be quarantined, who currently has the active virus, and who has already recovered from the virus. Early detection mechanisms for all these cases can be used to significantly limit the virus spread and prevent overwhelming a state's or country's healthcare system.

There are several detection systems under development by companies and government agencies around the globe. These systems detect several different biomarkers indicative of the COVID-19 virus.

For example, RayBiotech of Georgia offers lateral flow devices for the detection of IgG and IgM antibodies to the coronavirus N-protein in serum, plasma, and peripheral blood. Such a lateral flow device is similar to a home pregnancy test, but requires the drawing of blood through a finger pin prick.

Other Covid-19 biomarker testing systems include a RT-PCR Nucleic Acid (Real Time) detection system that can be used for detecting a nucleocapsid protein N gene from samples taken by human throat swabs and alveolar lavage.

Measurement of human IgG antibody can be performed for COVID-19 in serum or plasma using an ELISA testing methodology. The enzyme-linked immunosorbent assay (ELISA) typically uses a solid-phase enzyme immunoassay to detect the presence of a target biomarker ligand or protein.

There are several other detectable biomarkers that can help identify exposure, incubation, infection, and post-recovery. Proteins, such as a nucleocapsid protein (N-protein) that binds to the coronavirus RNA genome creating a shell around the enclosed nucleic acid can be used as a detectable biomarker. Human ACE-2 (angiotensin-converting enzyme 2) is an integral membrane protein that serves as the initial attachment point for COVID-19 and can also be used as a detectable biomarker. To combat COVID-19 and aid in drug discovery, protein profiling can be used to understand the host response to infection and identify potential biomarkers for drug development.

During the course of the progression of the virus in the human host, changes to the immune system can also be used as detectable biomarkers. For example, during infection of COVID-19, high levels of inflammatory cytokines include interferons, interleukins, chemokines, colony-stimulating factors, and tumor necrosis factors are often detectable and contribute to the symptoms of coronavirus infection. Recent research is showing that the overproduction of pro-inflammatory cytokines can result in a "cytokine storm," where inflammation spreads throughout the body carried by the circulatory system. A common consequence of a cytokine storm is acute lung injury, which can then result in a more severe form called acute respiratory distress syndrome. Proteins and other biomarkers resulting from a cytokine storm can be used to help monitor and predict the progression of the virus.

An embodiment of the inventive COVID-19 testing system could be useful for creating a low cost, accurate, and easy-to-use testing system for some or all of these COVID-19 indicating biomarkers. Such a system has multiple utilities including contact tracing, diagnosing, disease progression monitoring and predictive machine learning population data analysis.

Blood tests and nasal swabs are now being used for testing for certain COVID-19 biomarkers. The accuracy and sensitivity of these tests is still lower than optimum, and typically require a technician or nurse with elaborate personal protection equipment to obtain the sample from the individual being tested. Then, the equipment that is used to perform the tests requires a skilled technician and is typically done serially—one sample at a time. The inventive COVID-19 testing system is a low cost, mass producible technology platform that can be configured to test for multiple COVID-19 biomarkers, and be deployed quickly for at-home testing, as well as for clinical and drug discovery use. Such a multiple biomarker testing system should have better statistical results than the single biomarker tests currently being done as the standard of care.

There is the need for a low cost, accurate, easy-to-use testing system for COVID-19 that ideally can be mailed out and self-administered at home. For example, current testing protocols require a nasal swab for RNA testing to show active infection or a sample of blood be taken from a person in order to test for sufficient antibodies to the COVID-19 virus for immunity. These tests typically require breaking sequestration and traveling to a testing site where a technician, nurse or other healthcare provider administers the test. We propose a testing system that can be used as a first pass go/no go assessment to first see if a more elaborate and expensive testing methodology is warranted. For example, an inexpensive, easy-to-use testing system that can be done at home and finds a low concentration of COVID-19 antibodies present in the breath or sweat can then be used as the impetus for the individual to go to a testing facility for a more accurate determination of the person's immunity to further COVID-19 infection.

Figure 5:
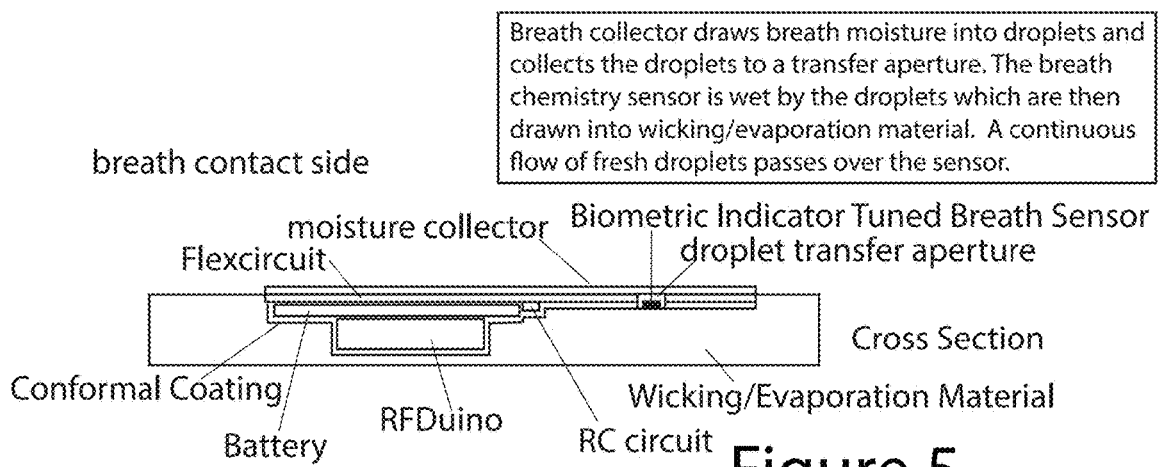
FIG. 5 is a side view of a wearable electronic breath chemistry sensor.
Figure 6:
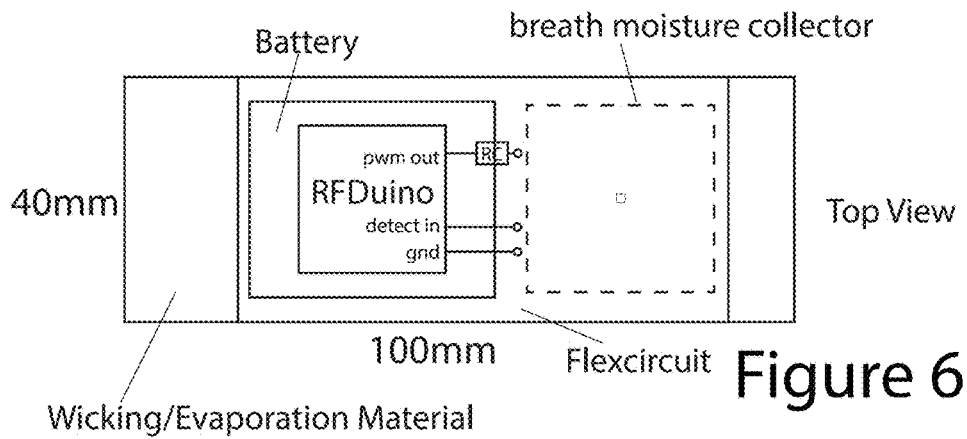
FIG. 6 is a top view of a wearable electronic breath chemistry sensor.

FIG. 5 is a side view of a wearable electronic breath chemistry sensor. FIG. 6 is a top view of a wearable electronic breath chemistry sensor. The biometric sensor is tuned to detect at least one biometric indicator associated with the presence of COVID-19 antigen, RNA and/or antibody. A droplet collector draws EBC droplets into a transfer aperture. The sensor is wet by the droplet and then the droplet is drawn through wicking into wicking/evaporation materials. A continuous flow of fresh droplets passes over the sensor. A hydrophobic field encourages sweat to bead and migrate to hydrophilic channels. Tapered hydrophilic channels use surface tension to draw sweat into the sweat transfer aperture. Hydrophobic and hydrophilic screen printable inks are available from companies such as Cytonix and Wacker.

Figure 7:
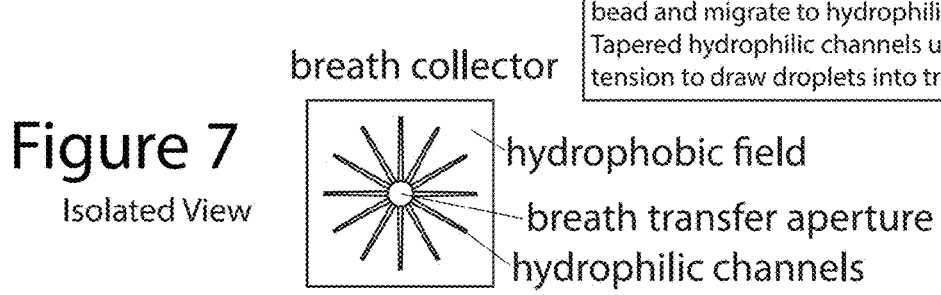
FIG. 7 is an isolated view of a Exhaled Breath Condensate (EBC) droplet sample collector.
Figure 8:
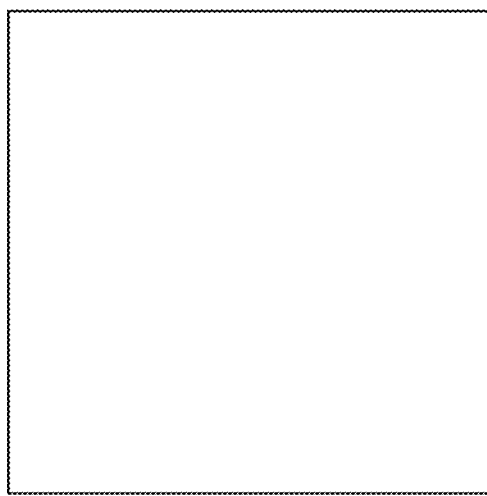
FIG. 8 is a top view showing a step for forming the EBC droplet collector.
Figure 9:
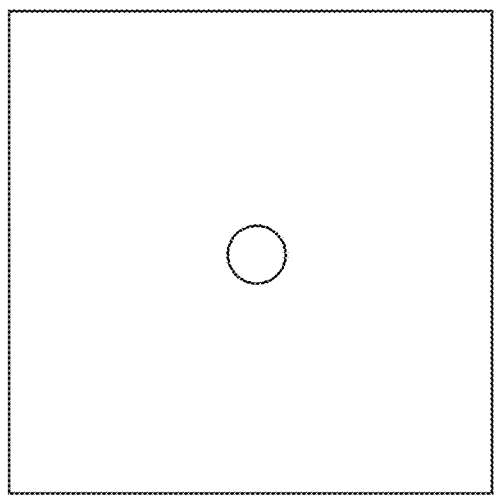
FIG. 9 is a top view showing another step for forming the EBC droplet sample collector.
Figure 10:
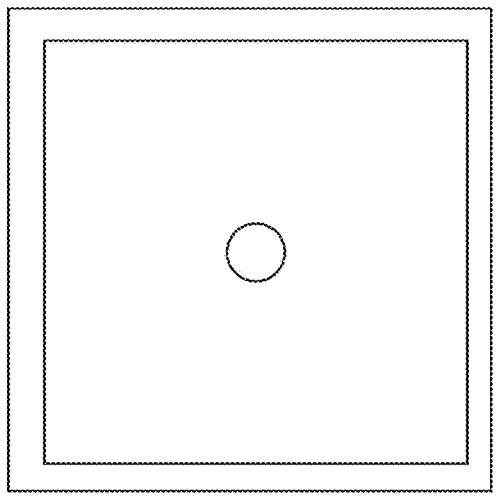
FIG. 10 is a top view showing still another step for forming the EBC droplet sample collector.
Figure 11:
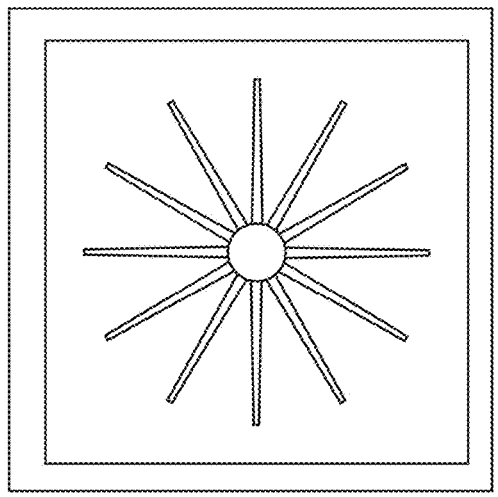
FIG. 11 is a top view showing yet another step for forming the EBC droplet sample collector.
Figure 12:
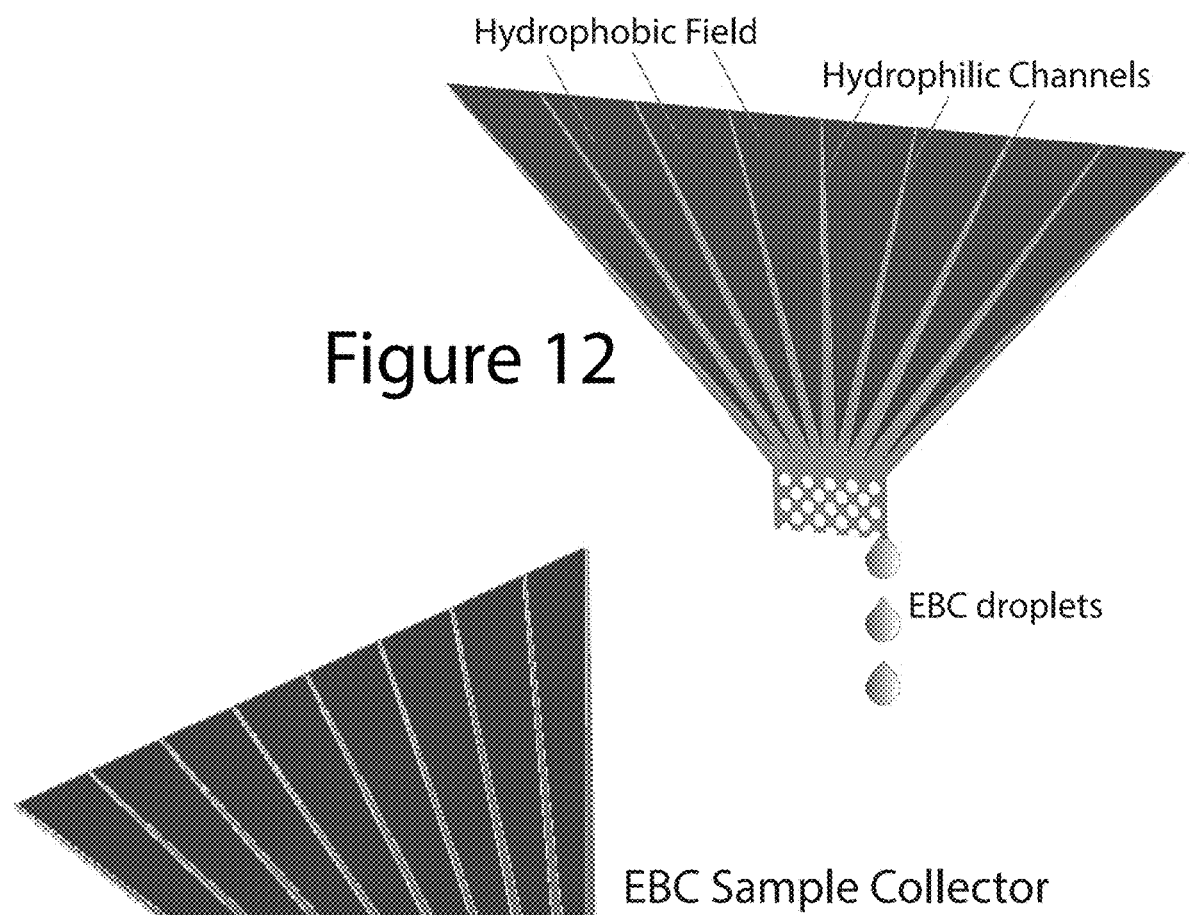
FIG. 12 illustrates the EBC sample collector showing EBS droplets.

FIG. 7 is an isolated view of an Exhaled Breath Condensate (EBC) droplet sample collector. FIG. 8 is a top view showing a step for forming the EBC droplet collector. FIG. 9 is a top view showing another step for forming the EBC droplet sample collector. FIG. 10 is a top view showing still another step for forming the EBC droplet sample collector. FIG. 11 is a top view showing yet another step for forming the EBC droplet sample collector. FIG. 12 illustrates the EBC sample collector showing EBS droplets. In accordance with a non limiting exemplary embodiment, an at-home, triage COVID-19 testing system uses Exhaled Breath Condensate (EBC) for an analyte fluid sample. Breath is an exceptional source of virus antigens, antibodies and RNA. EBC can be analyzed using establish methods including Lateral Flow Assay, Nano-scale Bioreceptor and Photonic Quantitative Assay. EBC produces much cleaner samples to test than nasal swabs, is non-invasive and easier than drawing blood. However, collecting EBC usually requires a big, expensive chiller and is always done in a clinical setting.

There is a great push throughout the world to develop adequate testing for the COVID-19 virus. A conventional PCR test detects pieces of dead virus from nasal swab or sputum. The test determines if a person is infectious. The test is expensive, requires trained personnel and machines and there is a delay in obtaining the test results due to collection, transportation and processing of samples. PCR also requires a lot of chemical and results in a lot of false negatives. Antibody test detects the body's immune response to the virus. It requires a blood sample. Antibody tests can be relatively fast and does necessarily require trained personnel. False positives are frequent because other viruses could be causing the antibodies.

EBC has been used for rapid detection of microbial DNA and RNA to demonstrate bacterial and viral lung infections. (see, Xu Z, Shen F, Li X, Wu Y, Chen Q, Jie X, et al. Molecular and microscopic analysis of bacteria and viruses in exhaled breath collected using a simple impaction and condensing method.PLOS One 2012; 7:e41137).

A nasal swab sample often contains a lot of background biological materials making it harder to identify the RNA of the virus because of other molecules present in the sample.Breath condensate is naturally enriched with viruses and confounding molecules are at much lower concentrations.

Antibodies are present in breath vapor. IgA antibodies are found in areas of the body such the nose and breathing passages. IgG antibodies are found in all body fluids and are the most common antibody (75% to 80%), that are very important in fighting bacterial and viral infections.IgE antibodies are found in the lungs, skin, and mucous membranes.

Virus Antigens are found in Airway Lining Fluid (ALF). EBC is a non-invasive method of sampling airway lining fluid (ALF). Constituents of ALF are representative of the respiratory tree lining fluids. ALF is a measure of the concentration of biomarkers directly influenced by respiratory cells. (see, *Exhaled breath condensate: a comprehensive update*, Ahmadzai, et al., Clinical Chemistry and Laboratory Medicine (CCLM) 51, 7; 10.1515/cclm-2012-0593).

Although EBC could be an exceptional source of biomarkers indicating the stages of infection and recovery from the COVID-19 virus, as well as other medical and fitness uses, the conventional equipment for obtaining an EBC fluid sample is big and expensive, and is only used in clinical setting. The conventional equipment requires a chiller and is designed for relatively large sample collection. This makes conventional EBC sampling equipment unsuited for at-home testing.

An embodiment of the inventive EBC sample collector includes a hydrophobic field that causes vapor to bead up into droplets. Hydrophilic channels coalesce and transfer the droplets to form an accessible EBC fluid sample. The hydrophobic field and hydrophilic channel can be screen printed or otherwise coated on a thermal mass aluminum sheet substrate. This substrate can be chilled prior to using the testing system to improve EBC collection. The inventive EBC sample collector makes the low cost Lateral Flow Assay and other testing systems workable for at-home triage testing. The CDC says it is essential to quickly develop inexpensive screening test. The inventive EBC sample collector makes such screening testing viable for mass deployment to large segments of the population. There is no need to break sequestration. No skilled technicians, clinics or lab equipment are needed. Very high volume existing manufacturing methods can be modified to product multiple-up (many at once) screen printed EBC sample collectors. A low-cost aluminum substrate acts as thermal mass and can be chilled for faster droplet harvesting. Batch fabrication can be used to manufacture multiple-up LFA modules on a sheet with a format that is quickly adaptable to ultra-high-volume Roll-to-Roll manufacturing.

Figure 13:
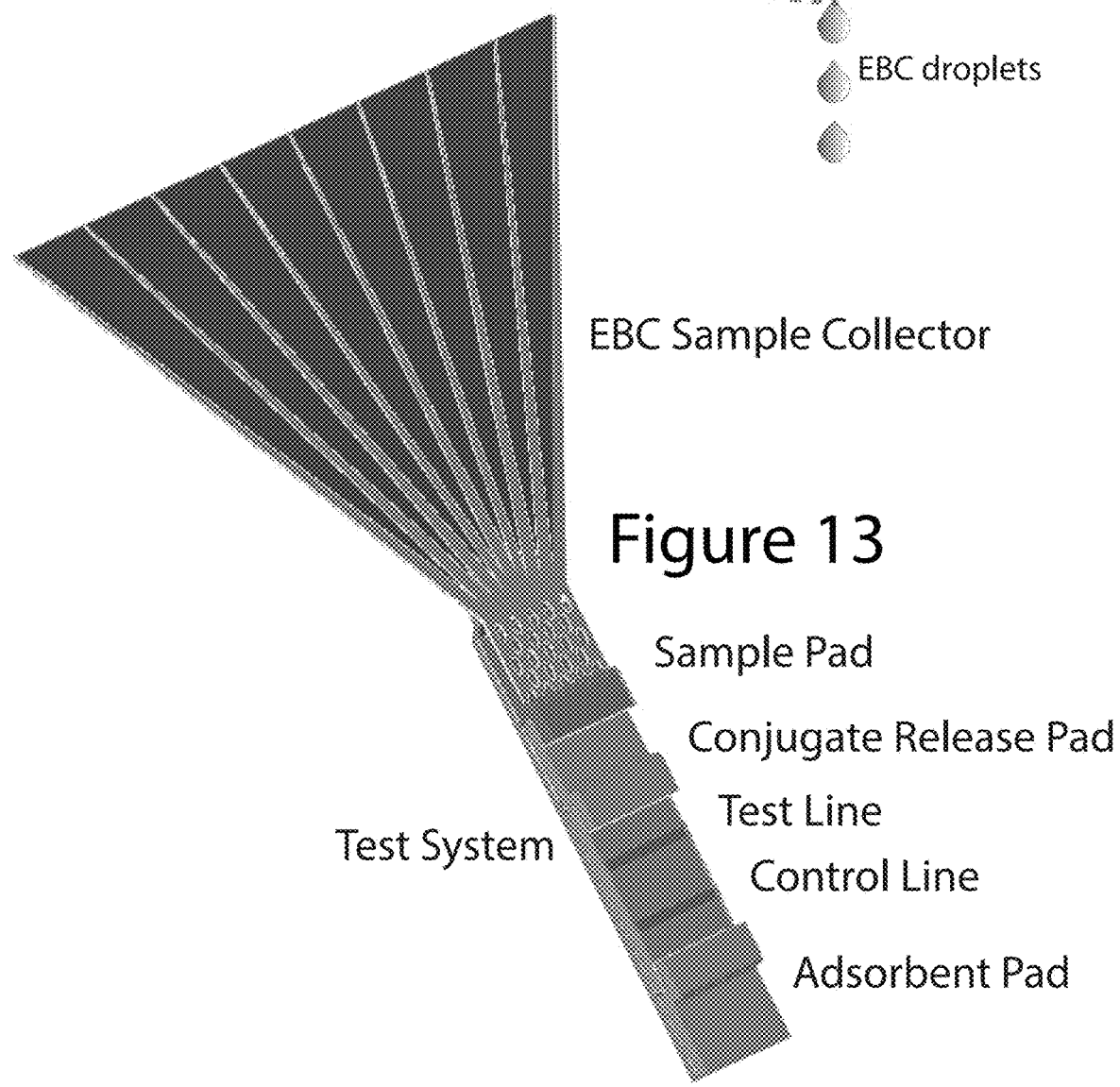
FIG. 13 illustrates the EBC sample collector applied to an LFA testing system.
Figure 14:
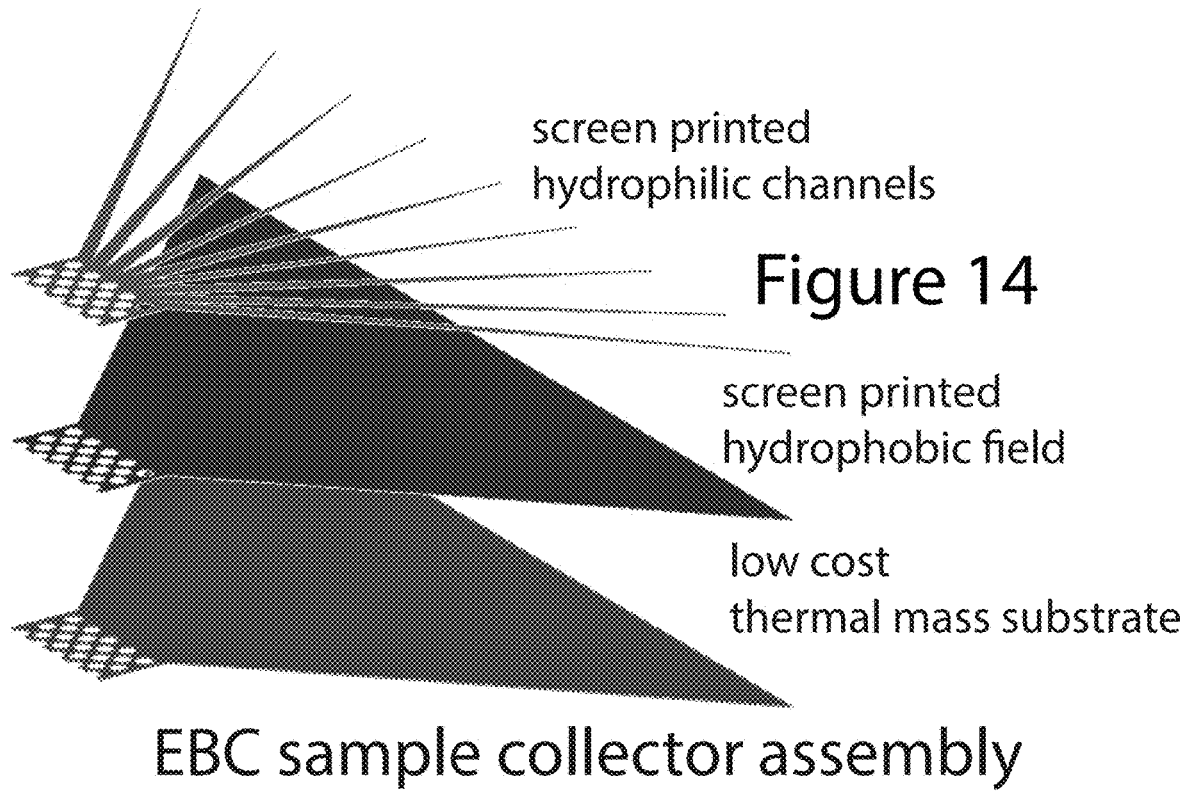
FIG. 14 is an exploded view showing the screen printed hydrophilic channels, screen printed hydrophobic field and thermal mass substrate of the EBC sample collector.

FIG. 13 illustrates the EBC sample collector applied to an LFA testing system. FIG. 14 is an exploded view showing the screen printed hydrophilic channels, screen printed hydrophobic field and thermal mass substrate of the EBC sample collector. A first emitter/detector pair are used to determine if the novel coronavirus N protein at the test line (T) has been bound by the IgM-IgM complex. A second emitter/detector pair are used to determine if free anti-human IgM antibody has been bound to the anti-mouse antibody at the control line (C) confirming that the fluid sample has transversed through the transfer medium and the test has been correctly performed.

In accordance with an embodiment, a method of forming a biomarker testing system comprising forming an exhaled breath condensate fluid sample collector. Forming the exhaled breath condensate fluid sample collector comprise the steps of providing a substrate, coating a hydrophobic field on the substrate, and coating at least one hydrophilic channel on the substrate. The hydrophobic field is for receiving body fluid vapor and forming a fluid droplet from the received body fluid vapor and hydrophilic channel is for receiving the fluid droplet and channeling the fluid droplet towards a testing system. At least one fluid sample draining hole may be formed at an end of the hydrophilic channel for draining the fluid droplet through the at least one fluid sample draining hole onto a sample receiving structure of the testing system.

Figure 15:
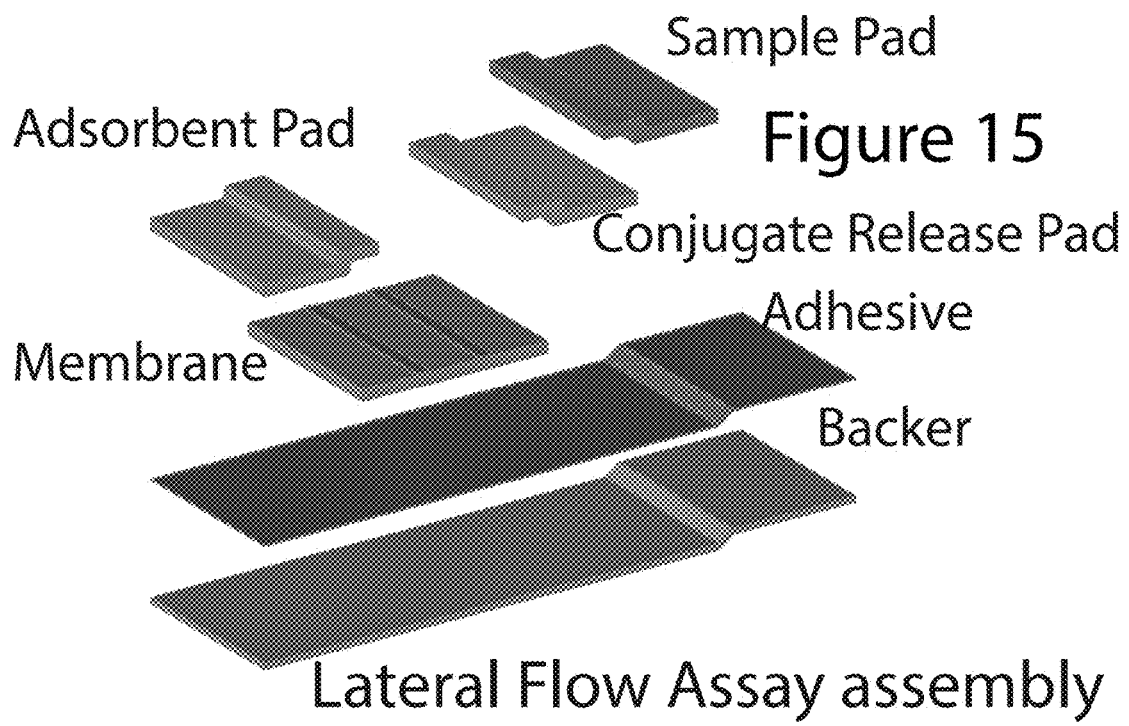
FIG. 15 is an exploded view showing the constituent elements of a LFA.
Figure 16:
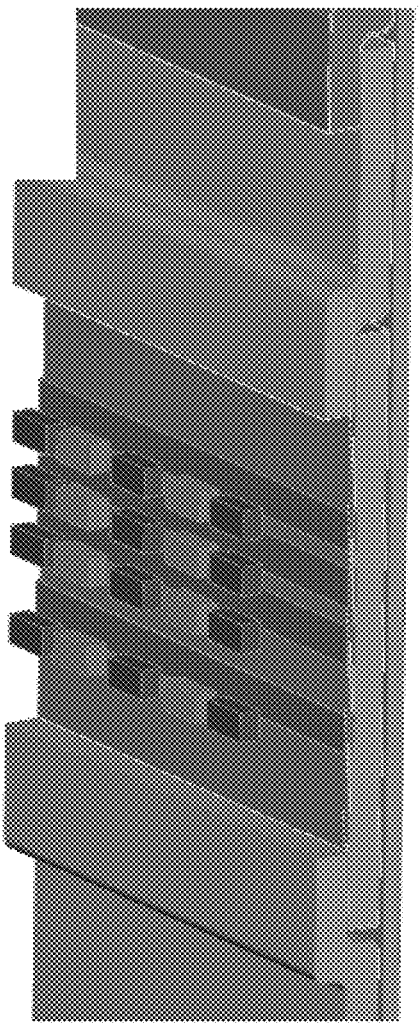
FIG. 16 illustrates an embodiment of the LFA including photonic emitter/detector electronics.
Figure 17:
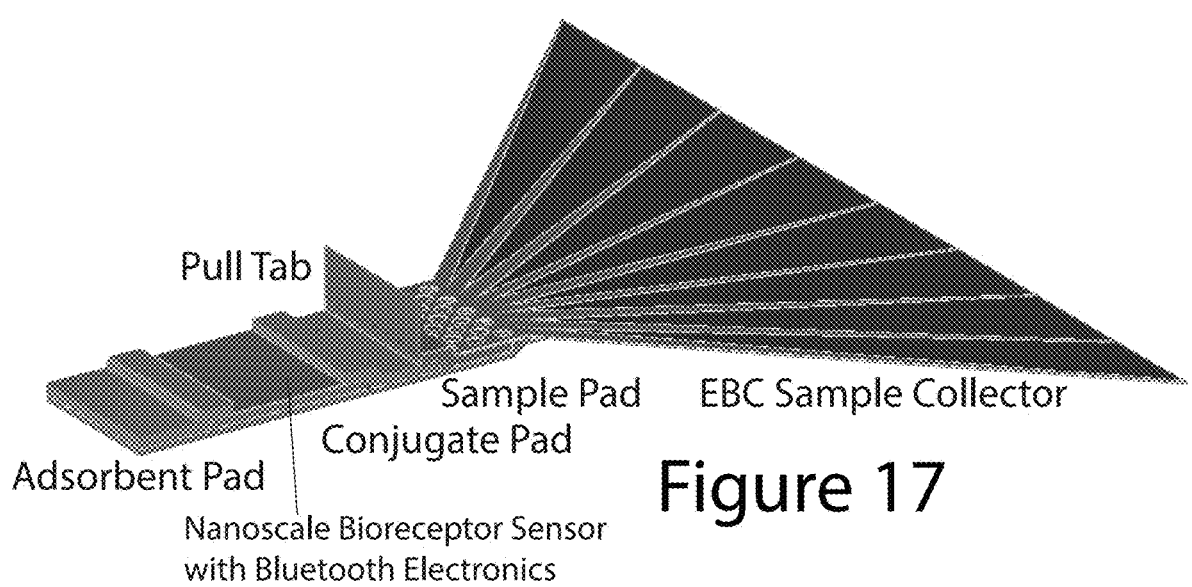
FIG. 17 illustrates the EBC sample collector applied to a nanoscale bioreceptor testing system and showing a pull tab for holding back collected droplets on the sample pad.
Figure 18:
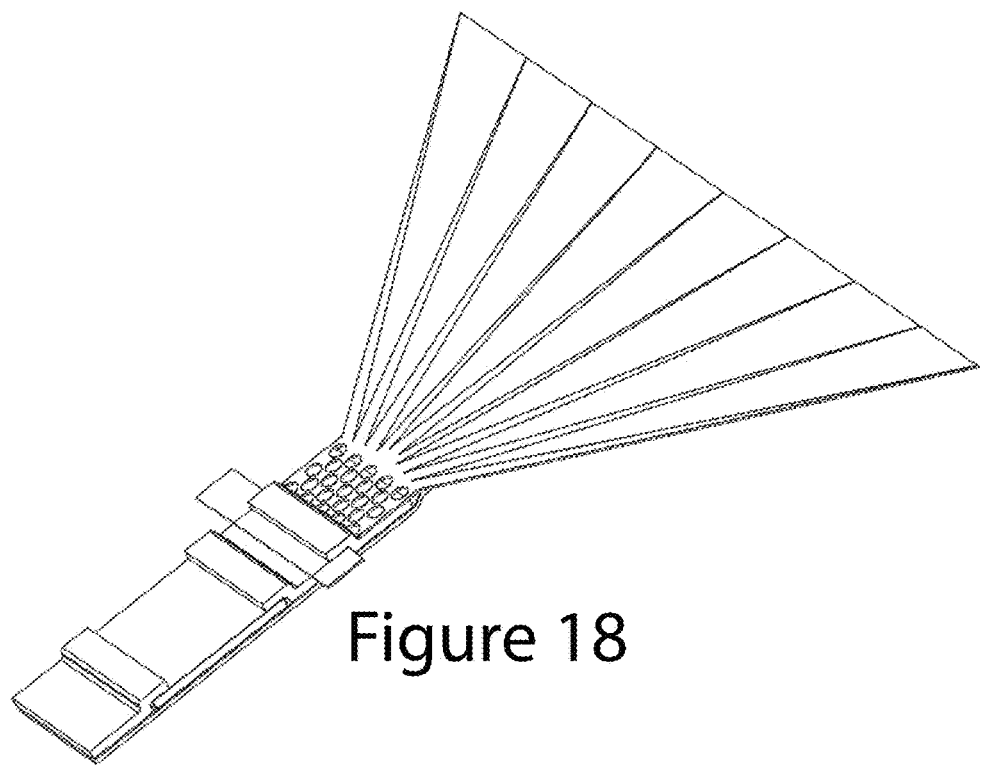
FIG. 18 is a perspective view showing the EBC sample collector applied to a testing system.
Figure 19:
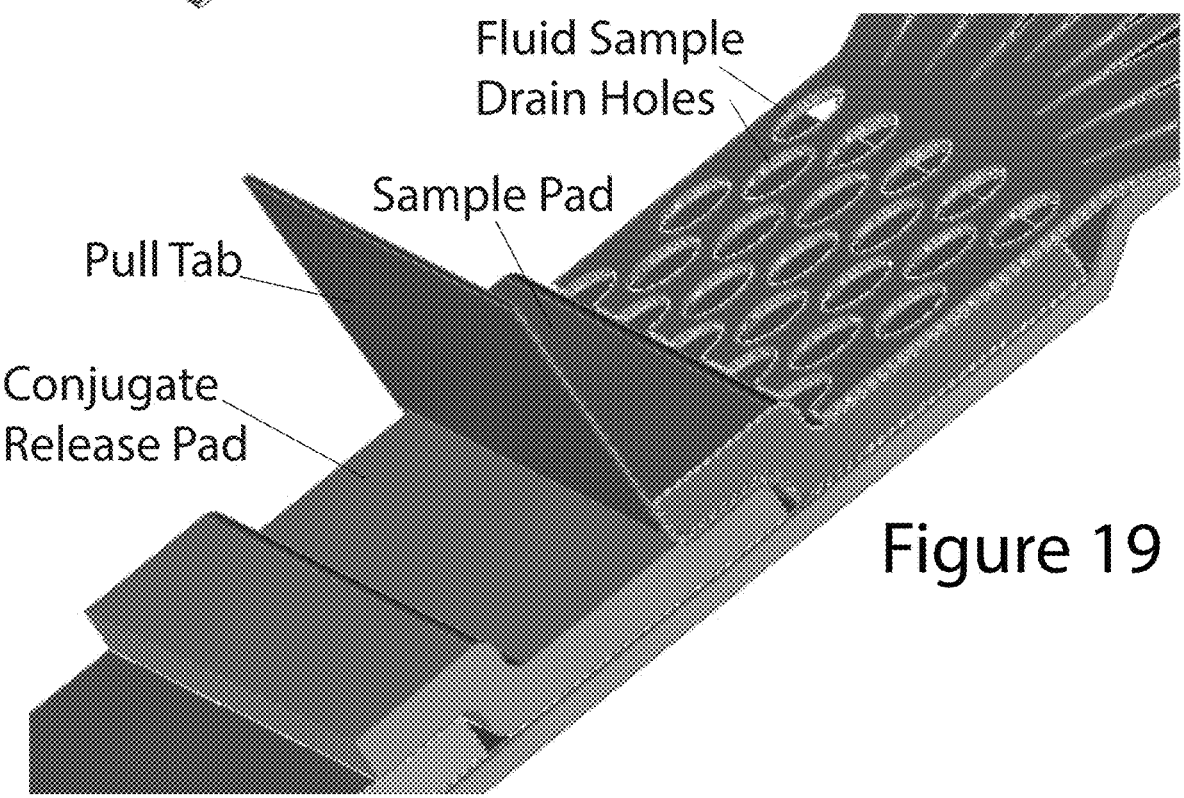
FIG. 19 is an isolated view showing the pull table disposed between the sample pad and conjugate release pad.
Figure 20:
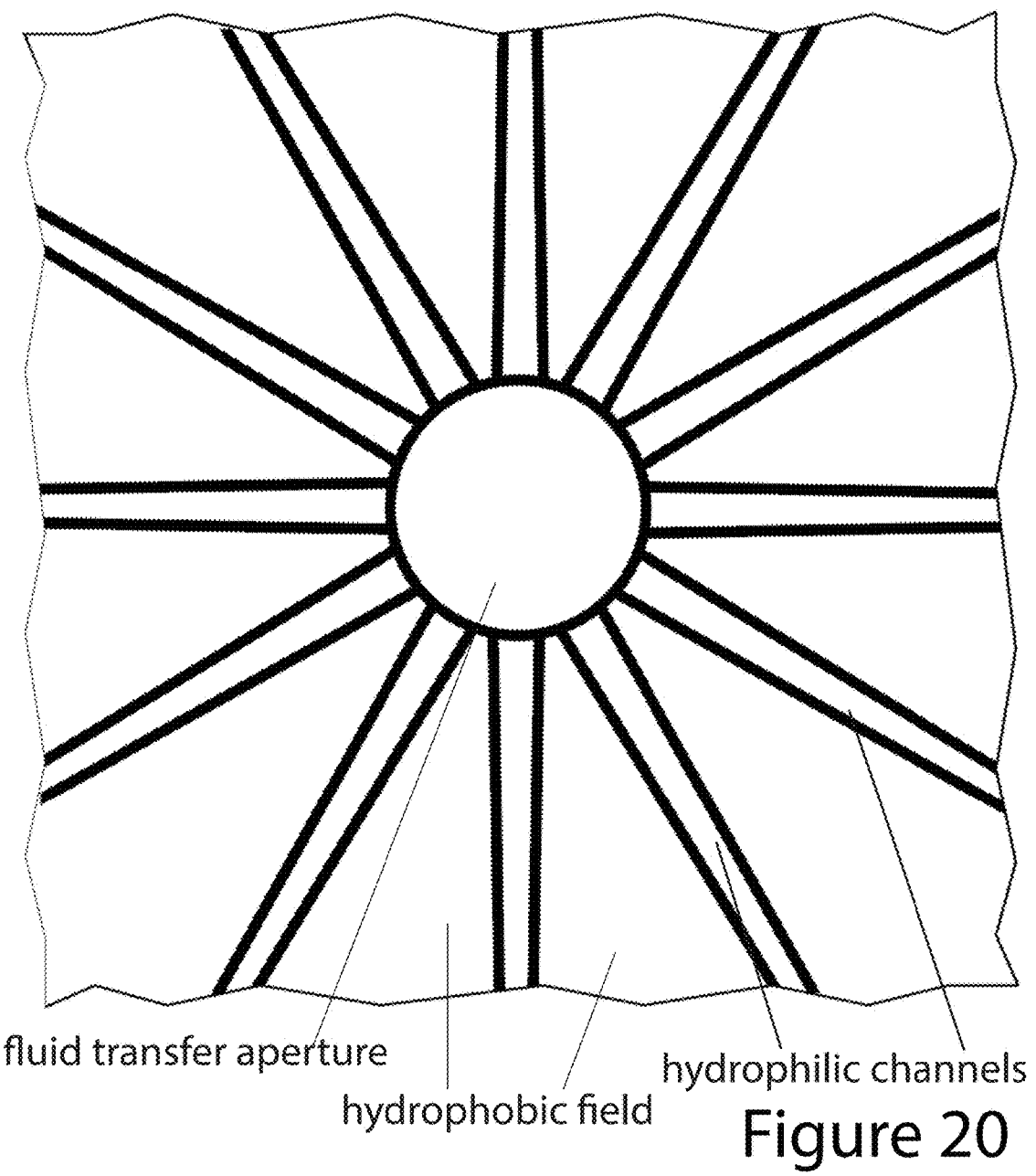
FIG. 20 is an isolated view of a screen printed EBC sample collector with a fluid transfer aperture.
Figure 21:
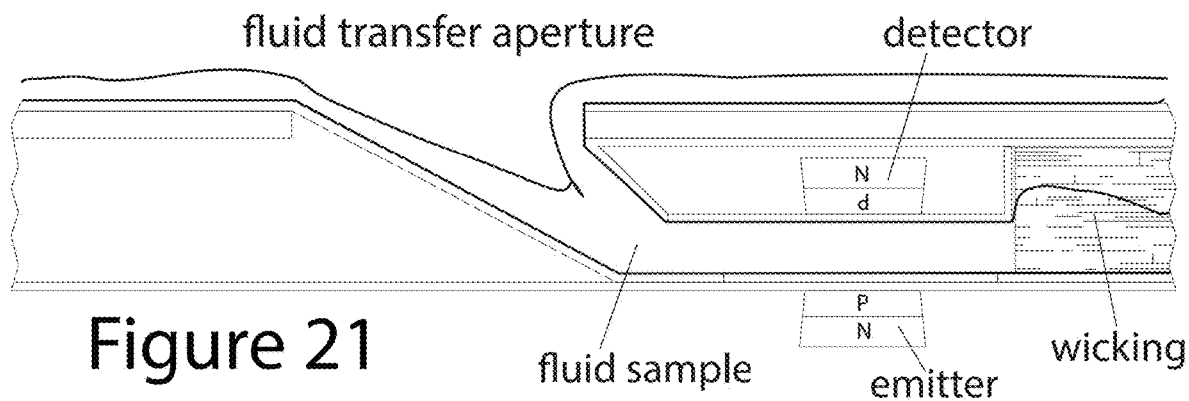
FIG. 21 is a cross-section view showing a fluid sample collected from the EBC sample collector flowing between a photonics emitter/detector pair.
Figure 22:
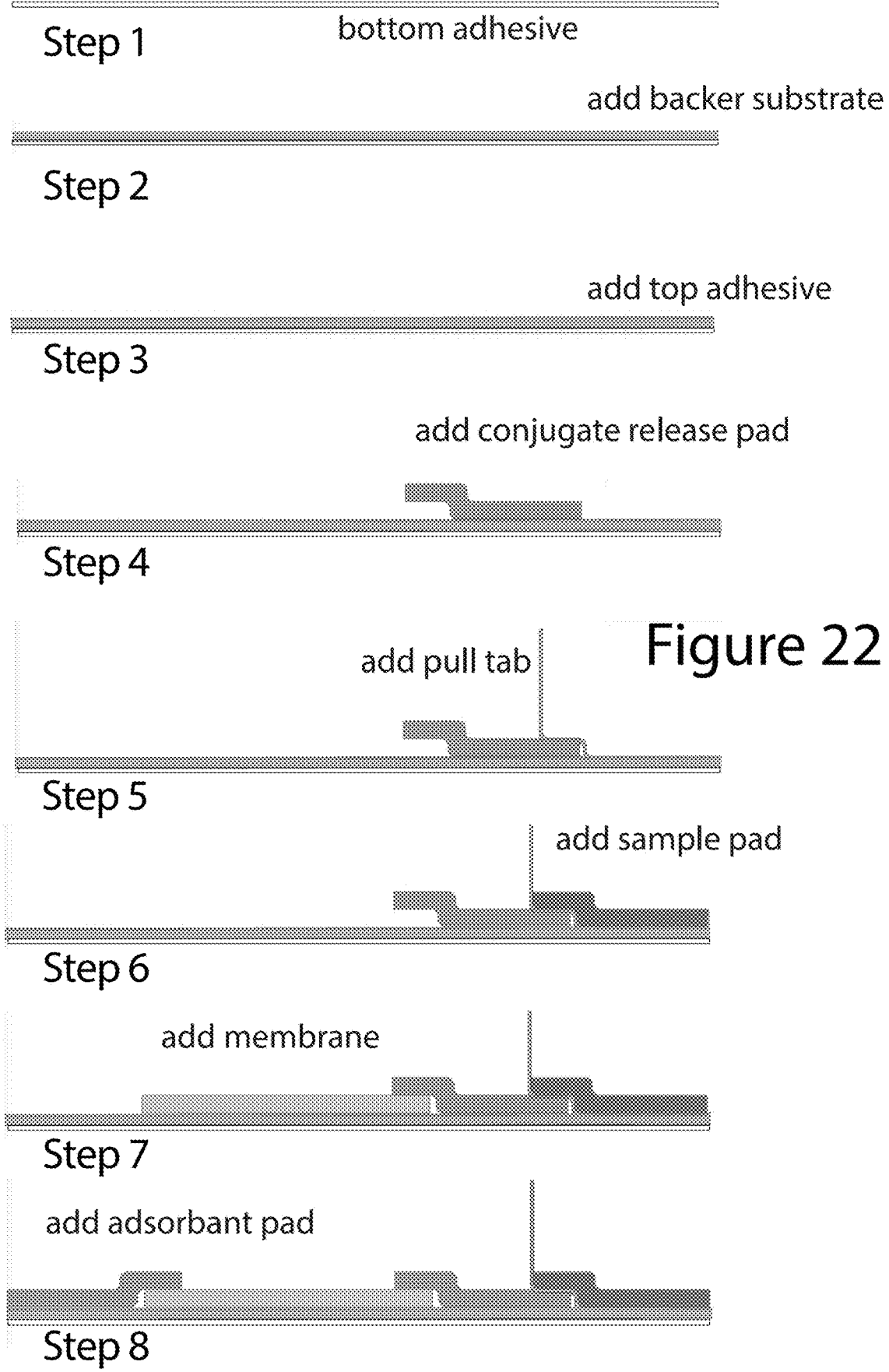
FIG. 22 shows the side views of the steps for building up an LFA testing system.
Figure 24:
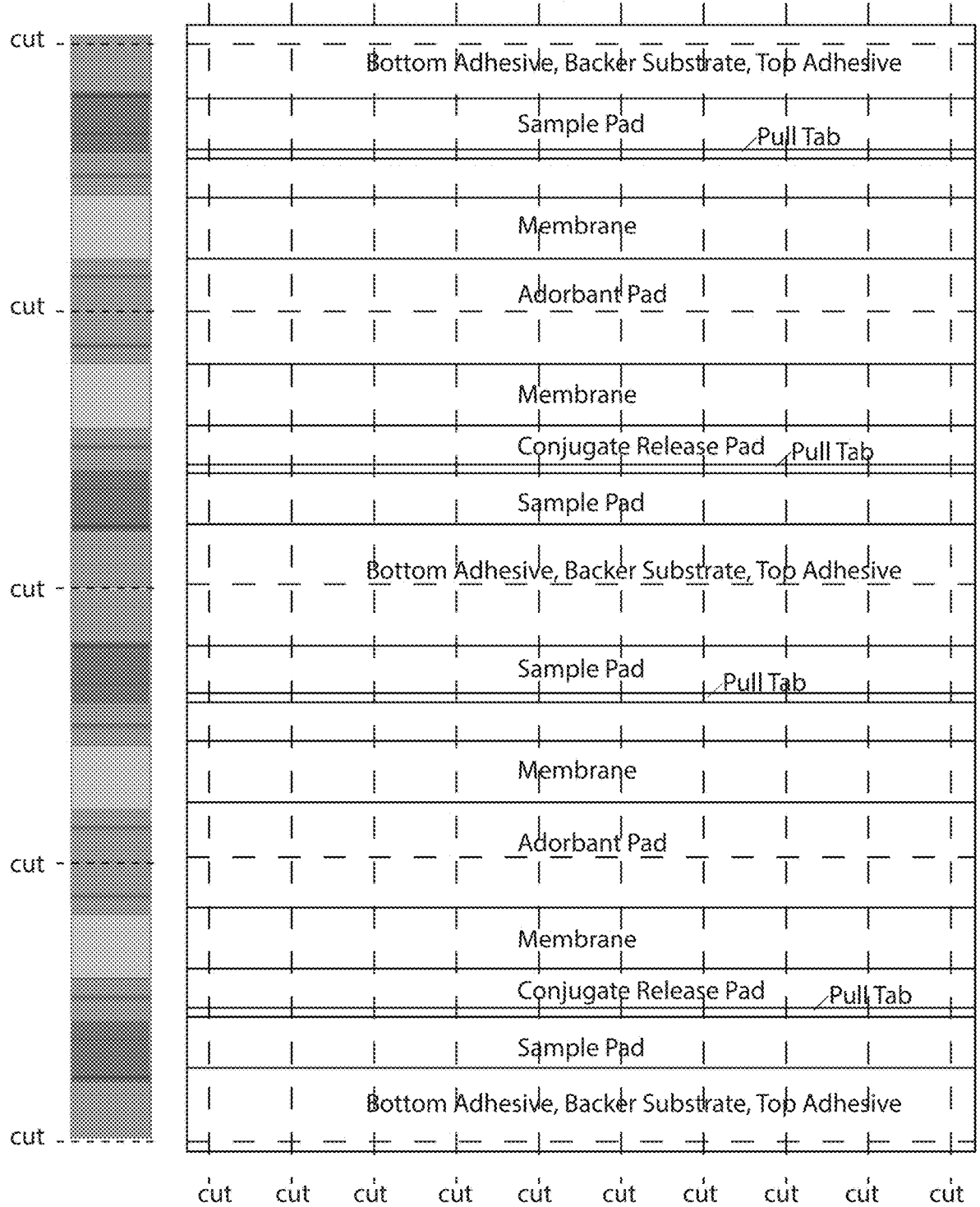
FIG. 24 shows a 4×9 ganged multiple-up sheet of LFA testing systems formed as a batch.

At least one photoemitter and one photodetector may be provided where the photoemitter emits radiation towards the biomarker testing zone and the photodetector receives radiation from the biomarker testing zone. FIG. 15 is an exploded view showing the constituent elements of a LFA. FIG. 16 illustrates an embodiment of the LFA including photonic emitter/detector electronics. In immunochromagtography, a capture antibody is disposed onto a surface of a porous membrane, and a sample passes along the membrane. Analyte in the sample is bound by the antibody which is then coupled to a detector reagent. As the sample passes through the area where the capture reagent is disposed, the analyte detector reagent complex is trapped, and a color develops that is proportional to the analyte present in the sample. The photonics emitter/detector pair enable the proportional quantitative measurement of the analyte where the analyte concentration if the fluid sample is determined from an intensity or counting of received photons at the detector.

The solid-phase lateral-flow test platform is an example of immunochromatography that is widely used for home pregnancy testing. Lateral flow tests have benefited from the use of sol particles as labels. The use of inorganic (metal) colloidal particles are typically used as a label for immunoassays and several techniques are used to measure the amount of bound conjugate. These include naked eye, colorimetry and atomic absorption spectrophotometry. Colorimetry applies the Beer-Lambert law, which states that the concentration of a solute is proportional to the absorbance. At higher antigen concentrations, the results of immunochromagtography can be read by the naked eye (e.g., the typical home pregnancy test). For lower concentrations, colorimetry has been shown to be more than 30 times more sensitive than reading by the naked eye.

Figure 25:
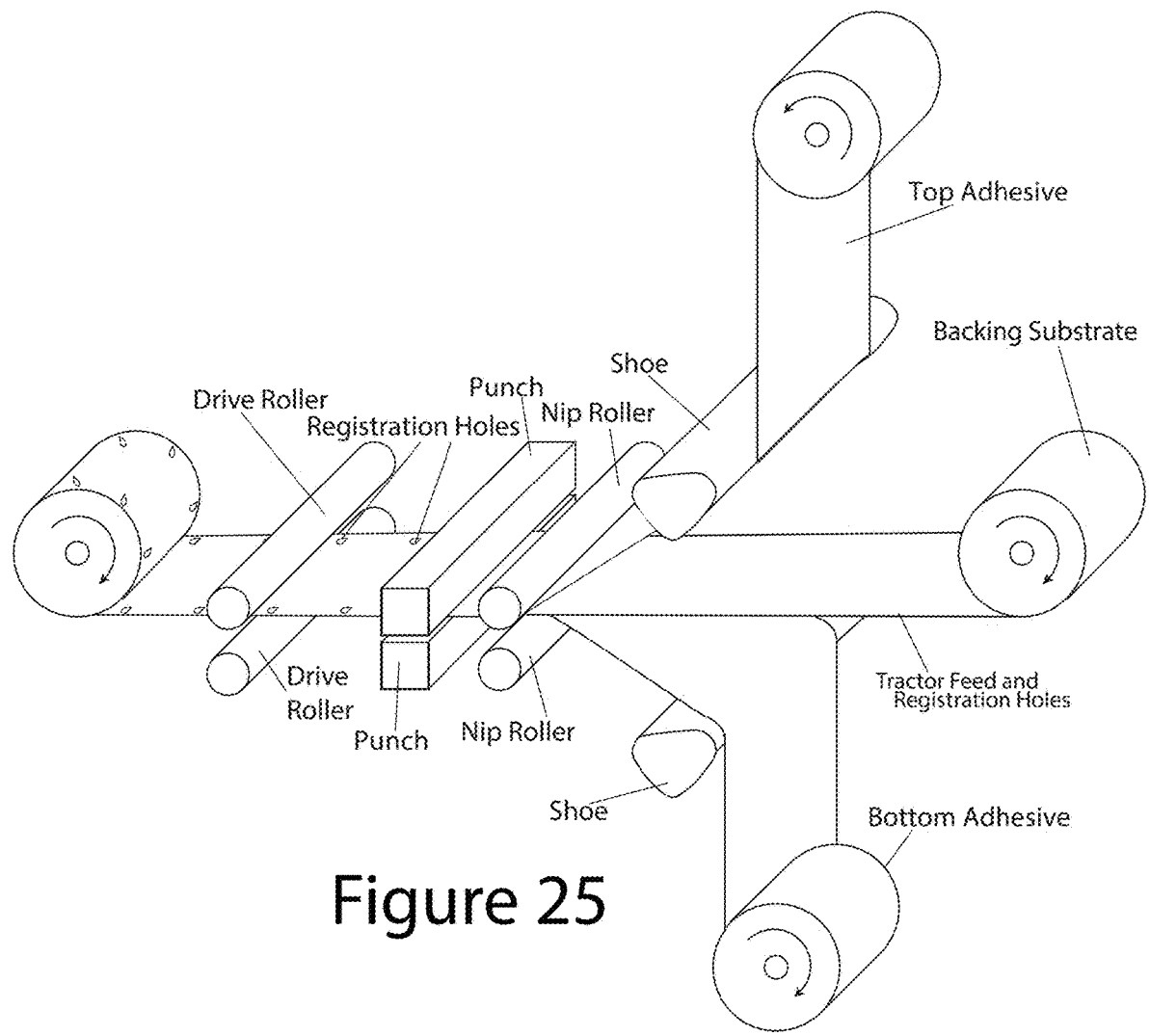
FIG. 25 shows a roll-to-roll manufacturing process for forming a roll of bottom adhesive/backing substrate/top adhesive.

In accordance with an embodiment, immunochromatography is used to detect the present of a COVID-19 analyte. Generally, immunochromatography is the separation of components in a mixture through a medium using capillary force and the specific and rapid binding of an antibody to its antigen. A dry transfer medium is coated separately with novel coronavirus N protein ("T" test line) and anti-mouse antibody ("C" control line). Free colloidal gold-labeled anti-human IgM are in a release pad section (S). The inventive vapor coalescence and droplet harvesting structure are used to obtain a fluid sample of breath condensate. This fluid sample is applied to the release pad section. The anti-human IgM antibody the binds to at least some of the IgM antibodies (if any are present), forming an IgM-IgM complex. The fluid sample and antibodies move through the transfer medium via capillary action. If coronavirus IgM antibody is present in the fluid sample, the novel coronavirus N protein at the test line (T) will be bound by the IgM-IgM complex and develop color. If there is no coronavirus IgM antibody in the sample, free anti-human IgM does not bind to the test line (T) and no color will develop. The free anti-human IgM antibody will bind to the anti-mouse antibody at the control line (C) so that the control line develops color confirming that the fluid sample has transversed through the transfer medium and the test has been correctly performed.

FIG. 17 illustrates the EBC sample collector applied to a nanoscale bioreceptor testing system and showing a pull tab for holding back collected droplets on the sample pad. FIG. 18 is a perspective view showing the EBC sample collector applied to a testing system. FIG. 19 is an isolated view showing the pull table disposed between the sample pad and conjugate release pad. The EBC fluid sample will be collected over some time period, collected from the hydrophobic field through the hydrophilic channels, and flowing through the fluid sample drain holes to build up in the sample pad. A typical LFA uses about 3 drops of buffered sample that is added to the sample pad. In accordance with an exemplary embodiment, buffer materials and surfactants can be incorporated in dry form into the sample pad so that the EBC sample, which is mostly water, will be suitable as a directly applied fluid sample without requiring the addition of a fluid buffer. When a person is at rest, there is about 17.5 ml of EBC produced per hour (see, How much water is lost during breathing?, Zielinski et al., Pneumonol Alergol Pol 2012; 80(4):339-342). There are 20 drops per milliliter. So, every hour at rest there is the potential to collect about 350 drops of EBC. A collection efficiency by the EBC sample collector of only about 3% should provide an adequate number of EBC droplets for a fluid sample in about 15 minutes from an individual at rest.

In accordance with an embodiment, an apparatus for detecting a biomarker comprises a droplet harvesting structure for converting breath vapor to a fluid droplet for forming a fluid sample and a testing system having a biomarker testing zone for receiving the fluid sample and detecting a biomarker. The droplet harvesting structure may include at least one of a hydrophobic field for receiving the breath vapor and forming the fluid droplet from the received breath vapor and hydrophilic channels for receiving the fluid droplet and channeling the fluid droplet towards the testing system. A fluid dam member may be provided disposed between the droplet harvesting structure and the biomarker testing zone.

The testing system may comprise a fluidic lateral flow assay including a sample pad for receiving the fluid sample potentially containing a biomarker analyte, a conjugate release pad, a flow membrane and an adsorbent pad for receiving and flowing the fluid sample to detect the potential biomarker analyte from the sample source. A fluid dam member disposed between the sample pad and the conjugate release pad, the fluid dam including a pull tab structure to enable a user to remove the fluid dam member and allow the flow of the fluid sample from the sample pad to the conjugate release pad.

In order to flush the EBC fluid sample through the test system, the fluid dam is provided to hold back the EBC on the sample pad as it accumulates. The fluid dam may be, for example, a piece of silicone coated release paper forming a pull tab that is disposed between the sample pad and the conjugate release pad. The pull tab is held in place on the top adhesive and allows for the accumulation of the EBC fluid sample. After an adequate amount of time has passed to saturate the sample pad with enough EBC fluid sample, the user pulls the pull tab out causing the EBC fluid sample to flow from the sample pad to the conjugate release pad. This enables the EBC fluid sample to flush through the various constituents of the testing system by capillary action. The EBC fluid sample is allowed to build up on the sample pad so that removing the pull tab releases sample flow all at once to ensures adequate sample flow and promotes testing consistency.

FIG. 20 is an isolated view of a screen printed droplet sample collector with a fluid transfer aperture. FIG. 21 is a cross-section view showing a fluid sample collected from the EBC sample collector flowing between a photonics emitter/detector pair. In this embodiment, another body fluid, such as sweat, might be used with the EBC sample collector configured to harvest sweat droplets from the skin instead of coalescing breath vapor into exhaled breath condensate. It is noted that any of the embodiments and innovations described herein may be useful for other medical and fitness uses, for other disease or virus testing or biometric detection in addition to or instead of the described use for COVID-19 testing.

The manufacturing techniques, equipment and materials for most components of an embodiment of the inventive COVID-19 testing system are readily available and very well known. For example, to create our fluid harvesting and droplet channeling structure, screen printing is used to pattern hydroscopic and hydrophobic inks sourced from a company such as Cytonix and Wacker. There is no shortage of manufacturing capacity needed to quickly screen print for the hundreds of millions of testing units needed. The fluidic biosensor component can be manufactured using high throughput equipment available from a company such as Nano-Ops, Boston, MA, and the chemistry for functionalizing the biosensor can be obtained from a company such as RayBiotech, Peach Tree Corners, GA Other necessary manufacturing steps, such as wire bonding and printed circuit board fabrication will make use of the same ubiquitous machines that are similarly purposed for semi-conductor and circuit board electronics.

FIG. 22 shows the side views of the steps for building up an LFA testing system. FIG. 23 shows the top view of the steps for building up an LFA testing system. FIG. 24 shows a 4×9 ganged multiple-up sheet of LFA testing systems formed as a batch. FIG. 25 shows a roll-to-roll manufacturing process for forming a roll of bottom adhesive/backing substrate/top adhesive.

Figure 26:
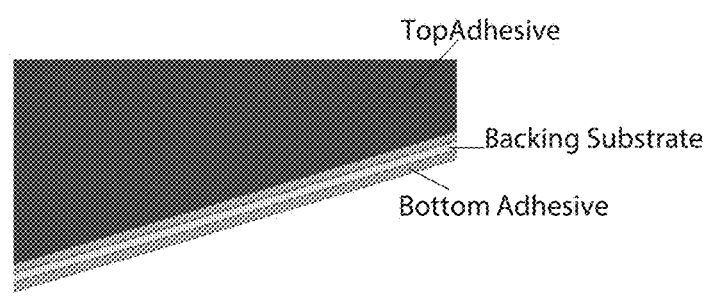
FIG. 26 is a perspective view illustrating the bottom adhesive/backing substrate/top adhesive stack.
Figure 27:
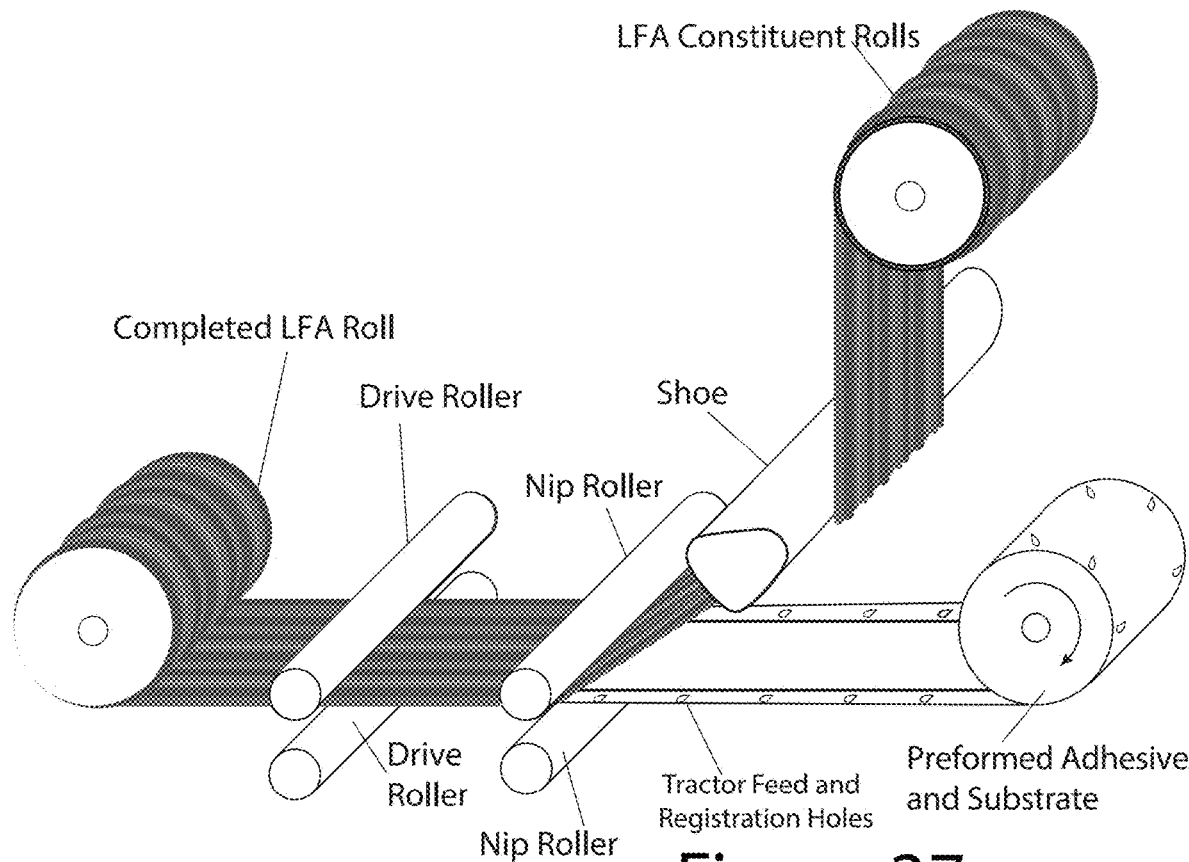
FIG. 27 shows a roll-to-roll manufacturing process for forming the constituent elements of an LFA on a roll of bottom adhesive/backing substrate/top adhesive.
Figure 28:
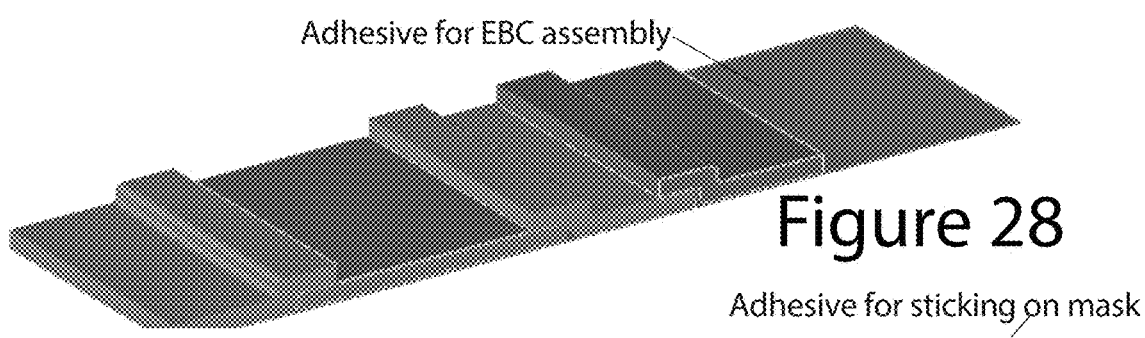
FIG. 28 shows the LFA testing system formed by the roll-to-roll process cut from a continuous roll and showing a section of top adhesive for adhering the LFA testing system to a separately formed ENC sample collector.
Figure 29:
FIG. 29 shows the LFA testing system formed by the roll-to-roll process cut from a continuous roll and showing a section of bottom adhesive for sticking onto a wearable garment such as a face mask.
Figure 30:
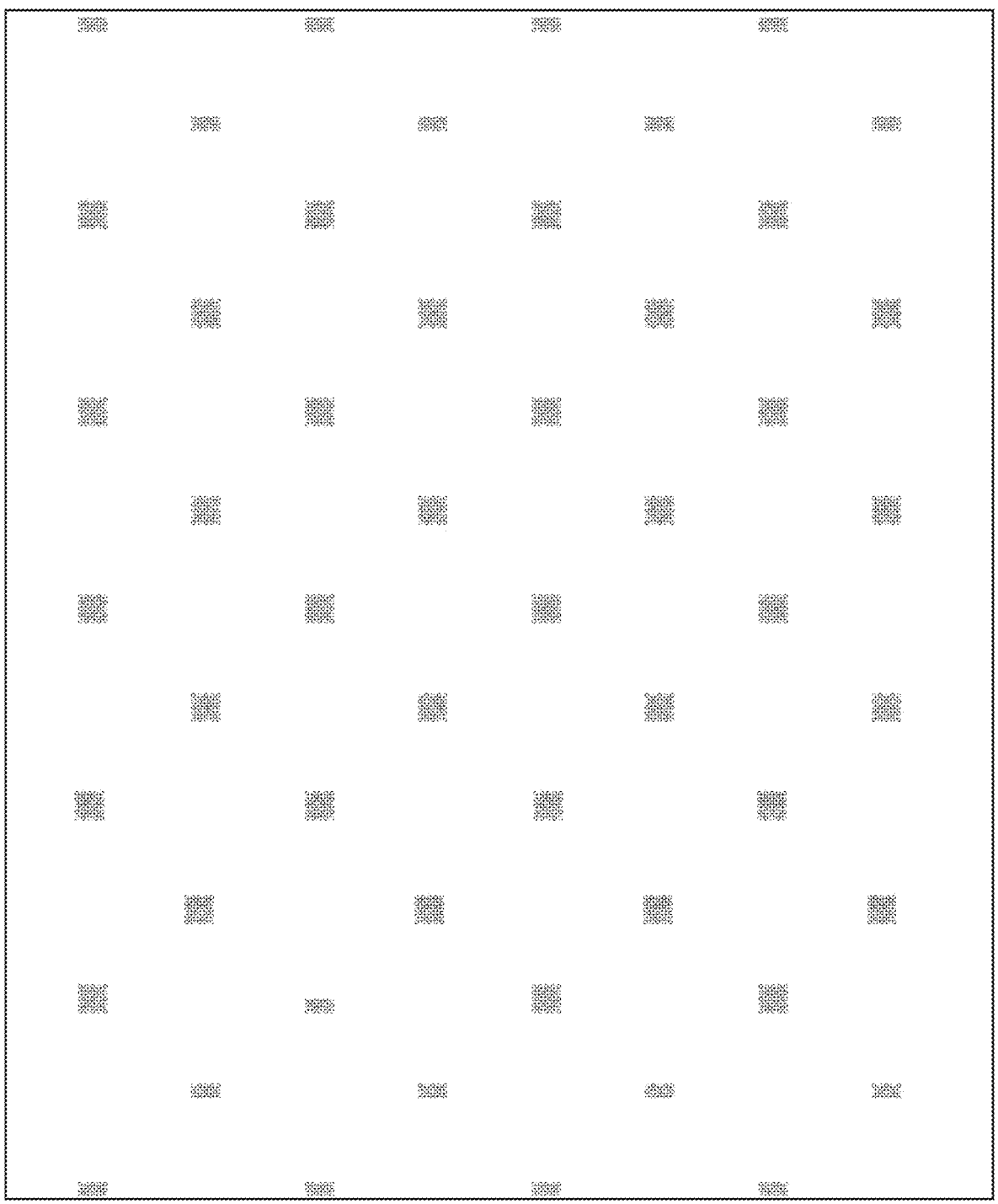
FIG. 30 shows a sheet of substrate with a hydrophobic field coating on a thermal mass substrate with droplet collection holes.
Figure 31:
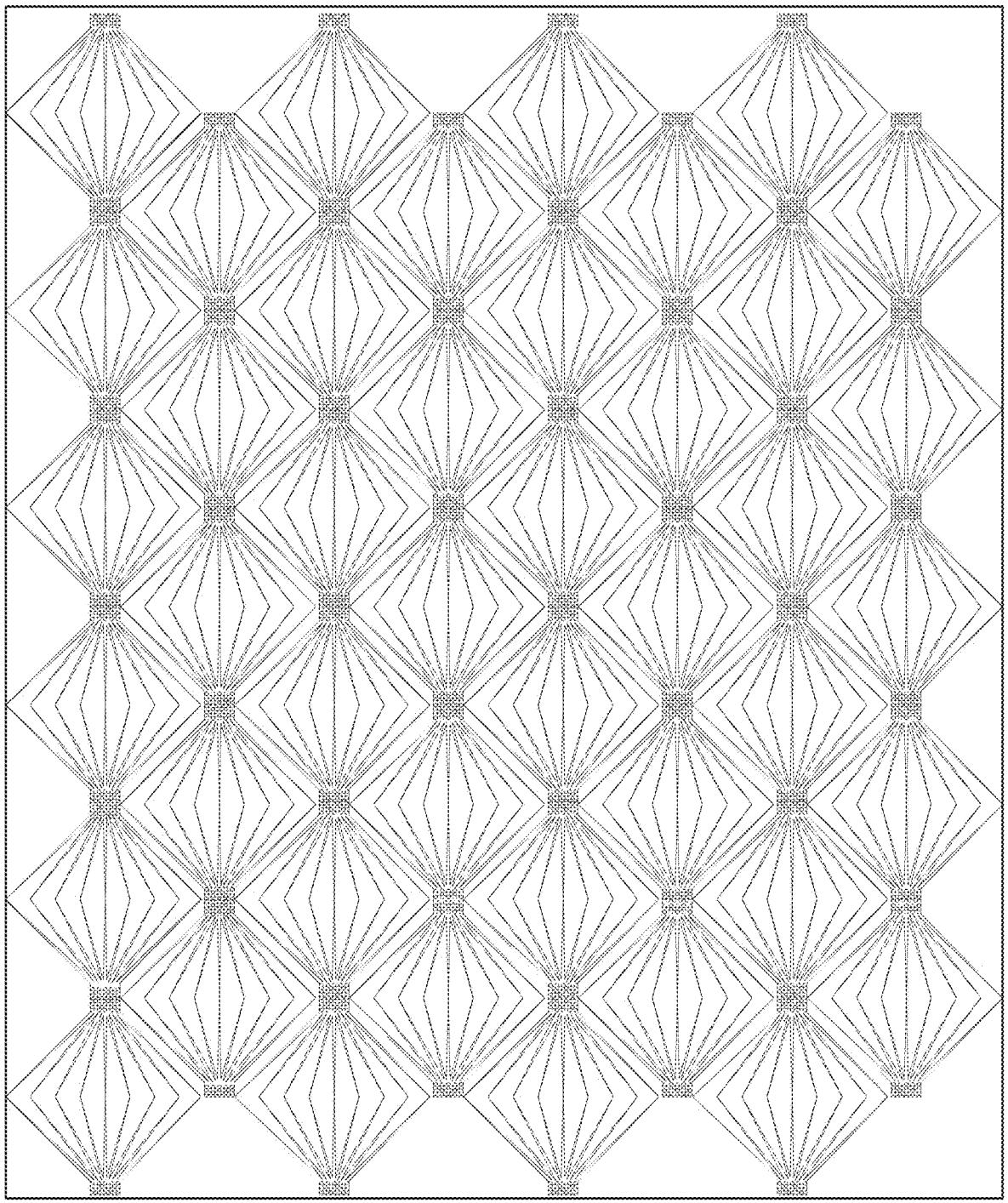
FIG. 31 shows the sheet of substrate with the hydrophobic field coating on the thermal mass substrate with droplet collection holes having a coating of hydrophilic channels.

FIG. 26 is a perspective view illustrating the bottom adhesive/backing substrate/top adhesive stack. FIG. 27 shows a roll-to-roll manufacturing process for forming the constituent elements of an LFA on a roll of bottom adhesive/backing substrate/top adhesive. FIG. 28 shows the LFA testing system formed by the roll-to-roll process cut from a continuous roll and showing a section of top adhesive for adhering the LFA testing system to a separately formed ENC sample collector. FIG. 29 shows the LFA testing system formed by the roll-to-roll process cut from a continuous roll and showing a section of bottom adhesive for sticking onto a wearable garment such as a face mask. FIG. 30 shows a sheet of substrate with a hydrophobic field coating on a thermal mass substrate with droplet collection holes. FIG. 31 shows the sheet of substrate with the hydrophobic field coating on the thermal mass substrate with droplet collection holes having a coating of hydrophilic channels.

Figure 32:
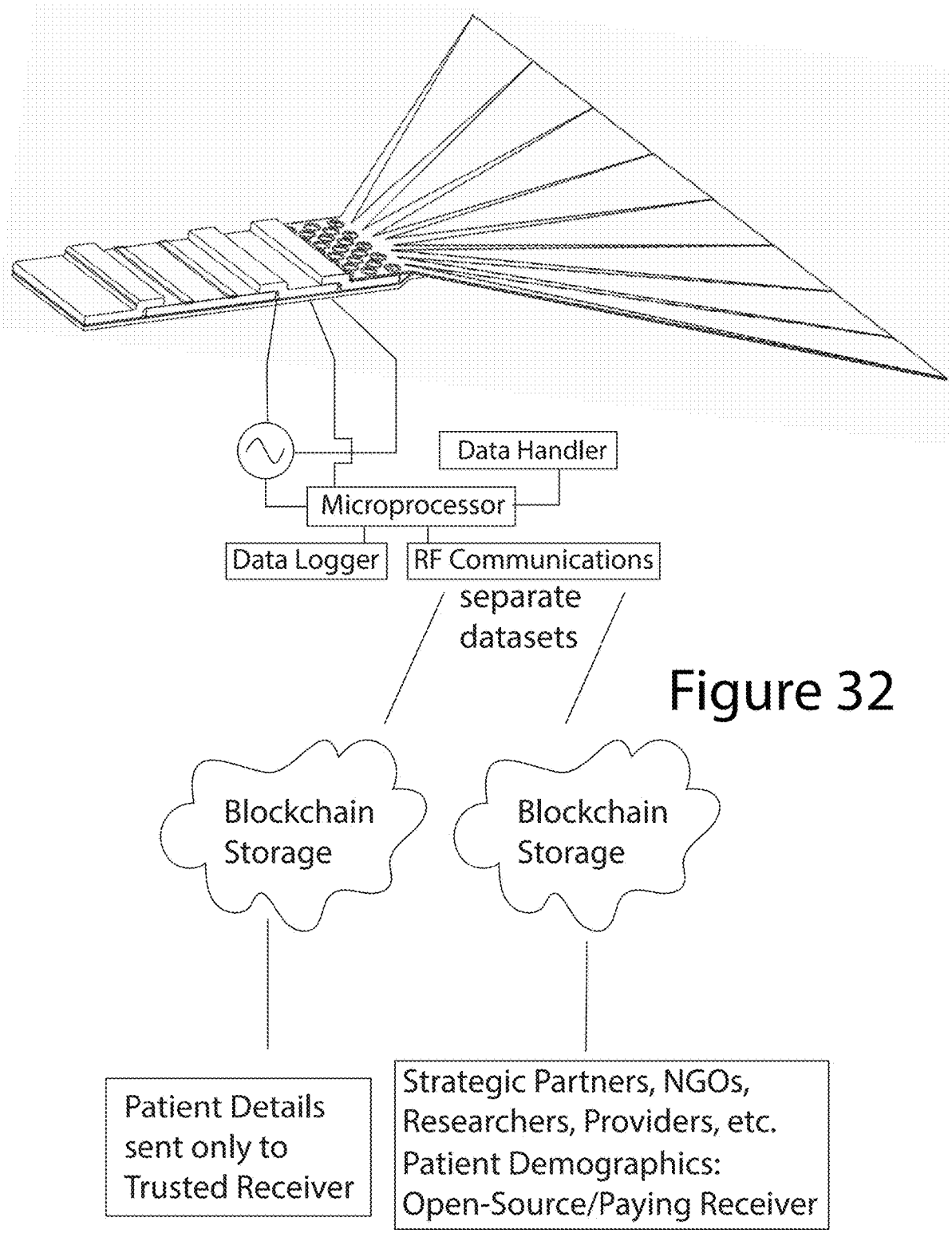
FIG. 32 shows the EBC sample collector and testing system with electronics for wireless data acquisition and transmission along with separate trusted receiver and public blockchain data path and storage.

FIG. 32 shows the EBC sample collector and testing system with electronics for wireless data acquisition and transmission along with separate trusted receiver and public blockchain data path and storage. Villanova University recently published an example of utilizing blockchain to help medical facilities track coronavirus cases globally. A private blockchain is shared among medical facilities around the world to publish coronavirus test results between doctors on a trusted, immutable ledger. IoT and AI are used to survey public spaces where high-risk gatherings can take place and trigger alerts over the blockchain.

In accordance with an exemplary embodiment, the EBC collecting system with biomarker detection can utilize self-reporting or automatic data collection to be usable with a new or existing APPs for contact tracing and electrical medical records. The acquired data can anonymized and encrypted at the source (e.g., on the electronics associated with the testing system). A first data stream/data base allows a trusted receiver to access patient identifying data while a second data stream/data base provides anonymized data that can be provided as open source or other data transmission, storage and utilization mechanisms without identifying who the source of the data is from.

The inventive testing system has the potential to be very low cost, shippable in a conventional envelop for mass distribution to every household in a target region, state or country. This enables a much higher percentage of the population to undergo at least the baseline testing indicating if they should follow up with a visit to a drive through, hospital or clinic testing facility for more elaborate testing.

The inventive COVID-19 testing system can have the capability of testing two or more of the virus biomarkers. For example, RNA testing can be combined with antibody testing. By testing for these two biomarkers the potential for false negatives is significantly statistically reduced and likely will be a more preferable methodology.

The proposed COVID-19 testing system can be incorporated into personal protection equipment, such as masks, or provided as a patch that is stuck onto the body, or provided as a stand-alone test unit, similar to a home pregnancy test.

The testing system can include wireless communications capabilities, such as RFID and Bluetooth. This will enable, for example, test data to be used along with GPS location information to assist in contact tracing and further quicken the ability of a growing segment of the population to return to work and restart economic activities, and to also determine through real-time contact tracing who might have been exposed to the virus.

As an enhancement to the basic system, biometric data can be acquired and used for the public good. The collection of biometric information carries with it the burden of privacy issues. There can be considered two uses for a patient's biometric data: Patient monitoring for prevention and treatment; and Population studies to improve global healthcare. The inventive system uses separately created and maintained data bases.

The biometric parameters such as those described herein with regards to the embodiments can also be detected, logged and/or transmitted, enabling a detailed history of the patient's disease progression, therapy, course of treatment, measured results of treatment, etc., and can be made available to improve the care given to the particular patient, and in the aggregate, provide significant data along with that of other patients, to assist in new drug discovery, treatment modifications, and a number of other advantages of the beneficial cycle created by detection, transmission, storage and analysis of biometric data taken directly from the patient during the course of drug therapy and/or other treatments.

Figure 33:
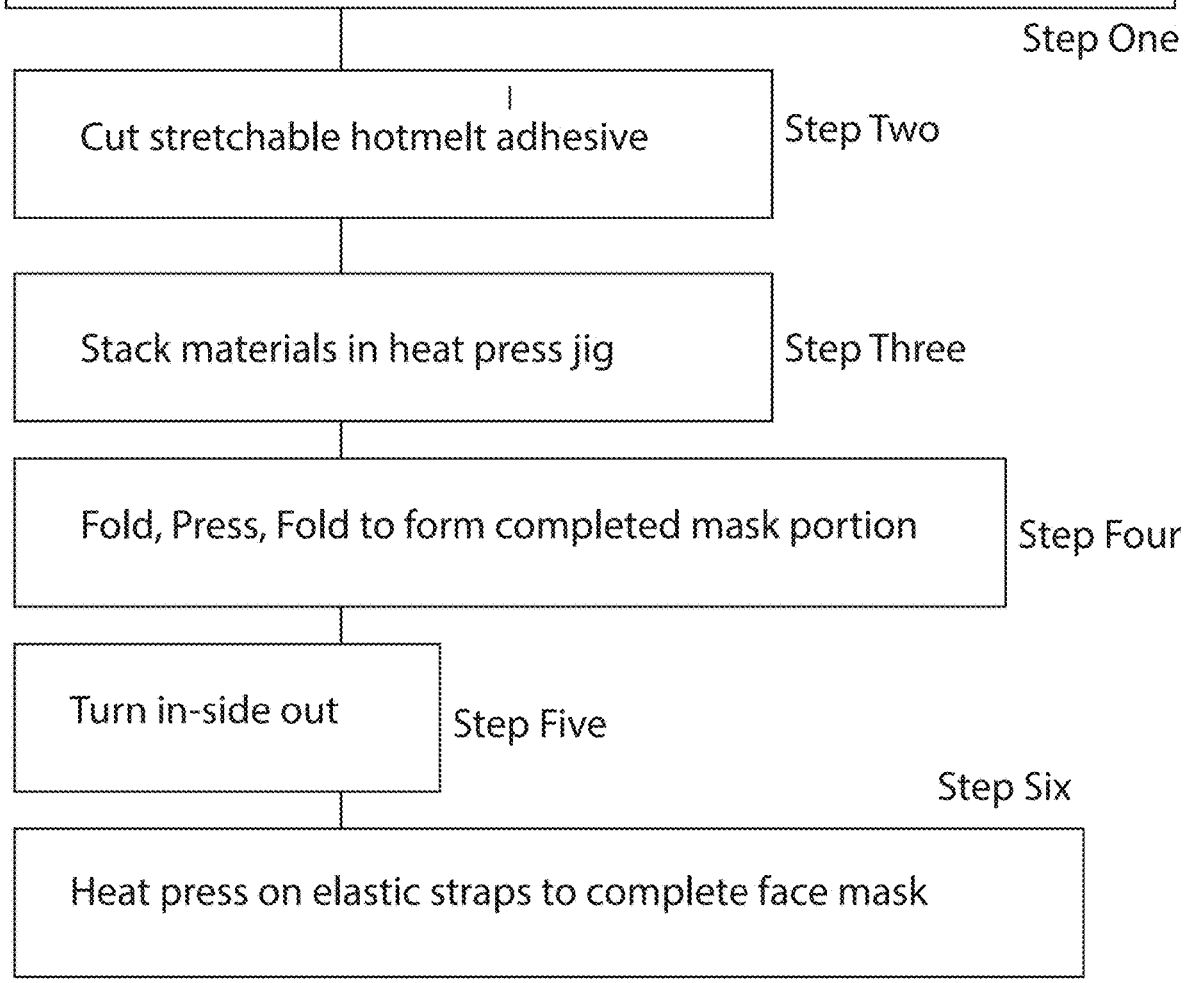
FIG. 33 shows the manufacturing processes for a heat bonded face mask.

FIG. 33 shows the manufacturing processes for a heat bonded face mask. FIG. 34 shows the fabric, filter and other layers bonded through a roll-to-roll lamination process ore individually cut into blanks for forming a pre-form mask stack. FIG. 35 shows other materials such as biological reactive silver fabric and hot melt adhesive of the pre-form mask stack. The highly contagious and deadly effects of COVID-19 have resulting in an increased need for personal protective masks. Disposable masks are a good solution for healthcare providers, police and others who's job put them into constant contact with individuals who may or may not have the virus. The ability to change out a disposable mask between patients, for example, ensures that a doctor or nurse will have a fresh, clean, uncontaminated mask to better protect themselves and protect their patients from the spread of the virus. However, disposable masks are not a good solution for the general population. The cost and waste associated with a disposable mask makes it a poor solution for most people. Rather, what is needed is a mask that is low cost, easy to manufacture and ideally can be sterilized in a conventional home clothes washing machine and dryer.

Figure 36:
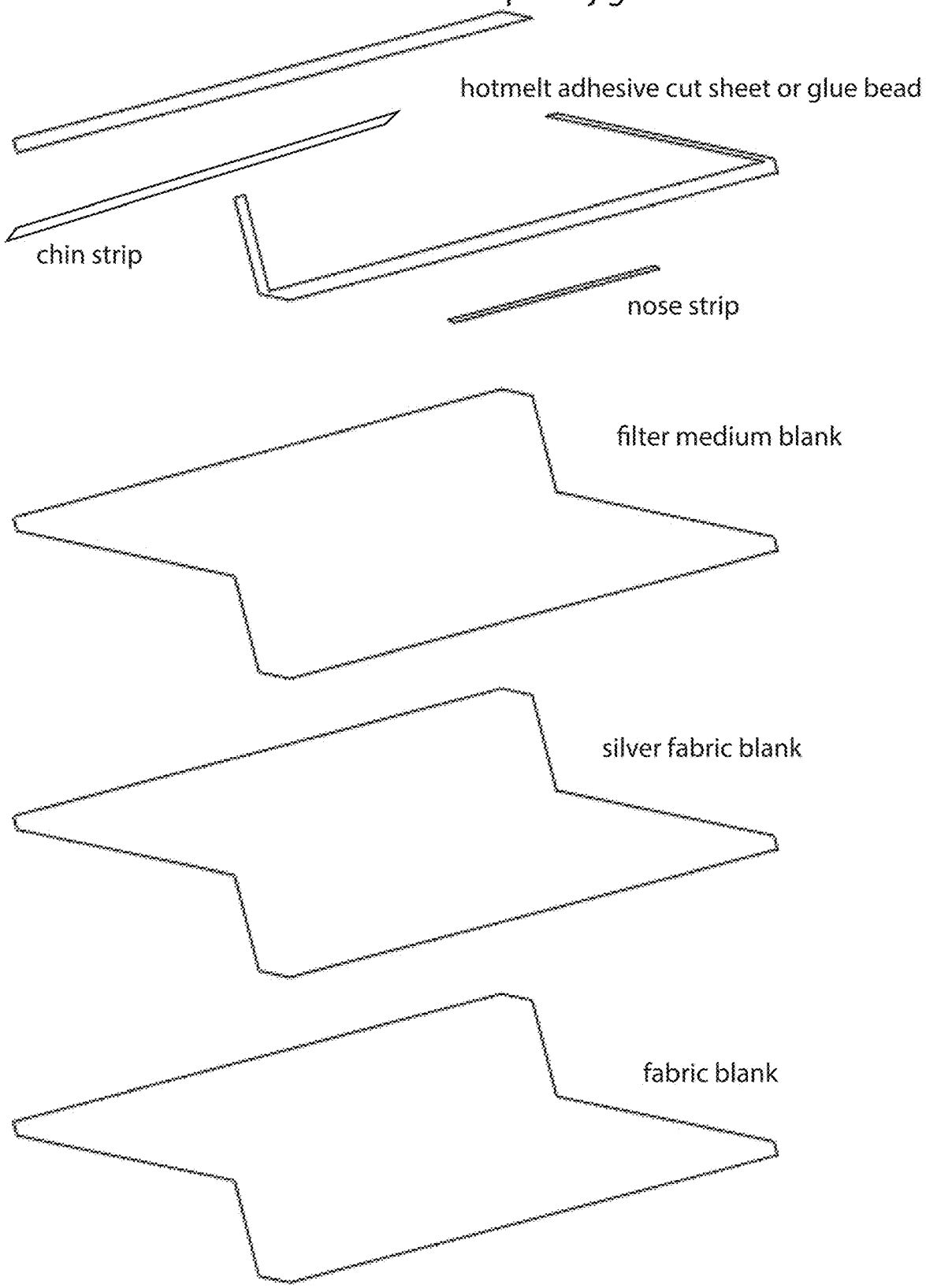
FIG. 36 is an exploded view of a mask stack.
Figure 37:
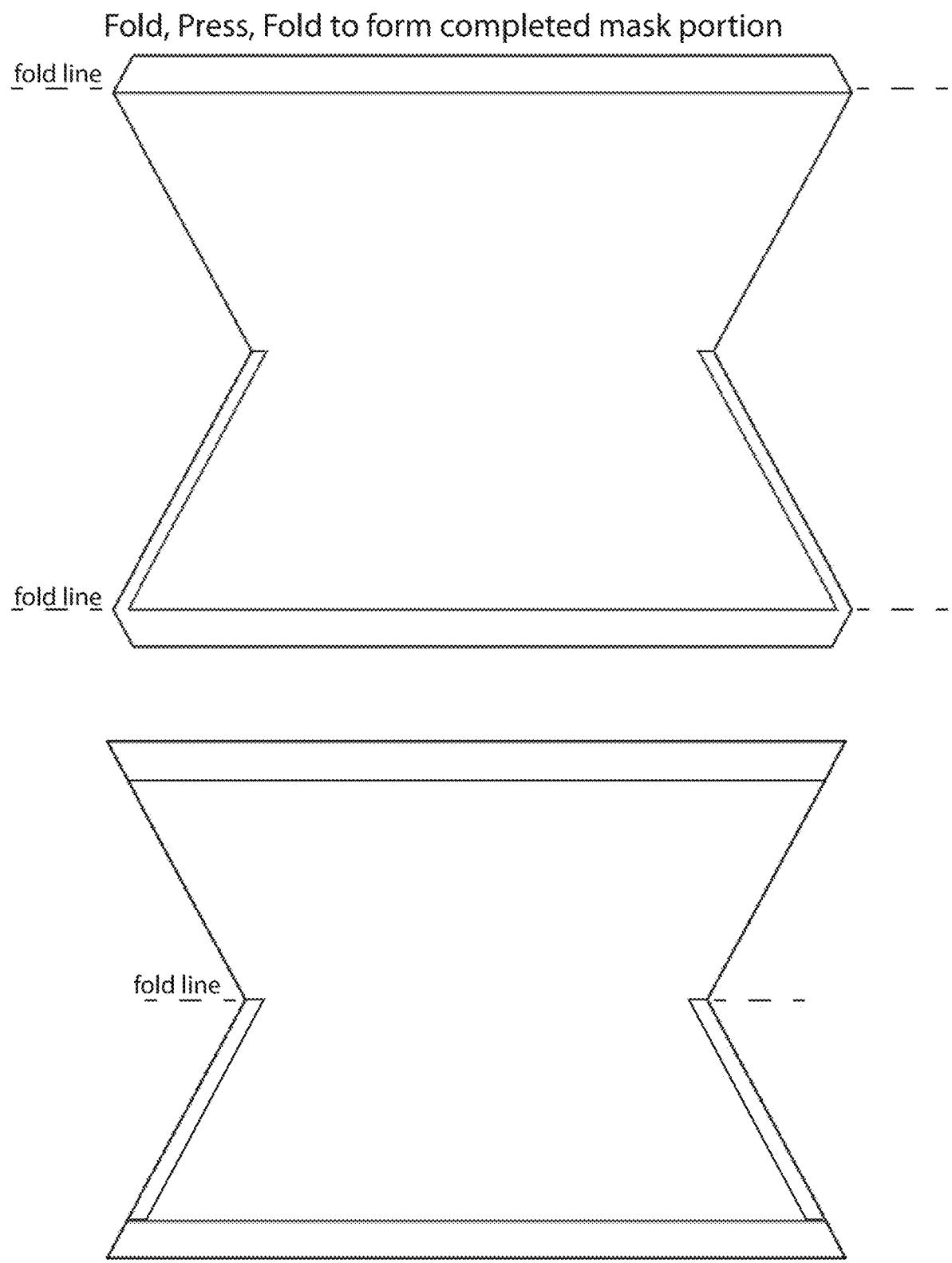
FIG. 37 shows the fold lines of the mask stack for first and second heat press operations.
Figure 38:
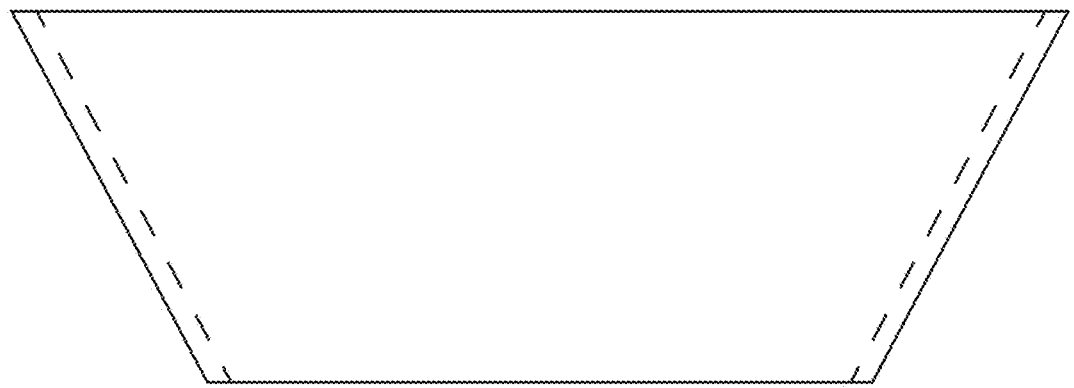
FIG. 38 shows the folded, pressed and heat bonded mask.
Figure 39:
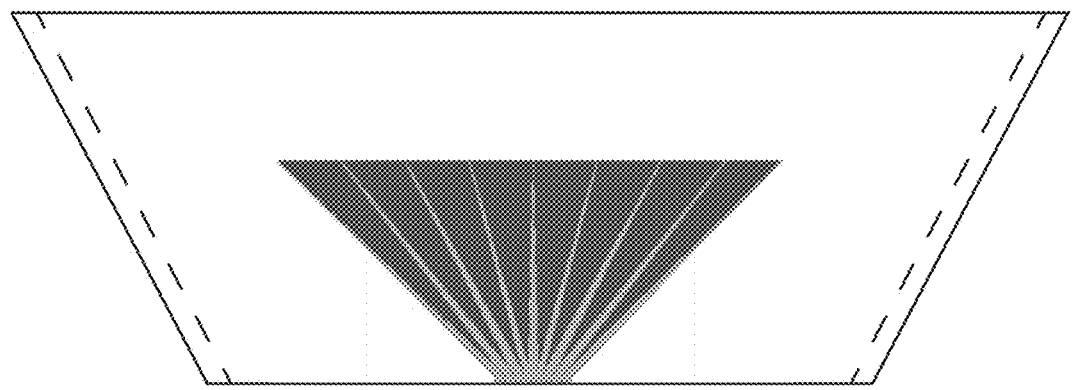
FIG. 39 shows the attachment of the EBC collector and testing system to the folded mask.
Figure 40:
FIG. 40 shows the step of turning the folded mask inside out to dispose the EBC collector and testing system on the inside of the mask.
Figure 41:
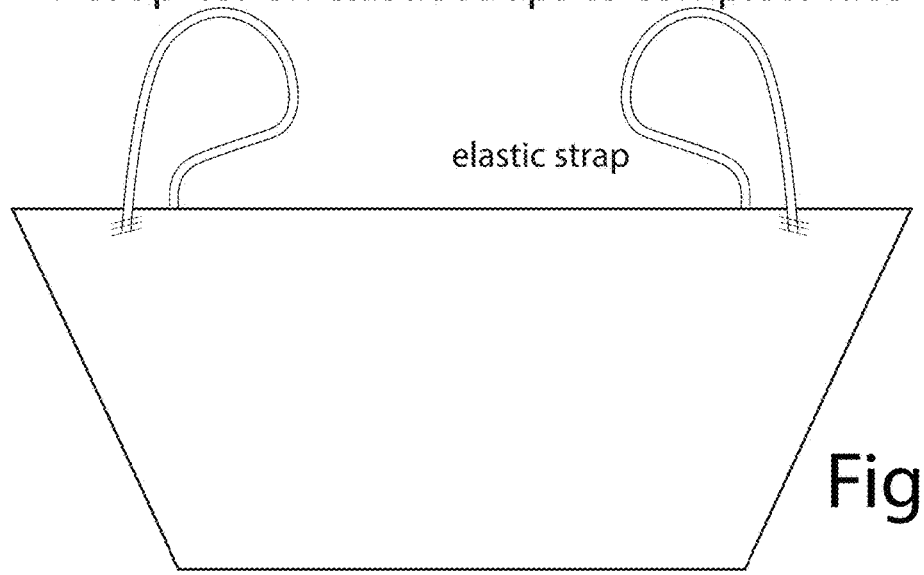
FIG. 41 shows a heat press operation to bond elastic straps onto the folded mask.
Figure 42:
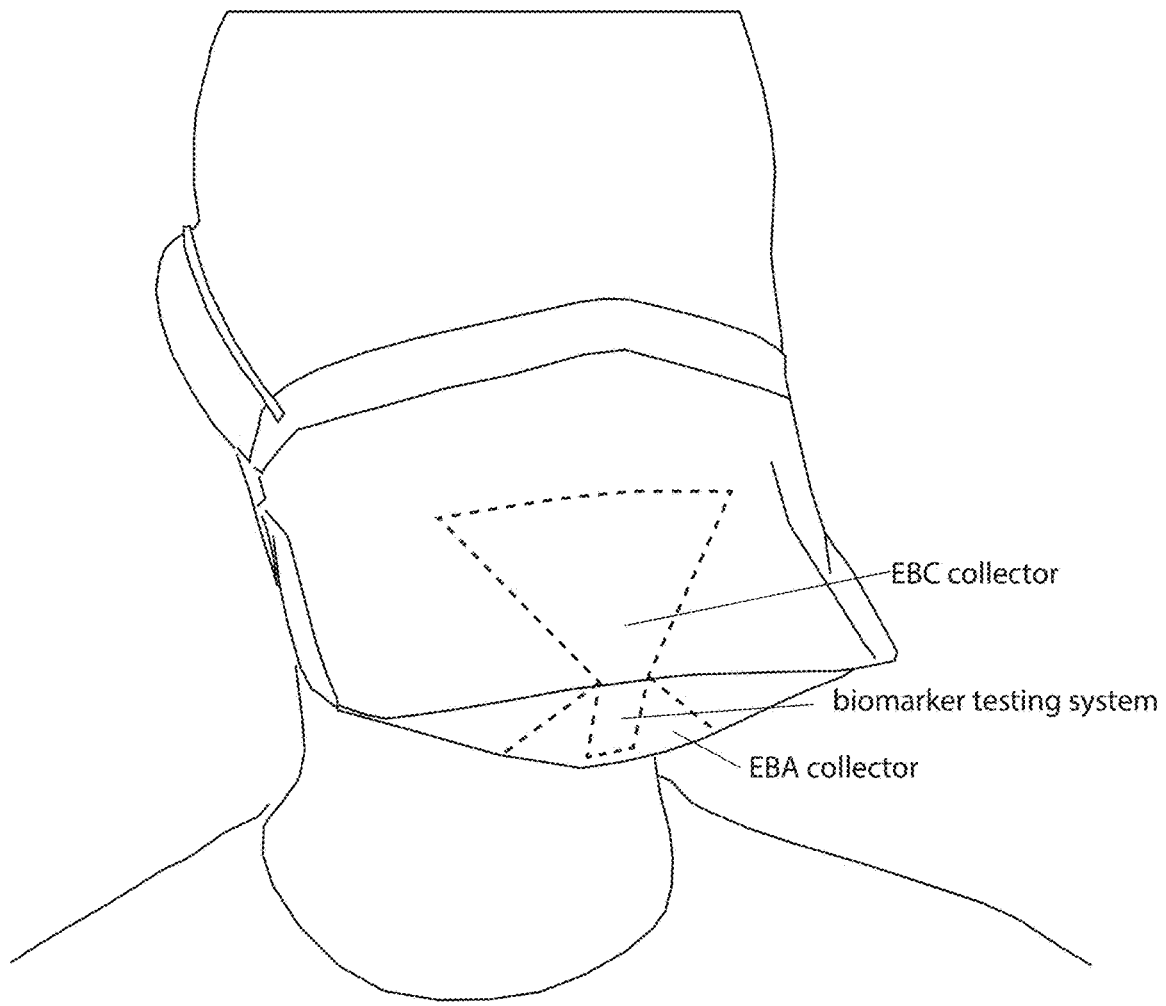
FIG. 42 shows the mask with the EBC collector and testing system disposed inside the mask within the concentrated atmosphere of exhaled breath.
Figure 43:
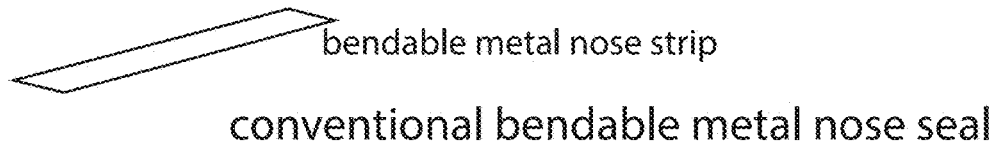
FIG. 43 shows a conventional bendable metal nose seal that is disposed within the folds of the mask at a location corresponding to the bridge of a user's nose.
Figure 44:
FIG. 44 shows a replaceable adhesive nose strip that is disposed on the outside of the folds of the mask at a location corresponding to the bridge of a user's nose.
Figure 45:
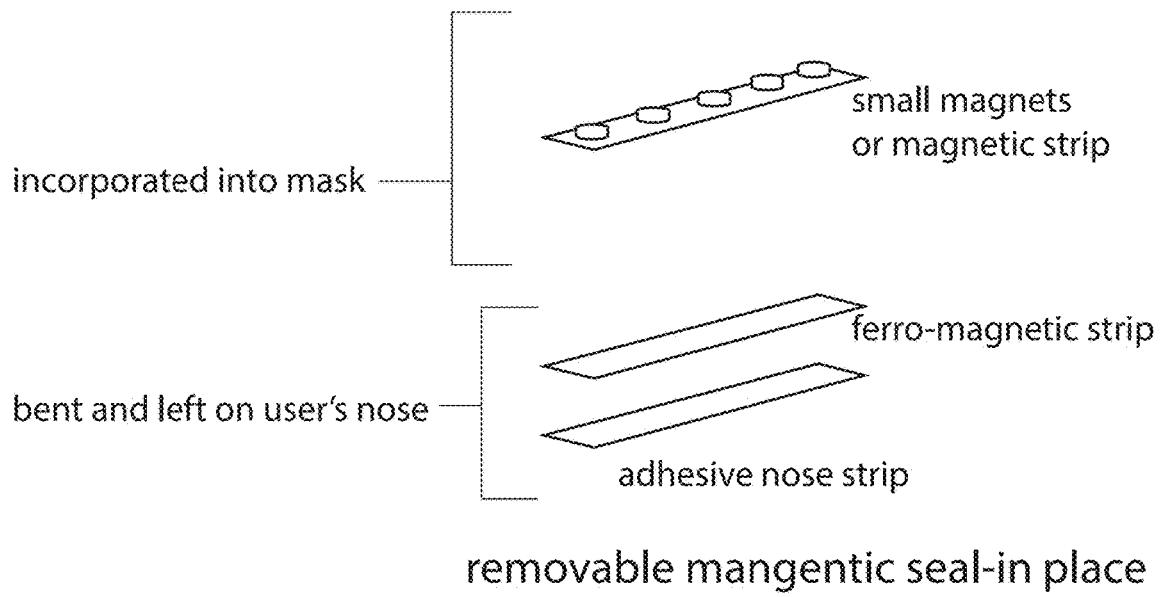
FIG. 45 shows the components of a magnetic removable nose seal.

FIG. 36 is an exploded view of a mask stack. FIG. 37 shows the fold lines of the mask stack for first and second heat press operations. FIG. 38 shows the folded, pressed and heat bonded mask. FIG. 39 shows the attachment of the EBC collector and testing system to the folded mask. FIG. 40 shows the step of turning the folded mask inside out to dispose the EBC collector and testing system on the inside of the mask. FIG. 41 shows a heat press operation to bond elastic straps onto the folded mask. FIG. 42 shows the mask with the EBC collector and testing system disposed inside the mask within the concentrated atmosphere of exhaled breath. FIG. 43 shows a conventional bendable metal nose seal that is disposed within the folds of the mask at a location corresponding to the bridge of a user's nose. FIG. 44 shows a replaceable adhesive nose strip that is disposed on the outside of the folds of the mask at a location corresponding to the bridge of a user's nose, and FIG. 45 shows the components of a magnetic removable nose seal.

Figure 46:
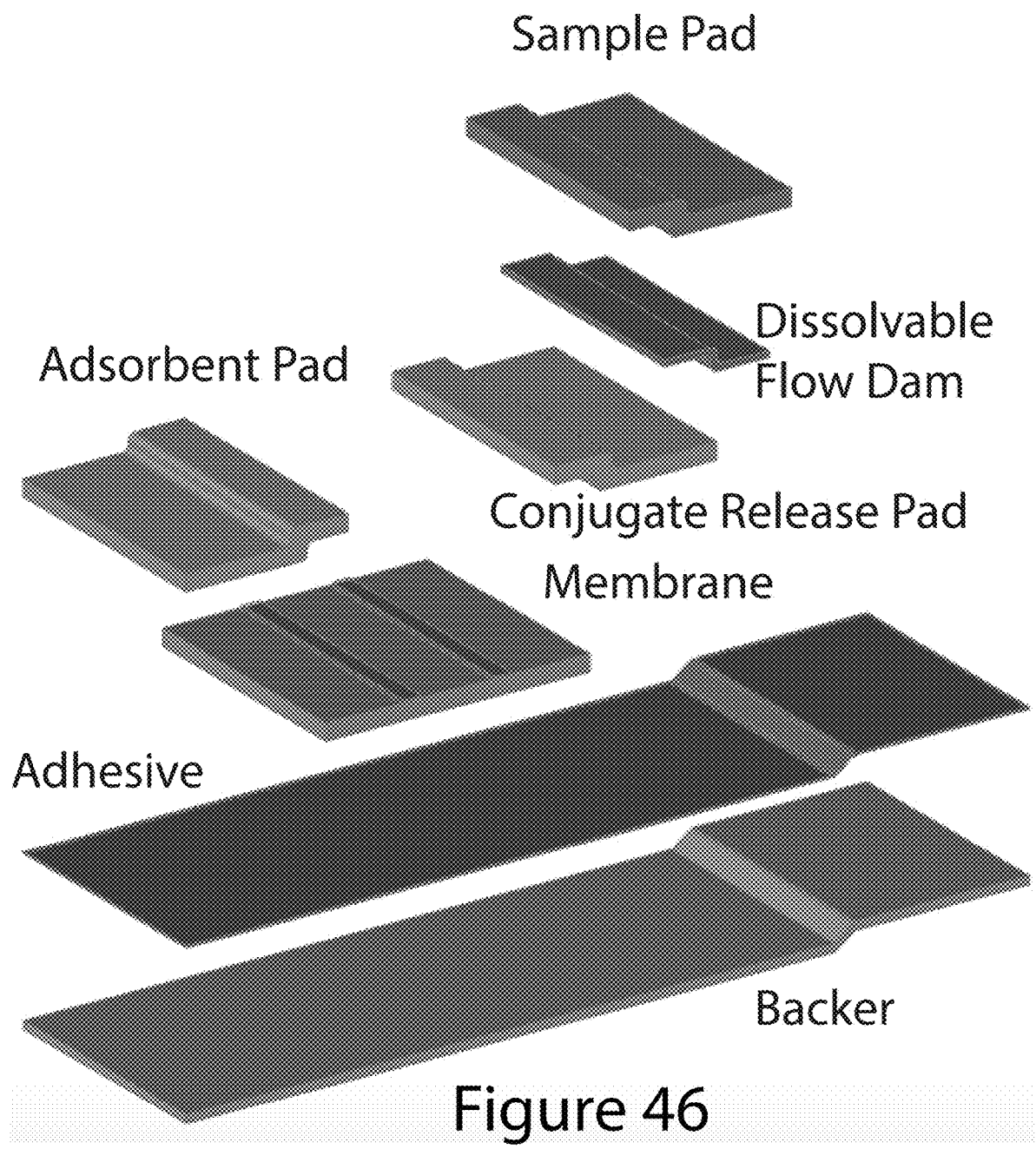
FIG. 46 is an exploded view of a testing system including a dissolvable flow dam that holds back collected EBC on the sample pad until enough has been accumulated to be released onto the conjugate release pad and flush the fluid sample through the components of the testing system.

FIG. 46 is an exploded view of a testing system including a dissolvable flow dam that holds back collected EBC on the sample pad until enough has been accumulated to be released onto the conjugate release pad and flush the fluid sample through the components of the testing system. A fluid dam member may be disposed between the droplet harvesting structure and the biomarker testing zone, wherein the fluid dam member includes at least one of a removable moisture resistant sheet member and a dissolvable film for accumulating the fluid sample from the droplet harvesting structure and releasing the accumulated fluid sample to flow to the biomarker testing zone. The fluid sample testing system comprises a fluidic lateral flow assay including a sample pad for receiving the fluid sample potentially containing a biomarker analyte as the second biomarker, a conjugate release pad, a flow membrane and an adsorbent pad for receiving and flowing the fluid sample to detect the potential biomarker analyte from the sample source. The fluid dam member may be disposed between the sample pad and the conjugate release pad, the fluid dam including a pull tab structure to enable a user to remove the fluid dam member and allow the flow of the fluid sample from the sample pad to the conjugate release pad. At least one photoemitter and one photodetector may be provided, wherein the photoemitter emits radiation towards the biomarker testing zone and the photodetector receives radiation from the biomarker testing zone.

Figure 47:
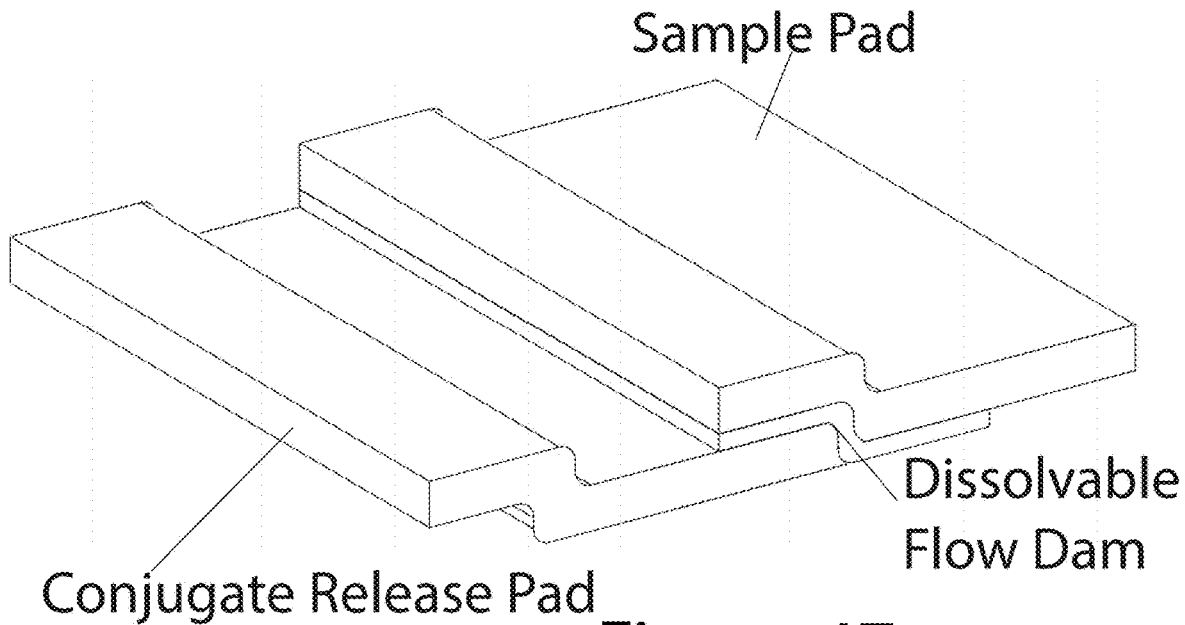
FIG. 47 is an isolated view showing the dissolvable flow dam inserted between the sample pad and the conjugate release pad.
Figure 48:
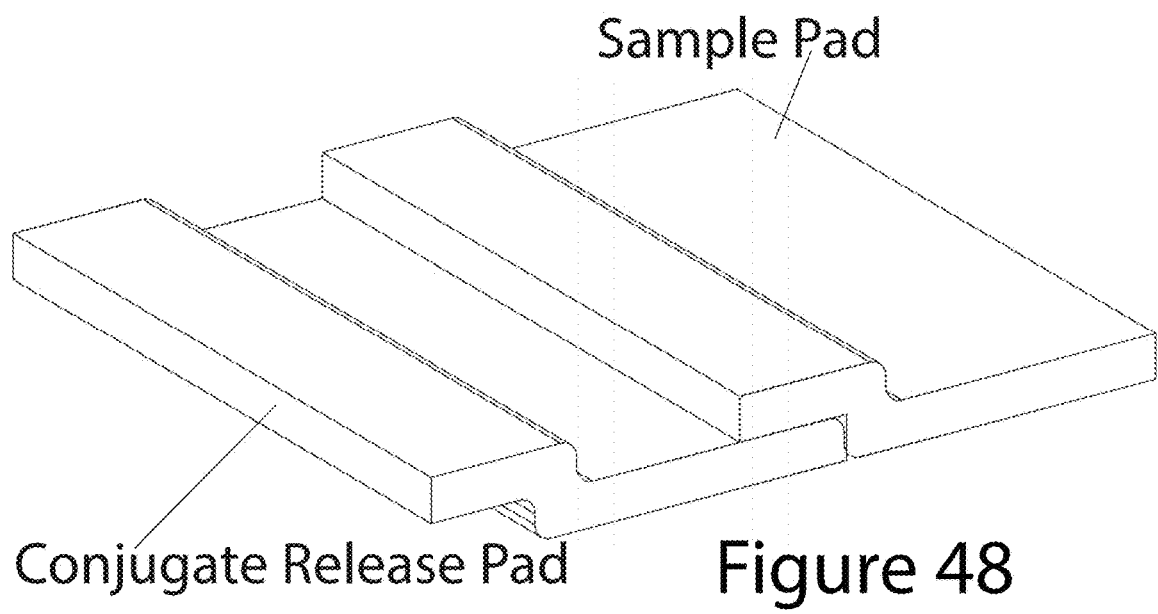
FIG. 48 is an isolated view showing after the dissolvable flow dam has been dissolved away to release the accumulated fluid sample from the sample pad to the conjugate release pad.
Figures 49, 50, 51:
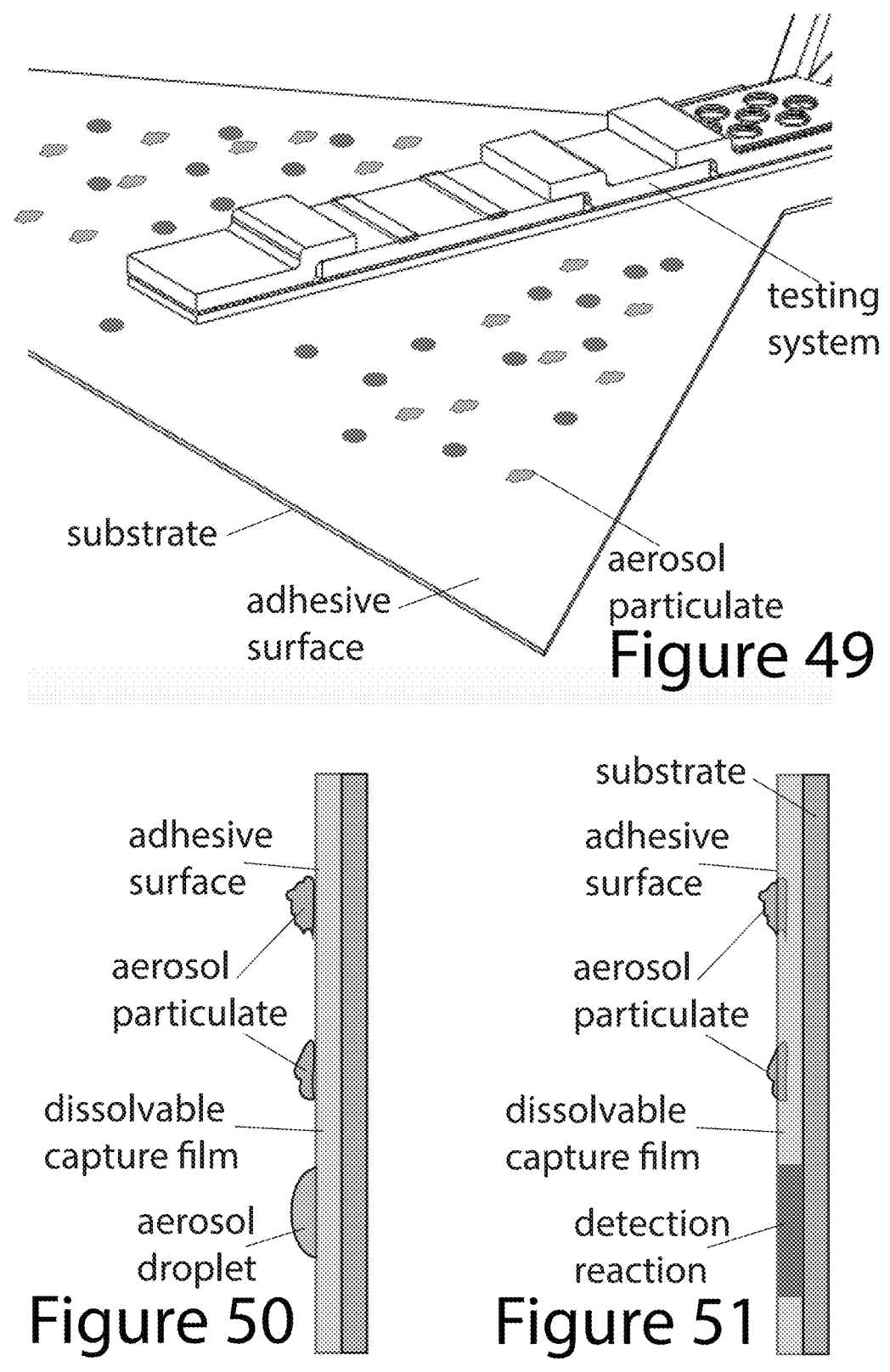

FIG. 47 is an isolated view showing the dissolvable flow dam inserted between the sample pad and the conjugate release pad. FIG. 48 is an isolated view showing after the dissolvable flow dam has been dissolved away to release the accumulated fluid sample from the sample pad to the conjugate release pad. The inventive at-home testing system can be used for COVID-19, other virus, bacterial, environment, cancer, asthma, diabetes, fitness, or other medical use-case. The basic premise is to collect Exhaled Breath Condensate (EBC) and Exhaled Breath Aerosols (EBA) using a face mask. The EBC is collected through a hydrophobic/hydrophilic droplet harvesting structure and channeled onto a testing system (e.g., Lateral Flow Assay or Electronic Biosensor). To effectively collect and accumulate EBC, a dissolvable material may be used for regulating capillary fill time. This allows holding back the flow of the liquid sample (EBC) from the droplet harvesting structure until enough sample is accumulated to flush the liquid via capillary action through the test system. For capturing EBA, suspending droplets and aerosol particulate on the surface or into a film of a dissolvable film can be used where the surface of the film is tacky so that exhaled particulate during breathing or coughing will stick to the adhesive surface. If the film is also water soluble, breath droplet will also be adsorbed into the film. This COVID-19 testing system can be deployed for using EBC for screening (that is, a go/no-go triage test) and if the EBC test indicates a positive detection of a target biomarker (e.g., COVID-19 antibody or RNA), then the mask is shipped to a testing lab where the captured EBA is analyzed FIG. 49 is an isolated view showing a dissolvable EBC droplet and EBA particulate collector. FIG. 50 is a cross section side view showing a section of the dissolvable droplet and particulate collector having particulate and droplets impinged on the surface. In an enhanced version of the proposed testing system an aerosol particulate collection system is provided to capture virus biomarkers exhaled or coughed by the test subject. The surfaces in all parts of the lung down to the alveoli are coated with an aqueous mucous layer that can be aerosolized and carry along a variety of non-volatile constituents. EBC and EBA are different types of breath matrices used to assess human health and disease state. EBA represents a fraction of total EBC, and is targeted to larger molecules, such as fatty acids and cytokines, as well as cellular fractions, proteins, viruses, and bacteria instead of the gas-phase (see, Wallace M A G, Pleil J D. Evolution of clinical and environmental health applications of exhaled breath research: Review of methods and instrumentation for gas-phase, condensate, and aerosols. *Anal Chim Acta.* 2018; 1024:18-38. doi:10.1016/j.aca.2018.01.069).

Figure 52:
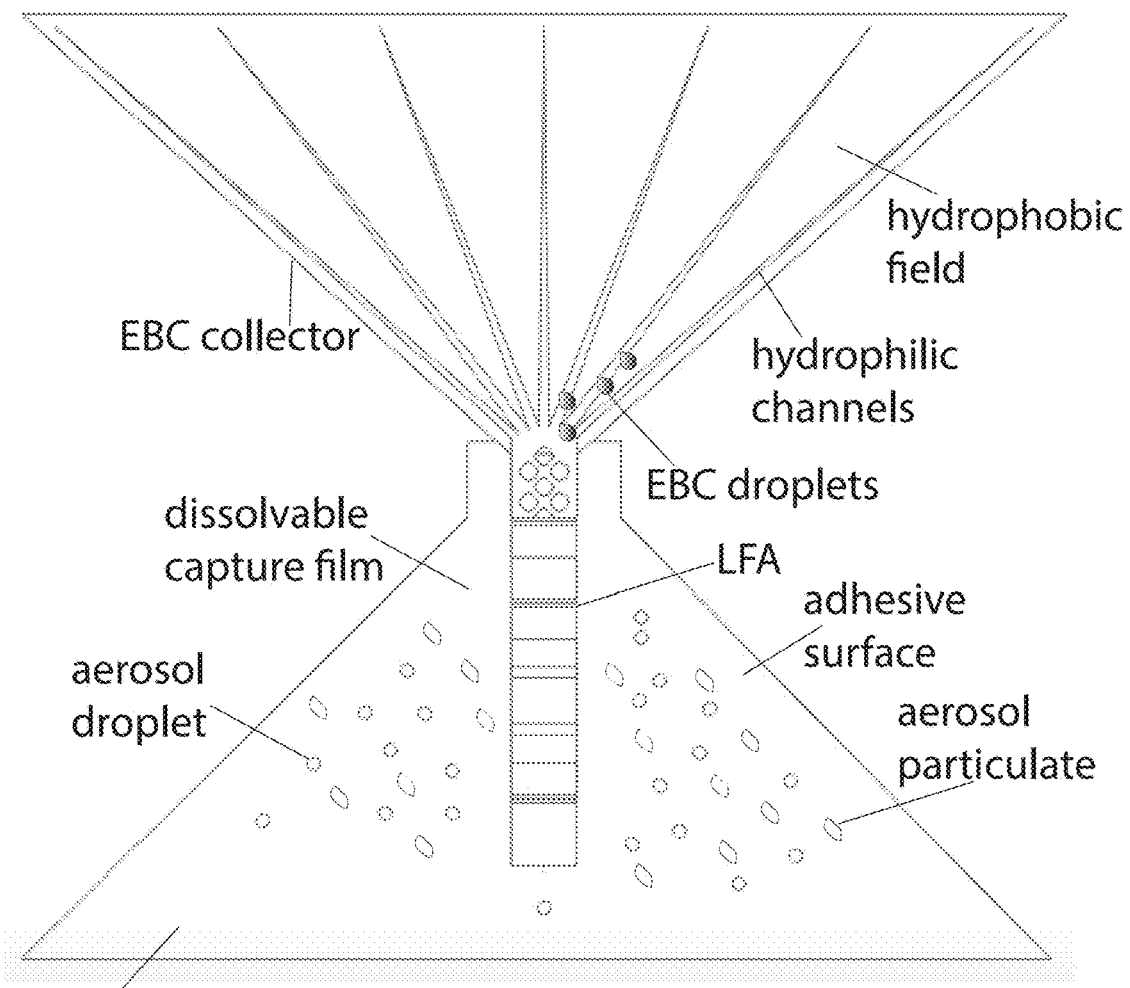
FIG. 52 is a top view showing the inventive testing system including a dissolvable EBC droplet and EBA particulate collector having captured aerosol droplets and aerosol particulate.

FIG. 51 is a cross section side view showing the section of the dissolvable droplet and particulate collector having particulate embedded into the dissolvable capture film and droplets dissolved into and causing a detection reaction with a detection reagent of the dissolvable capture film. FIG. 52 is a top view showing the inventive testing system including a dissolvable EBC droplet and EBA particulate collector having captured aerosol droplets and aerosol particulate. The particulate capture mechanism can be dissolvable film that has a sticky surface and may include a visual detection reaction to one or more target biomarkers. A soluble biomarker that reacts with the visual detection chemical generates a visual indication of the biomarker presences in the EBA. A non-soluble particulate is captured on the sticky surface and becomes embedded into the capture film so it can be easily shipped to a lab for analysis. As an example, if the EBC testing system is used for at-home screening, a positive test result for the EBC target biomarker can be used to prompt the test subject to mail back the testing system so that the captured particulate from the EBA sample can be further analyzed with more sophisticated laboratory equipment.

The inventive system for detecting a biological agent from the breath of a test subject comprises an exhaled breath condensate droplet harvester for coalescing breath vapor into droplets to form a fluid biological sample, a testing system for receiving the fluid biological sample from the breath droplet harvester and testing for a target analyte, and a wireless communication electronic circuit for detecting a result of the testing for the target analyte and communicating the result to a wireless receiver.

An exhaled breath aerosol capture system can be provided comprising a sheet member having a surface for receiving exhaled breath aerosol comprising at least one of a particulate and a droplet. The surface can be non-soluble, pressure sensitive adhesive or an exposed portion of a dissolvable film formed on, coated, adhered to or integral with the sheet member. The dissolvable film has a composition effective for receiving and capturing the at least one of a particulate and a droplet by at least one of embedding or dissolving the at least one of a particulate and a droplet onto the surface or into the dissolvable film.

At least one of the surface and the dissolvable film includes a reagent for reacting with the at least one particulate and droplet for detecting for the presence of a target analyte in the at least one particulate and droplet.

Figure 53:
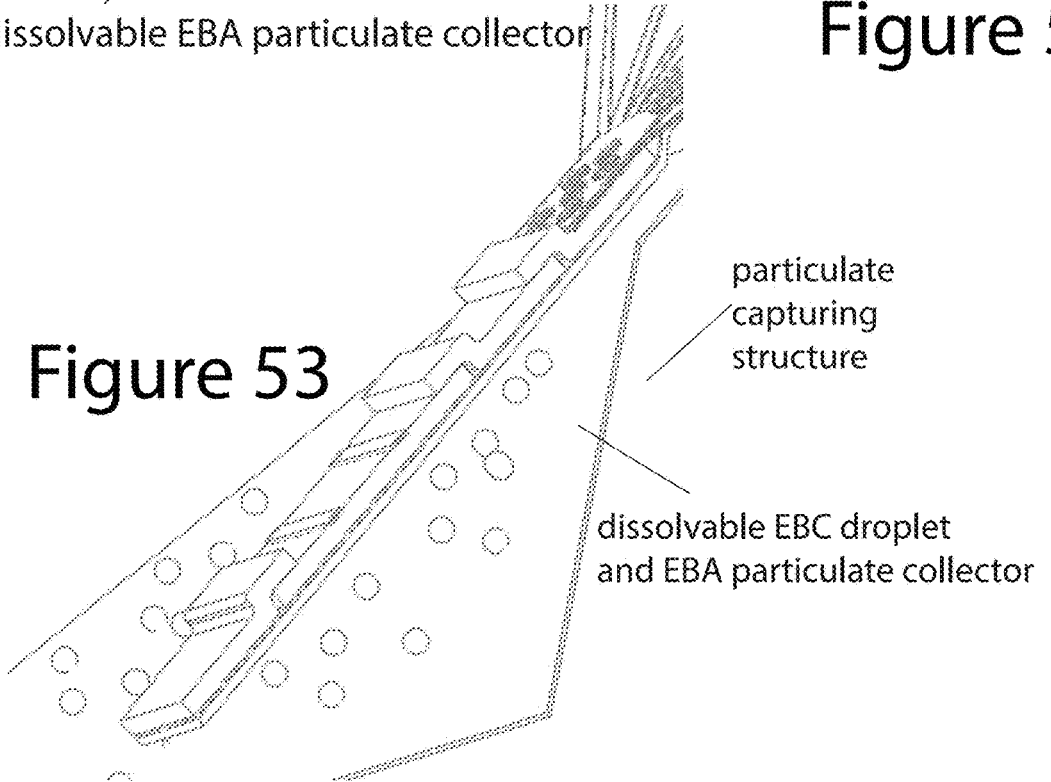
FIG. 53 is an isolated perspective view showing the dissolvable EBC droplet and EBA particulate collector having captured aerosol droplets and aerosol particulate.

FIG. 53 is an isolated perspective view showing the dissolvable EBC droplet and EBA particulate collector having captured aerosol droplets and aerosol particulate. FIG. 54 is a top view showing the inventive testing system including a dissolvable EBC droplet and EBA particulate collector before capturing aerosol droplets and aerosol particulate. FIG. 55 is a top view showing the inventive testing system including a dissolvable EBC droplet and EBA particulate collector after capturing aerosol droplets and aerosol particulate.

Figures 56, 57, 58:
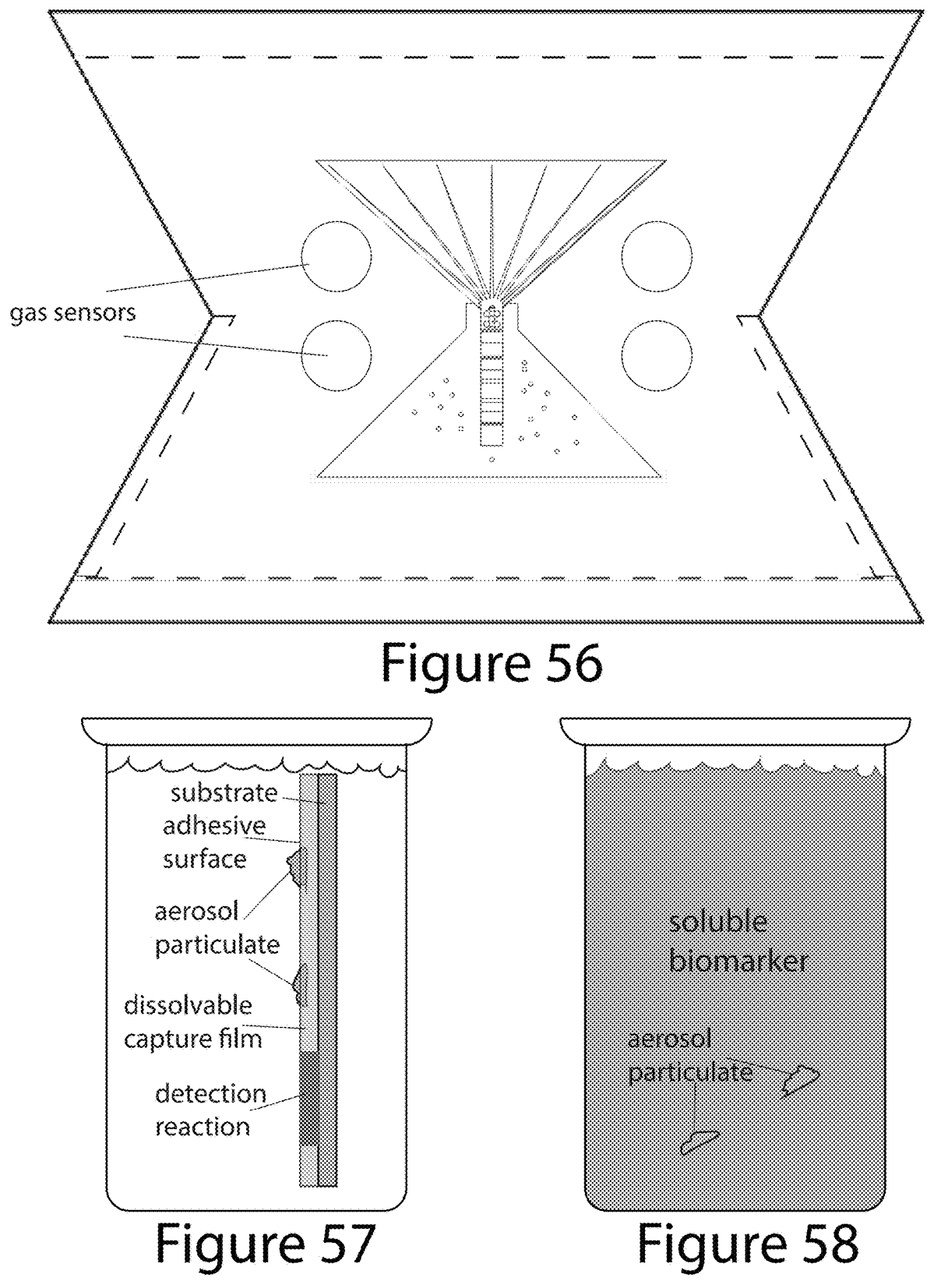

In a further enhanced version of the proposed COVID-19 test system, a nano sensor array can be included along with the EBC and/or EBA collection systems to also test for VOCs, nitric oxide and other gaseous biomarkers specific to virus and/or accompanying changes in the body in response to exposure to COVID-19. FIG. 56 is a top view showing the inventive testing system including a dissolvable EBC droplet and EBA particulate collector installed onto a face mask substrate along with a plurality of gas sensors for detecting volatile and gas constituents of the exhaled breath and/or ambient atmosphere. A common feature of the inflammatory response in patients who have actually contracted influenza is the generation of a number of volatile products of the alveolar and airway epithelium. These products include a number of volatile organic compounds (VOCs) and nitric oxide (NO). These may be used as biomarkers to detect the disease. A research team has shown that a portable 3-sensor array microsystem-based tool can detect flu infection biomarkers (see, for example, Gouma P I, Wang L, Simon S R, Stanacevic M. Novel Isoprene Sensor for a Flu Virus Breath Monitor. *Sensors (Basel)*. 2017; 17(1):199. Published 2017 Jan. 20. doi:10.3390/s17010199). The gas sensors can be connected with the same electronics and wireless communication system used by the other biometric detecting capabilities of the inventive testing system.

FIG. 57 is a cross section side view showing a section of the dissolvable droplet and particulate collector having particulate and droplets impinged on the surface placed in a beaker of dissolving liquid. FIG. 58 is a cross section side view showing a section of the dissolvable droplet and particulate collector having the particulate released into and the droplets dissolved into the beaker of dissolving liquid. In a proposed use-case, the inventive testing system can be distributed on a massive scale through the mail or courier systems of a country, state or region. The inventive test system can be incorporated into a mask as shown or provided as a stand alone system that can be easily retrofit into an existing mask. As an alternative to the EBC Droplet Harvester, and alternative mechanism can be used to collect the EBC. For example, in a hospital setting, EBC can be collected from the face mask used to administer oxygen or other gas to a patient. At home, EBC can be collected by exhaling into a chiller tube (not shown) or other breath vapor condensing system.

The dissolvable droplet and particulate collector can be mailed to a testing laboratory where it is analyzed for captured biomarkers. Particulate and/or droplets can be expelled by the test subject through a forced cough, deep airway exhalation, sneeze, or other respiratory maneuver. In a triage or screening procedure, a large number of testing systems can be distributed to a whole population or statistically meaningful sample of the population. If the EBC testing system indicates a likelihood of COVID-19 current or prior infection (or other biological condition), then the entire testing system kit or just the dissolvable droplet and particulate collector can be sent to laboratory for more stringent analysis.

The dissolving liquid used by the laboratory (or other testing facility) for testing for target biomarkers may include reagents that change color, cause precipitation, amplification or otherwise assist in the identification of the target biomarker captured by the dissolvable droplet and particulate collector.

In accordance with a non-limiting exemplary embodiment, a system is provided for detecting a biological agent from the breath of a test subject comprises an exhaled breath condensate droplet harvester for coalescing breath vapor into droplets to form a fluid biological sample, a testing system for receiving the fluid biological sample from the breath droplet harvester and testing for a target analyte, and a wireless communication electronic circuit for detecting a result of the testing for the target analyte and communicating the result to a wireless receiver. An exhaled breath aerosol capture system can be provided comprising a sheet member having a surface for receiving exhaled breath aerosol comprising at least one of a particulate and a droplet. The surface can be non-soluble, pressure sensitive adhesive or an exposed portion of a dissolvable film formed on, coated, adhered to or integral with the sheet member. The dissolvable film has a composition effective for receiving and capturing the at least one of a particulate and a droplet by at least one of embedding or dissolving the at least one of a particulate and a droplet onto the surface or into the dissolvable film. At least one of the surface and the dissolvable film includes a reagent for reacting with the at least one particulate and droplet for detecting for the presence of a target analyte in the at least one particulate and droplet.

Figure 59:
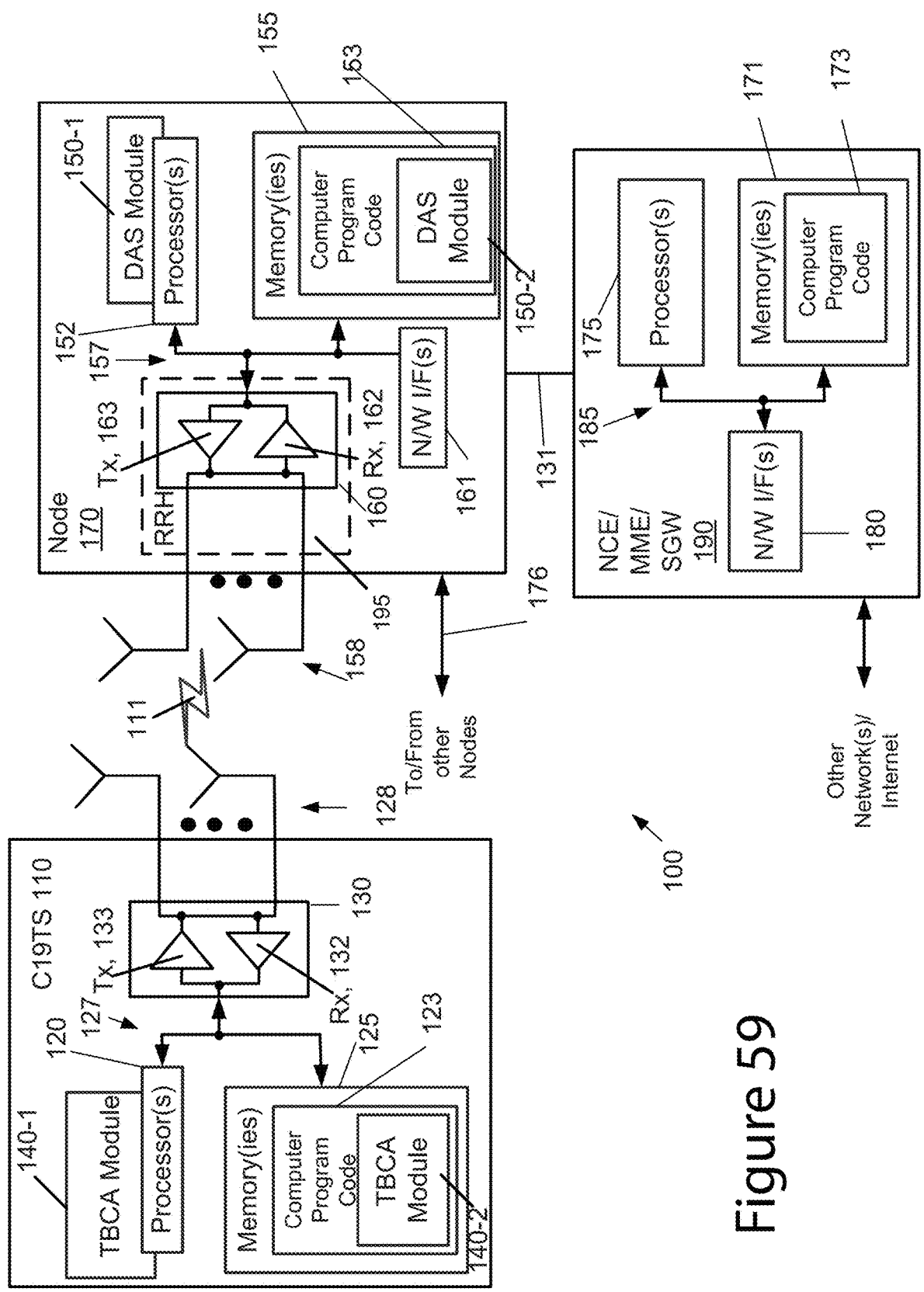
FIG. 59 is a block diagram of one possible and non-limiting exemplary system in which the exemplary embodiments may be practiced.

Turning to FIG. 59, this figure shows a block diagram of one possible and non-limiting exemplary system in which the exemplary embodiments may be practiced. In FIG. 59, a COVID-19 testing system (C19TS) 110 is in wireless communication with a wireless network 100. A C19TS is a wireless COVID-19 testing system that can access a wireless network. The C19TS 110 includes one or more processors 120, one or more memories 125, and one or more transceivers 130 interconnected through one or more buses 127. Each of the one or more transceivers 130 includes a receiver, Rx, 132 and a transmitter, Tx, 133. The one or more buses 127 may be address, data, or control buses, and may include any interconnection mechanism, such as a series of lines on a motherboard or integrated circuit, or other optical communication equipment, and the like. The one or more transceivers 130 are connected to one or more antennas 128. The one or more memories 125 include computer program code 123. The C19TS 110 includes a Target Biomarker Collection and Analysis (TBCA) module 140, comprising the inventive COVID-19 testing system described herein. An embodiment of the TBCA also includes wireless communication capabilities comprising one of or both parts 140-1 and/or 140-2, which may be implemented in a number of ways. The TBCA module 140 may be implemented in hardware as TBCA module 140-1, such as being implemented as part of the one or more processors 120. The TBCA module 140-1 may be implemented also as an integrated circuit or through other hardware such as a programmable gate array. In another example, the TBCA module 140 may be implemented as TBCA module 140-2, which is implemented as computer program code 123 and is executed by the one or more processors 120. For instance, the one or more memories 125 and the computer program code 123 may be configured to, with the one or more processors 120, cause the COVID-19 testing system 110 to perform one or more of the operations as described herein. The C19TS 110 communicates with Node 170 via a wireless link 111.

The Node 170 is a base station (e.g., 5G, 4G, LTE, long term evolution or any other cellular, internet and/or wireless network communication system) that provides access by wireless devices such as the C19TS 110 to the wireless network 100. The Node 170 includes one or more processors 152, one or more memories 155, one or more network interfaces (N/W I/F(s)) 161, and one or more transceivers 160 interconnected through one or more buses 157. Each of the one or more transceivers 160 includes a receiver, Rx, 162 and a transmitter Tx, 163. The one or more transceivers 160 are connected to one or more antennas 158. The one or more memories 155 include computer program code 153. The Node 170 includes a Data Acquisition and Storage (DAS) module 150, comprising one of or both parts 150-1 and/or 150-2, which may be implemented in a number of ways. The DAS module 150 may be implemented in hardware as DAS module 150-1, such as being implemented as part of the one or more processors 152. The DAS module 150-1 may be implemented also as an integrated circuit or through other hardware such as a programmable gate array. In another example, the DAS module 150 may be implemented as DAS module 150-2, which is implemented as computer program code 153 and is executed by the one or more processors 152. For instance, the one or more memories 155 and the computer program code 153 are configured to, with the one or more processors 152, cause the Node 170 to perform one or more of the operations as described herein. The one or more network interfaces 161 communicate over a network such as via the links 176 and 131. Two or more Nodes 170 communicate using, e.g., link 176. The link 176 may be wired or wireless or both and may implement, e.g., an X2 interface.

The one or more buses 157 may be address, data, or control buses, and may include any interconnection mechanism, such as a series of lines on a motherboard or integrated circuit, fiber optics or other optical communication equipment, wireless channels, and the like. For example, the one or more transceivers 160 may be implemented as a remote radio head (RRH) 195, with the other elements of the Node 170 being physically in a different location from the RRH, and the one or more buses 157 could be implemented in part as fiber optic cable to connect the other elements of the Node 170 to the RRH 195.

The wireless network 100 may include a network control element (NCE) 190 that may include MME (Mobility Management Entity)/SGW (Serving Gateway) functionality, and which provides connectivity with a further network, such as a telephone network and/or a data communications network (e.g., the Internet). The Node 170 is coupled via a link 131 to the NCE 190. The link 131 may be implemented as, e.g., an S1 interface. The NCE 190 includes one or more processors 175, one or more memories 171, and one or more network interfaces (N/W I/F(s)) 180, interconnected through one or more buses 185. The one or more memories 171 include computer program code 173. The one or more memories 171 and the computer program code 173 are configured to, with the one or more processors 175, cause the NCE 190 to perform one or more operations.

The wireless network 100 may implement network virtualization, which is the process of combining hardware and software network resources and network functionality into a single, software-based administrative entity, a virtual network. Network virtualization involves platform virtualization, often combined with resource virtualization. Network virtualization is categorized as either external, combining many networks, or parts of networks, into a virtual unit, or internal, providing network-like functionality to software containers on a single system. Note that the virtualized entities that result from the network virtualization are still implemented, at some level, using hardware such as processors 152 or 175 and memories 155 and 171, and also such virtualized entities create technical effects.

The computer readable memories 125, 155, and 171 may be of any type suitable to the local technical environment and may be implemented using any suitable data storage technology, such as semiconductor based memory devices, flash memory, magnetic memory devices and systems, optical memory devices and systems, fixed memory and removable memory. The computer readable memories 125, 155, and 171 may be means for performing storage functions. The processors 120, 152, and 175 may be of any type suitable to the local technical environment, and may include one or more general purpose computers, special purpose computers, microprocessors, digital signal processors (DSPs) and processors based on a multi-core processor architecture, as non-limiting examples. The processors 120, 152, and 175 may be means for performing functions, such as controlling the C19TS 110, Node 170, and other functions as described herein.

In general, the various embodiments of the COVID-19 testing system 110 can include, but are not limited to, wireless communication components used for Bluetooth, cellular telephones such as smart phones, tablets, personal digital assistants (PDAs) having wireless communication capabilities, portable computers having wireless communication capabilities, image capture devices such as digital cameras having wireless communication capabilities, gaming devices having wireless communication capabilities, music storage and playback appliances having wireless communication capabilities, Internet appliances permitting wireless Internet access and browsing, tablets with wireless communication capabilities, as well as portable units or terminals that incorporate combinations of such functions.

Figure 60:
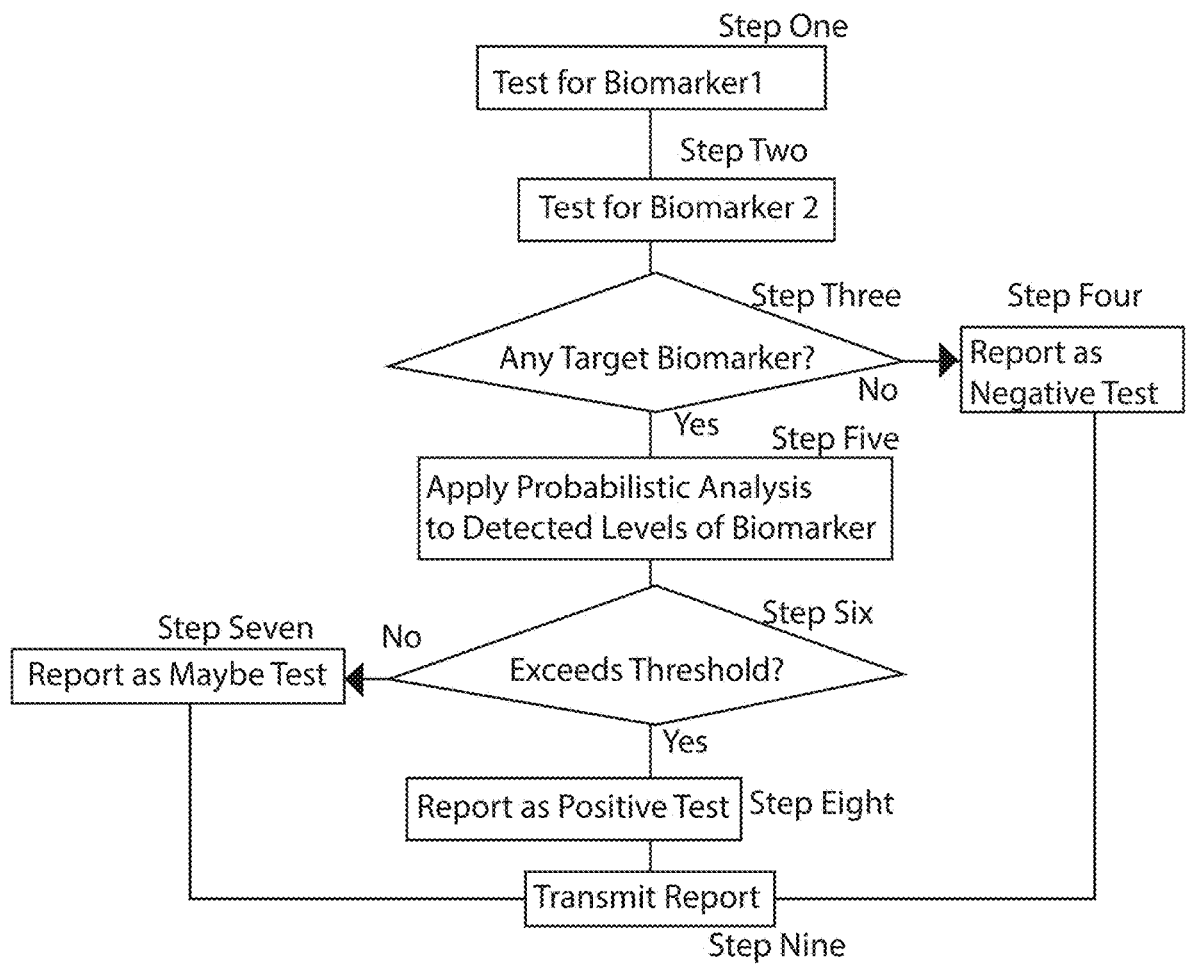
FIG. 60 is a logic flow diagram for Applied Probabilistic Analysis to Determine COVID-19 Exposure, and illustrates the operation of an exemplary method, a result of execution of computer program instructions embodied on a computer readable memory, functions performed by logic implemented in hardware, and/or interconnected means for performing functions in accordance with exemplary embodiments.

FIG. 60 is a logic flow diagram for Applied Probabilistic Analysis to Determine COVID-19 Exposure. This figure further illustrates the operation of an exemplary method, a result of execution of computer program instructions embodied on a computer readable memory, functions performed by logic implemented in hardware, and/or interconnected means for performing functions in accordance with exemplary embodiments. For instance, the TBCA module 140 may include multiples ones of circuit elements for implementing the functions shown in the blocks in FIG. 59, where each included block is an interconnected means for performing the function in the block. At least some of the blocks in FIG. 59 are assumed to be performed by the C19TS 110, e.g., under control of the TBCA module 140 at least in part.

For the applied probabilistic analysis to determine COVID-19 exposure, Biomarker1 is tested (step one), Biomarker1 is tested (step four), and BiomarkerN is tested (step three) where N can be any number of multiple biomarkers tested using the inventive testing system. If no target biomarker is detected (step three) then a Negative Test report is generated (step four). If any target biomarker is detected (step three) then probabilistic analysis may be performed depending simply on the detected presence (yes/no) or quantitative analysis (e.g., concentration) of the one or more detected biomarkers (step five). If the probabilistic analysis does not exceed a threshold (step six) (e.g., low concentration of a particular target biomarker, or the presence of just one weak biomarker indicating likely infection), then a Maybe Test report is generated (step seven). If the probabilistic analysis does exceed a threshold (step six) (e.g., high concentration of a particular target biomarker, or the presence of two or more biomarkers indicating likely infection), then a Positive Test report is generated (step eight). The Test Report is then transmitted (step nine) (e.g., in a manner described herein or other suitable transmission mechanism including verbal, digital, written or other communication transmission).

The logic flow of FIG. 60 is implemented by a non-limiting embodiment of an apparatus, comprises: at least one processor; and at least one memory including computer program code, the at least one memory and the computer program code configured to, with the at least one processor, cause the apparatus to perform at least the following: detecting one or more biometric parameters using a droplet harvesting structure for converting breath vapor to a fluid droplet for forming a fluid sample and a testing system having a biomarker testing zone for receiving the fluid sample and detecting the biometric parameter, where the biometric parameters are biomarkers dependent on at least one physiological change to a patient in response to a concerning condition such as a virus infection; receiving the one or more biometric parameters and applying probabilistic analysis to determine if at least one physiological change threshold has been exceeded dependent on the probabilistic analysis of the one ore more biometric parameters; and activating an action depending on the determined exceeded said at least one physiological change.

In accordance with an embodiment, a digital testing device is provided comprising a biomarker testing device having one or more biometric detectors each for detecting biomarkers as one or more biometric parameters. The biometric parameters are dependent on at least one physiological change to a patient or test subject, such as the production of immune response chemicals, the presence in the body of an active or deactivated virus or virus component, antibodies, antigens, virus RNA or DNA, or other biomarker inducing change. A microprocessor receives the one or more biometric parameters and determines if at least one physiological change threshold has been exceeded dependent on the one or more biometric parameters. An activation circuit activates an action depending on the determined physiological change. The action includes at least one of transmitting an alert, modifying a therapeutic treatment, and transmitting data dependent on at least one physiological change, the one or more biometric parameters, and the therapeutic treatment.

The at least one physiological change can also be in response to an applied therapeutic treatment that is at least one of a pharmaceutical treatment and an electroceutical treatment that causes a change in the condition of the patient enabling the monitoring of the body's response to the applied therapeutic. The action can include transmitting an alert, modifying a therapeutic treatment, and transmitting data dependent on at least one of the at least one physiological change, the one or more biometric parameters, and the therapeutic treatment. The microprocessor can analyze the one or more biometric parameters using probabilistic analysis comprising determining from a data set of the one or more biometric parameters whether the data set is acceptable for deciding that the at least one physiological change threshold has been exceeded. The probabilistic analysis can further comprise applying a statistical weighting to each of the one or more biometric parameters, where the statistical weighting is dependent on a predetermined value of a ranking of importance in detecting each of the at least one physiological change for said each of the one or more biometric parameters relative to others of the one or more biometric parameters.

Figure 61:
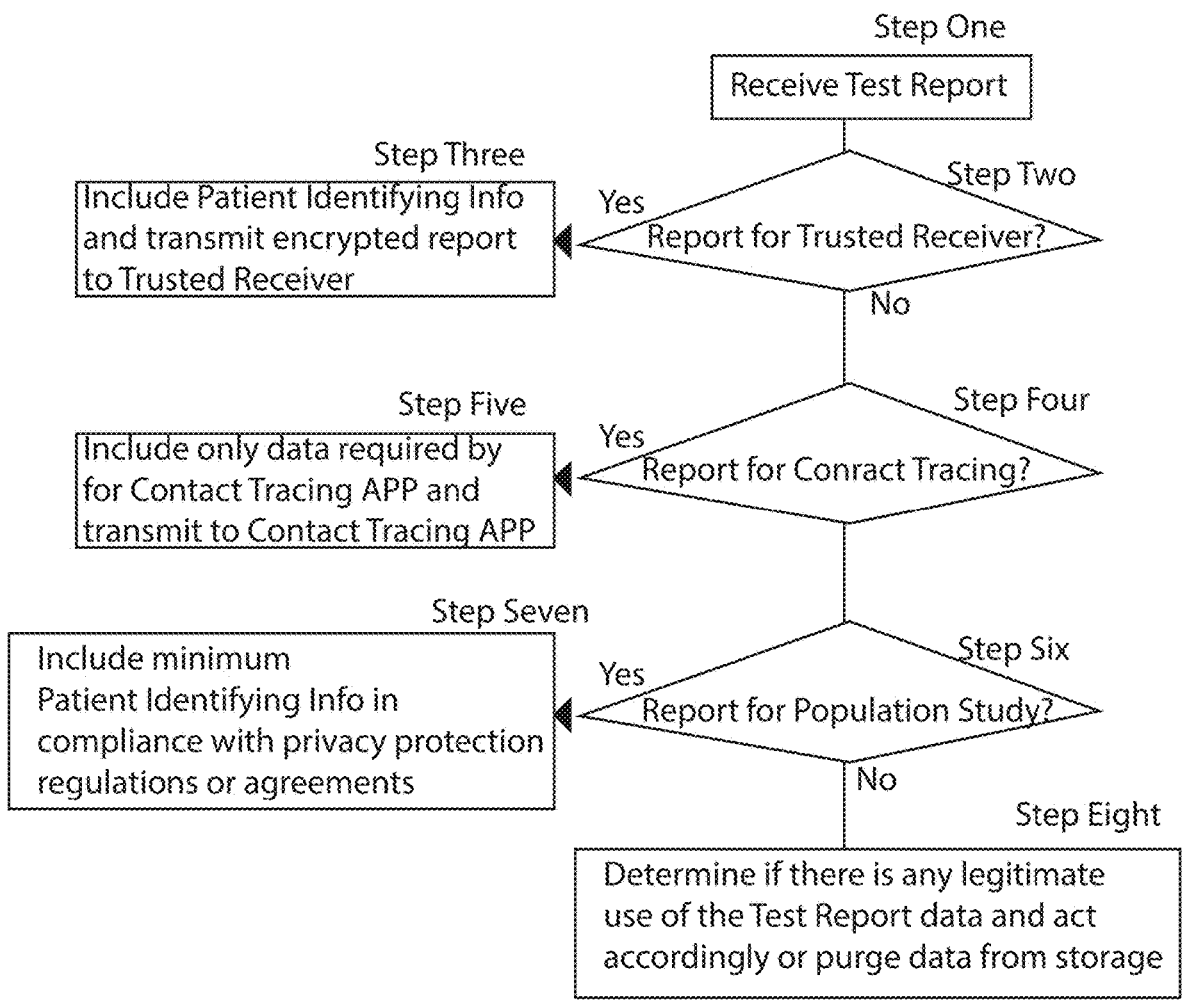
FIG. 61 is a logic flow diagrams for Data Acquisition and Transmission for Trusted Receiver and Contract Tracing Uses, and illustrate the operation of an exemplary method, a result of execution of computer program instructions embodied on a computer readable memory, functions performed by logic implemented in hardware, and/or interconnected means for performing functions in accordance with exemplary embodiments.

FIG. 61 is a logic flow diagram for Data Acquisition and Transmission for Trusted Receiver and Contract Tracing Uses. This figure further illustrates the operation of an exemplary method, a result of execution of computer program instructions embodied on a computer readable memory, functions performed by logic implemented in hardware, and/or interconnected means for performing functions in accordance with exemplary embodiments. The performance of the Data Acquisition and Transmission for Trusted Receiver and Contract Tracing Uses flow can be done at the testing system, Node, Smartphone, or combination of components located or associated with the test subject through the end user(s) or final storage location(s) of the acquired data. The acquired data can include patient or subject identifying information ranging from name, GPS location, list of known contacts, prior medical history, demographics, etc. The Data Acquisition and Transmission for Trusted Receiver and Contract Tracing Uses can be done at a secure server located anywhere on the network. For instance, the DAS module 150 may include multiples ones of circuit elements for implementing the functions shown in the blocks in FIG. 59, where each included block is an interconnected means for performing the function in the block. At least some of the blocks in FIG. 59 are assumed to be performed by a base station such as Node 170, e.g., under control of the DAS module 150 at least in part.

The digital testing system architecture, manufacturing methods, and applications, can be used for capturing biometric data from the exhaled breath of a test subject or patient. Biometric data can be captured and transmitted continuously or at selected times with data access provided directly to a care-provider, enabling early diagnosis and ongoing monitoring, and to a researcher to gain valuable insights and assistance through AI analysis. This data detection is direct from the exhaled breath and can be provided through a wireless connection for Blockchain and AI database collection, access and analysis. The inventive digital testing system for biometric capture is adapted to mass production as a roll-to-roll manufactured testing device with embedded sensors and transducers.

The Test Report is received (step one) (e.g., from a Smartphone transmission from the patient or test subject). If the report is intended to be sent to a trusted receiver (step two), such as a patient's healthcare provider or insurance company, then an encrypted report can be generated (step three) and transmitted to the trusted receiver that includes patient identifying information. If the report is not for a trusted receiver (step two) but instead is to be used for contact tracing (step four), then only the data required for Contact Tracing is transmitted to a Contact Tracing APP (step five). The Contact Tracing APP may be, for example, a system provided for identifying and notifying people who have come in contact with the test subject or patient within a given time prior or since testing positive or may be for one or more target biomarkers. If the report is not for a trusted receiver (step two) or for contact tracing (step four) but instead is to be used for a population study (step six), then only the minimum patient identifying information in compliance with privacy regulations and/or agreements is transmitted and/or stored along with the received test report (step seven). If the report is not for a trusted receiver, contact tracing or population study (step six) then it is determined if there is any legitimate use of the test report data and an action is taken accordingly or the automatically data is purged from storage.

Figure 62:
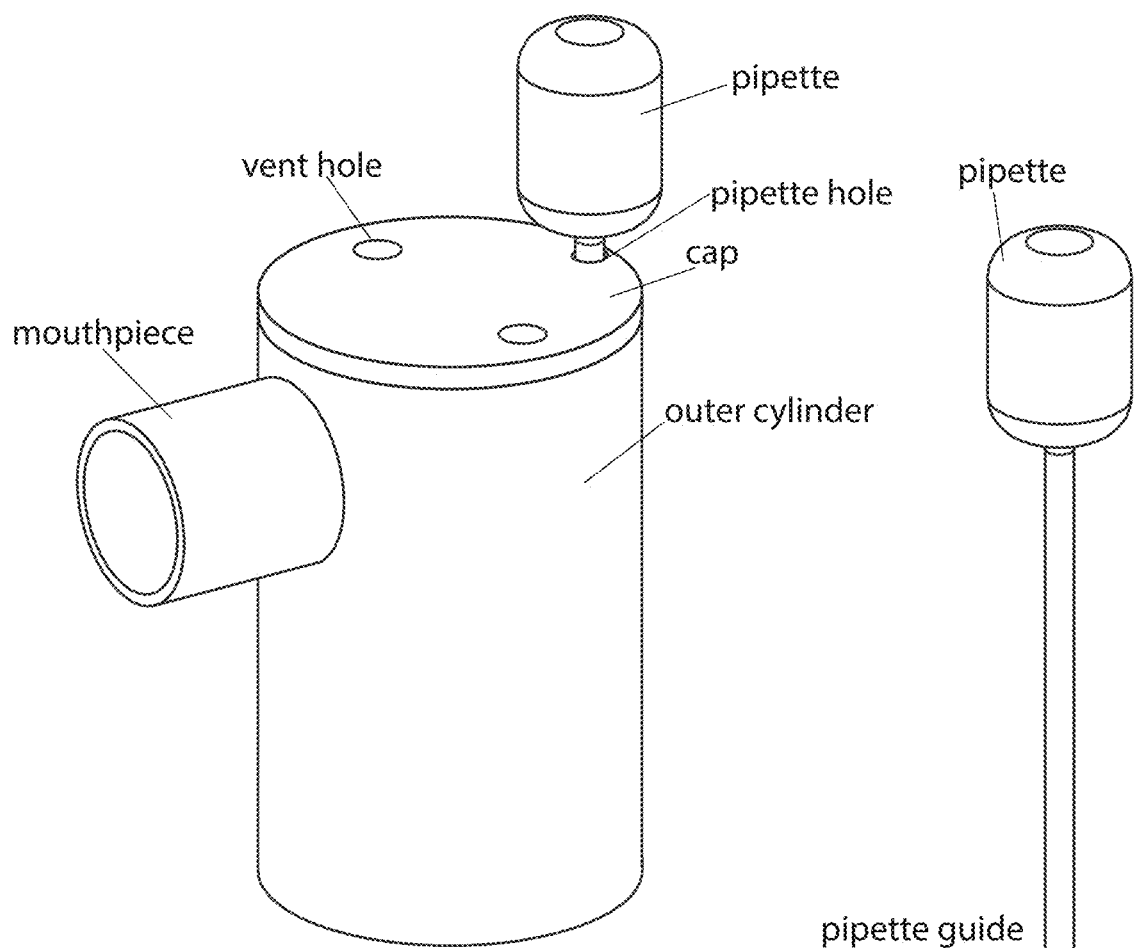
FIG. 62 is a perspective view of an embodiment of a EBC/EBA collection system.
Figure 63:
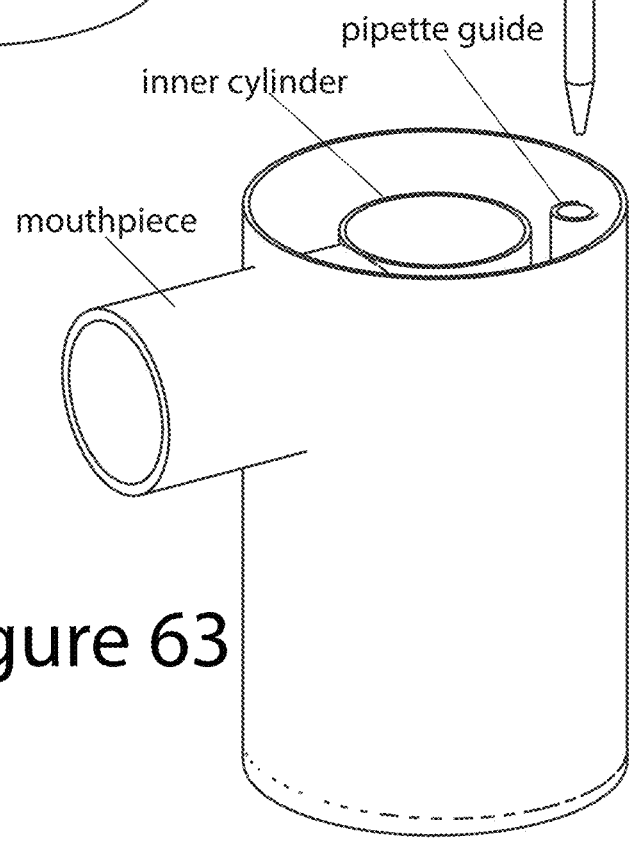
FIG. 63 is a perspective view of the EBC/EBA collection system showing a pipette and pipette guide.
Figure 66:
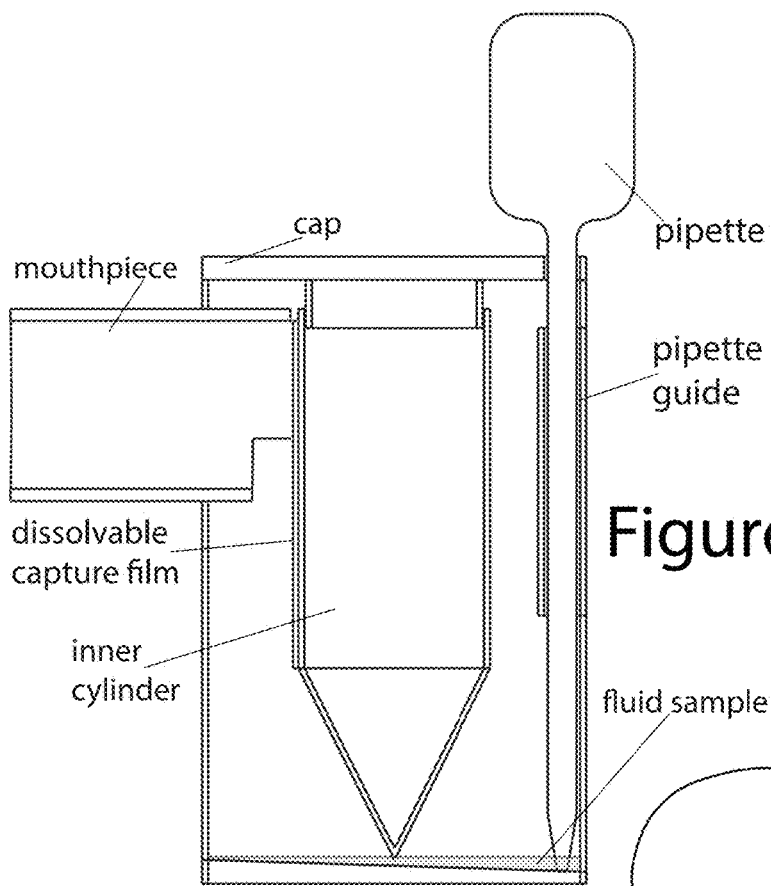
FIG. 66 is a cross-sectional view of the EBC/EBA collection system.
Figure 67:
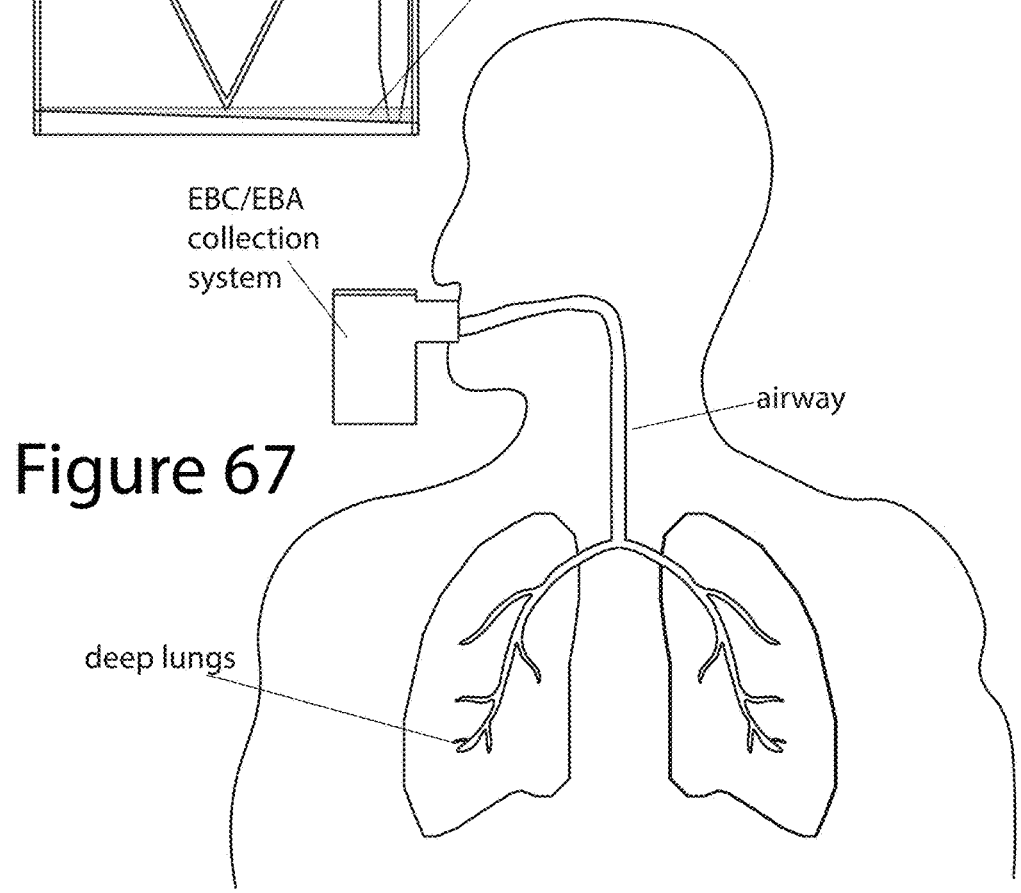
FIG. 67 illustrates the use of the EBC/EBA collection system for obtaining biomarker samples from the lungs of a user.

FIG. 62 is a perspective view of an embodiment of a EBC/EBA collection system. FIG. 63 is a perspective view of the EBC/EBA collection system showing a pipette and pipette guide. FIG. 64 is an exploded view showing the constituent parts of the embodiment of the EBC/EBA collection system. FIG. 65 is another exploded view showing the constituent parts of the EBC/EBA collection system. FIG. 66 is a cross-sectional view of the EBC/EBA collection system. FIG. 67 illustrates the use of the EBC/EBA collection system for obtaining biomarker samples from the lungs of a user.

In accordance with an aspect of the invention, an apparatus for detecting a biomarker includes a particulate capturing structure for receiving and capturing exhaled breath aerosol (EBA) particulate from airway linings of a user, the particulate capturing structure having an aerosol particulate testing system for receiving the captured particulate and detecting a first biomarker, wherein the aerosol particulate testing system includes a dissolvable EBA sample collector film for capturing EBA particulate. The first reagent is bound to a first nanoparticle and held in place at the insoluble testing area. The EBA particulate includes non-soluble particulates and droplet particulates, and the dissolvable EBA collector film includes a tacky surface for adhering to and capturing the non-soluble particulates and water soluble bulk for capturing droplet particulates.

A droplet harvesting structure may be provided for converting breath vapor from a user to an exhaled breath condensate (EBC) fluid droplet for forming a fluid sample. The user exhales through a mouthpiece so that the exhaled breath impinges on the walls of an inner cylinder. The inner cylinder can include a thermal mass (e.g., made for aluminum or other suitable material, or include an inner space that can be fulled with a cold thermal mass). The walls of the inner cylinder receives the breath vapor and forms the fluid droplet from the received breath vapor. The inner cylinder ends in a sharp point to help channel the fluid droplet towards a sloped base. The sloped bass is the end of an outer cylinder that collects that fluid sample from the inner walls of the outer cylinder and the outwalls of the inner cylinder. A pipette passes through a pipette hole in a cap and is used to draw the accumulated fluid sample from the sloped base. Using the pipette, the user expels drops of the fluid sample onto a fluid sample testing system having a biomarker testing zone for receiving the fluid sample and detecting a second biomarker. The cap may also include diverting structures to help keep the breath vapor in contact with the walls of the inner cylinder. All or parts of the system can be integrally formed from an injection mold, or separate parts assembled into the completed system. The entire system or just the inner cylinder can be placed in a freezer ahead of the use to facilitate droplet collection from the chilled walls that come in contact with the breath vapor.

FIG. 68 is an isolated view showing the mouthpiece, cap, base, dissolvable EBA sample collector and inner cylinder of the embodiment of the EBC/EBA collection system. FIG. 69 is an isolated view showing the dissolvable EBA sample collector and inner cylinder having captured EBA particles and droplets. FIG. 70 shows the inner cylinder submersed in a solvent for dissolving the dissolvable EBA sample collector to acquire the captured EBA particles and droplets for biomarker testing.

FIG. 71 is an isolated view of a section of an embodiment of the dissolvable EBA sample collector forming an aerosol particulate testing system having captured EBA particulate, insoluble testing areas and dissolvable capture film areas. The dissolvable EBA sample collector film includes a first reagent for reacting with at least one constituent of the captured particulate in a detection reaction for detecting the first biomarker. The detection reaction generates at least one of a change in an optical signal and an electrical signal dependent on the first biomarker. The detection reaction can in situ, so that with very closely spaced dissolvable and insoluble test areas, the EBA droplets dissolve into the dissolvable film where an analyte in the droplet is picked up, for example, by a labeled-antibody to form an analyte-labeled antibody complex that is bound to capture antibodies and retained at the non-soluble test areas for visual or phontonics detection (similar to the action of a Lateral Flow Assay as described herein). In this case, FIG. 72 shows a series of side views of the embodiment of the dissolvable EBS sample collector capturing EBA droplets and/or particulate showing the aerosol particulate testing system with target analytes captured and bound to the insoluble testing areas. Alternatively, the captured EBA particulate and droplets can be sent in for analysis by a lab where a technician or automated system rinses the dissolvable film to provide a fluid sample that includes the captured EBA analytes. For example, the inner cylinder can be rinsed with a flow or submersed in a solvent for dissolving the dissolvable EBA sample collector to acquire the captured EBA particles and droplets for biomarker testing.

Figure 73:
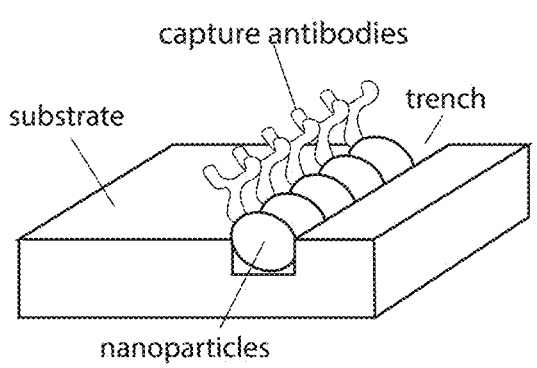
FIG. 73 shows nanoparticles held in a trench in a substrate where the nanoparticles include capture antibodies or other reagent fixed to them.

FIG. 73 shows nanoparticles held in a trench in a substrate where the nanoparticles include capture antibodies or other reagent fixed to them. In this case, the fluid sample testing system may comprise a fluidic biosensor for receiving the fluid sample potentially containing a biomarker analyte as the second biomarker and including a sample source having a biomarker analyte, a bioreceptor area functionalized with an analyte-specific bioreceptor, and a transducer for generating a readable signal depending on a change in the bioreceptor in response to receiving the biomarker analyte from the sample source. The analyte-specific biomarker includes a reagent for creating a detection reaction with the biomarker analyte and where the fluidic biosensor generates at least one of a change in an optical signal and an electrical signal dependent on the biomarker. The reagent is bound to a nanoparticle and held in place at the insoluble testing area.

Figure 74:
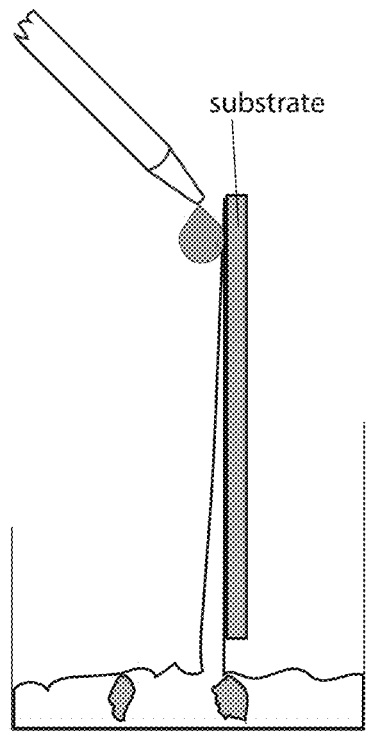
FIG. 74 shows the EBA particles and droplets being rinsed from the dissolvable EBA sample collector to form a fluid sample that includes any biomarker analytes contained in the particles or droplets.

FIG. 74 shows the EBA particles and droplets being rinsed from the dissolvable EBA sample collector to form a fluid sample that includes any biomarker analytes contained in the particles or droplets. This can be done by the user using a solution that includes a buffer and surfactant (and other materials, or these materials may be included in the dissolvable film). This can also be done at a laboratory by a technician or automated equipment.

Figure 75:
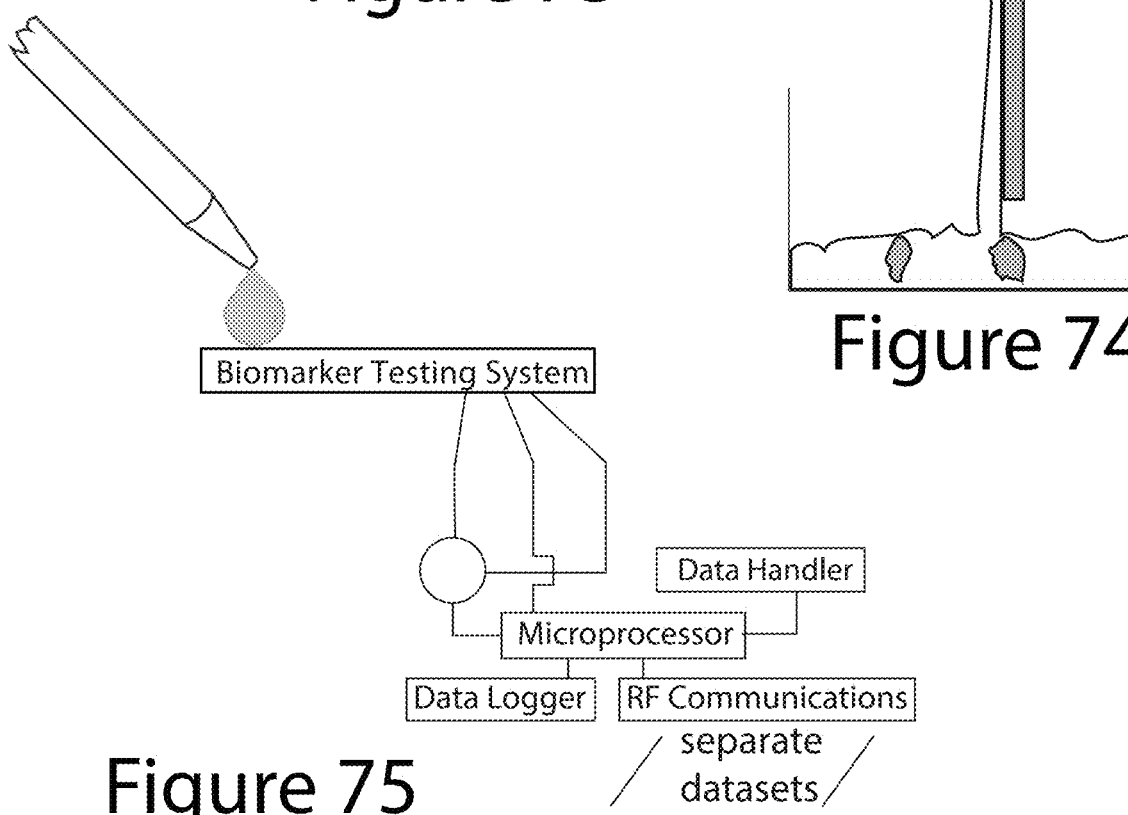
FIG. 75 illustrates the EBA/EBC testing system with a wireless communication electronic circuit that detects a result of the testing for at least one of the first and second biomarker and communicating the result to a wireless receiver.

FIG. 75 illustrates the EBA/EBC testing system with a wireless communication electronic circuit that detects a result of the testing for at least one of the first and second biomarker and communicating the result to a wireless receiver. The wireless communication electronic circuit in communication with at least one of the aerosol particulate testing system and the fluid sample testing system for detecting one or more biometric parameters, where the biometric parameters are dependent on at least one physiological change to a patient in response to a concerning condition such as a virus infection where the one or more biometric parameters are received and probabilistic analysis applied by a microprocessor to determine if at least one physiological change threshold has been exceeded dependent on the probabilistic analysis of the one ore more biometric parameters and where the electronic circuit transmits a signal depending on the determined exceeded said at least one physiological change.

In accordance with another aspect of the invention an apparatus comprises at least one processor, at least one memory including computer program code, the at least one memory and the computer program code configured to, with the at least one processor, cause the apparatus to perform at least the following: detecting one or more biometric parameters using a particulate capturing structure for receiving and capturing exhaled breath aerosol (EBA) particulate from airway linings of a user, the particulate capturing structure having an aerosol particulate testing system for receiving the captured particulate and detecting a first biomarker, wherein the aerosol particulate testing system includes a dissolvable EBA sample collector film for capturing EBA particulate, where the biometric parameters are biomarkers dependent on at least one physiological change to a patient in response to a concerning condition such as a virus infection; receiving the one or more biometric parameters and applying probabilistic analysis to determine if at least one physiological change threshold has been exceeded dependent on the probabilistic analysis of the one ore more biometric parameters; and activating an action depending on the determined exceeded said at least one physiological change. The one or more biometric parameters can be further detected using a droplet harvesting structure for converting breath vapor to a fluid droplet for forming a fluid sample and a testing system having a biomarker testing zone for receiving the fluid sample and detecting the biometric parameter; and wherein the probabilistic analysis is applied to the one or more biometric parameters to determine if the at least one physiological change threshold has been exceeded dependent on the probabilistic analysis of the one ore more biometric parameters detected from both the captured particulates and the fluid sample.

Various modifications and adaptations to the foregoing exemplary embodiments of this invention may become apparent to those skilled in the relevant arts in view of the foregoing description, when read in conjunction with the accompanying drawings. However, any and all modifications will still fall within the scope of the non-limiting and exemplary embodiments of this invention.

The embodiments described herein are intended to exemplary and non-limiting, the selection of biometric, environmental, or other measured conditions is not limited to a specific metric or multiple metrics described herein but will depend on the particular application and treatment, data collection, and/or other use of the detected metrics. Also, the treatments employed in any of the embodiments described herein is not limited to a specific treatment or action but will depend on the intended use and desired outcome of the combined detected metrics and applied treatments.

Furthermore, some of the features of the various non-limiting and exemplary embodiments of this invention may be used to advantage without the corresponding use of other features. As such, the foregoing description should be considered as merely illustrative of the principles, teachings and exemplary embodiments of this invention, and not in limitation thereof. Various modifications and adaptations to the foregoing exemplary embodiments of this invention may become apparent to those skilled in the relevant arts in view of the foregoing description, when read in conjunction with the accompanying drawings. However, any and all modifications will still fall within the scope of the non-limiting and exemplary embodiments of this invention.

The embodiments described herein are intended to exemplary and non-limiting, the selection of biometric, environmental, or other measured conditions is not limited to a specific metric or multiple metrics described herein but will depend on the particular application and treatment, data collection, and/or other use of the detected metrics. Also, the treatments employed in any of the embodiments described herein is not limited to a specific treatment or action but will depend on the intended use and desired outcome of the combined detected metrics and applied treatments.

Furthermore, some of the features of the various non-limiting and exemplary embodiments of this invention may be used to advantage without the corresponding use of other features. As such, the foregoing description should be considered as merely illustrative of the principles, teachings and exemplary embodiments of this invention, and not in limitation thereof.

What is claimed is:

1. Apparatus for diagnostic testing, comprising:
   A. a face mask;
   B. a particulate collector disposed in a vicinity of a surface of the face mask, the particulate collector comprising a surface that (i) is any of water-soluble and adhesive, and (ii) is in fluid coupling with a reagent for a first biomarker;
   C. a condensate collector disposed in the vicinity of the surface of the face mask, the condensate collector comprising a hydrophobic field disposed adjacent to one or more hydrophilic channels;
   D. a transducer in fluid coupling with the one or more hydrophilic channels, the transducer including a bioreceptor for a second biomarker and generating an electrical signal in a presence of that second biomarker in a fluid.

2. The apparatus of claim 1, wherein the bioreceptor is matched to the second biomarker for lock and key selectivity screening.

3. The apparatus of claim 1, wherein the transducer transforms an output of the bioreceptor into the electrical signal.

4. The apparatus of claim 1, wherein the reagent is bound to a water-insoluble region of the particulate collector.

5. The apparatus of claim 4, wherein the reagent is bound to nanoparticles.

6. The apparatus of claim 1, wherein the reagent reacts with the first biomarker with a change in at least one of an optical signal and an electrical signal.

7. The apparatus of claim 1, wherein
   A. the condensate collector comprises a metallic sheet; and
   B. the hydrophobic field and the one or more hydrophilic channels are formed on the metallic sheet.

8. The apparatus of claim 1, wherein
   A. the face mask comprises a concavity adapted to receive at least one of a nose and a mouth; and
   B. the surface in the vicinity of which the condensate collector and the particulate collector are disposed is a surface of the concavity.

9. The apparatus of claim 8, wherein the hydrophobic field has disposed thereon beads of breath moisture droplets.

10. The apparatus of claim 9, wherein the one or more hydrophilic channels have disposed therein a fluid sample comprising said beads of breath moisture droplets.

11. The apparatus of claim 1, wherein the condensate collector comprises a substrate having the hydrophobic field and the one or more hydrophilic channels formed thereon.

12. The apparatus of claim 11, wherein the substrate comprises sheet aluminum.

13. The apparatus of claim 1, wherein the one or more hydrophilic channels are disposed within the hydrophobic field.

14. The apparatus of claim 1, wherein at least the hydrophobic field is disposed on a thermal mass.

15. The apparatus of claim 1, comprising a fluidic lateral flow assay disposed adjacent to one or more of the hydrophilic channels, the fluidic lateral flow assay including: a sample pad, a conjugate release pad, a flow membrane, and adsorbent pad.

16. The apparatus of claim 15, comprising a fluid dam disposed between fluidic lateral flow assay and one or more of the hydrophilic channels.

17. The apparatus of claim 16, comprising a fluid dam disposed between the sample pad and the conjugate release pad.

18. The apparatus of claim 1, wherein the particulate collector is capable of collecting particles of cough expellant.

19. Apparatus for diagnostic testing, comprising:
A. a face mask;
B. a particulate collector disposed in a vicinity of a surface of the face mask, the particulate collector comprising a surface that (i) is any of water-soluble and adhesive, and (ii) is capable of collecting particles comprising a first biomarker;
C. a condensate collector disposed in the vicinity of the surface of the face mask, the condensate collector comprising a hydrophobic field disposed adjacent to one or more fluid channels;
D. a transducer in fluid coupling with the one or more fluid channels, the transducer including a bioreceptor for a second biomarker and generating an electrical signal in a presence of that second biomarker in a fluid.

* * * * *